(12) United States Patent
Stull et al.

(10) Patent No.: US 11,305,002 B2
(45) Date of Patent: Apr. 19, 2022

(54) COMPOSITIONS AND TREATMENTS FOR HAEMOPHILUS INFLUENZAE

(71) Applicant: The Board of Regents of the University of Oklahoma, Norman, OK (US)

(72) Inventors: Terrence L. Stull, Oklahoma City, OK (US); Daniel J. Morton, Oklahoma City, OK (US); Thomas W. Seale, Edmond, OK (US); Paul W. Whitby, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 79 days.

(21) Appl. No.: 15/580,060

(22) PCT Filed: Jun. 7, 2016

(86) PCT No.: PCT/US2016/036180
§ 371 (c)(1),
(2) Date: Dec. 6, 2017

(87) PCT Pub. No.: WO2016/200787
PCT Pub. Date: Dec. 15, 2016

(65) Prior Publication Data
US 2018/0296661 A1  Oct. 18, 2018

Related U.S. Application Data

(60) Provisional application No. 62/208,023, filed on Aug. 21, 2015, provisional application No. 62/173,205, filed on Jun. 9, 2015.

(51) Int. Cl.
| | | |
|---|---|---|
| *A61K 39/102* | (2006.01) | |
| *A61K 9/00* | (2006.01) | |
| *C07K 14/285* | (2006.01) | |

(52) U.S. Cl.
CPC .......... *A61K 39/102* (2013.01); *A61K 9/0019* (2013.01); *C07K 14/285* (2013.01); *C07K 2317/32* (2013.01); *C07K 2317/34* (2013.01)

(58) Field of Classification Search
None
See application file for complete search history.

(56) References Cited

U.S. PATENT DOCUMENTS

| | | |
|---|---|---|
| 8,283,114 B2 | 10/2012 | Bakaletz |
| 2005/0158335 A1 | 7/2005 | Bakaletz et al. |
| 2008/0267966 A1 | 10/2008 | Vega et al. |
| 2013/0121915 A1 | 5/2013 | Paas et al. |

FOREIGN PATENT DOCUMENTS

| | | | |
|---|---|---|---|
| WO | 2005063802 A2 | 7/2005 | |
| WO | WO-2005111066 A2 * | 11/2005 | .......... C07K 14/285 |
| WO | 2010092176 A2 | 8/2010 | |

OTHER PUBLICATIONS

Murphy, T. F., "Vaccines for nontypeable Haemophilus influenzae: the future is now," Clinical and Vaccine Immunology, Mar. 18, 2015, vol. 22, No. 5, pp. 459-466.
Extended European Search Report issued in related European Patent Application EP 16808116.4, dated Mar. 28, 2019 (11 pp.).
Nizet, et al.; "A Virulent Nonencapsulated Haemophilus influenzae," The Journal of Infectious Diseases (1996), vol. 173, pp. 180-186.
Hempel, et al.; "The Role of the RNA Chaperone Hfq in Haemophilus influenzae Pathogenesis," BMC Microbiology (2013), vol. 13, No. 134, pp. 1-10.
Musser, et al.; "Genetic Relationships of Serologically Nontypable and Serotype b sSrains of Haemophilus influenzae," Infection and Immunicty (1986) vol. 52, No. 1, pp. 183-191.
Fleischmann, et al.; "Whole-Genome Random Sequencing and Assembly of Haemophilus influenzae Rd," Science (1995), vol. 269, pp. 496-512.
Harrison, et al.; "Genomic Sequence of an Otitis Media Isolate of Nontypeable Haemophilus influenzae Comparative Study with H. influenzae Serotype d, Strain KW20," Journal of Bacteriology (2005), vol. 187, No. 13, pp. 4627-4636.
Salzberg, et al.; "Microbial Gene Identification Using Interpolated Markov Models," Nucleic Acids Research (1998) vol. 26, No. 2, pp. 544-548.
Sali, et al.; "Comparative Protein Modelling by Satisfaction of Spatial Restraints," J Mol Biol (1993) vol. 234, pp. 779-815.
Fiser, et al.; "Modeling of Loops in Protein Structures," Protein Science (2000), vol. 9, pp. 1753-1773.
Bagos, et al.; "PRED-TMBB: A Web Server for Predicting the Topology of β-barrel Outer Membrane Proteins," Nucleic Acids Res (2004), vol. 32, Web Server issue, W400-W404.
Berven, et al.; "BOMP: A Program to Predict Integral β-barrel Outer Membrane Proteins Encoded Within Genomes of Gram-Negative Bacteria," Nucleic Acids Research (2004), vol. 32: Web Servier issue, pages W394-W399.
Krogh, et al.; "Predicting Transmembrane Protein Topology With a Hidden Markov Model: Application to Complete Genomes," J Mol Biol (2001), vol. 305, pp. 567-580.
Pisitkun, et al.; "NHLBI-AbDesigner: An Online Tool for Design of Peptide-Directed Antibodies," Am J Physiol Cell Physiol (2012) vol. 302, No. 1, pp. C154-C164.
Smith, et al.; "Production of Haemophilus influenzae b Meningitis in Infant Rats by Intraperitoneal Inoculation," Infection and Immunity (1973), vol. 8, No. 2, pp. 278-290.

(Continued)

*Primary Examiner* — Brian Gangle
(74) *Attorney, Agent, or Firm* — Rodney J. Fuller; Booth Udall Fuller, PLC

(57) ABSTRACT

Immunogenic peptides, fusion polypeptides, and carrier molecules which include the immunogenic peptides, and immunogenic compositions which include these immunogenic peptides, fusion polypeptides, and/or carrier molecules bearing the peptides, and which are able to elicit antibody production against *Haemophilus influenzae* (Hi), are disclosed. Also disclosed are methods of their use in causing an antibody response against one or more strains of Hi.

18 Claims, 5 Drawing Sheets

Specification includes a Sequence Listing.

(56) References Cited

OTHER PUBLICATIONS

Seale, et al.; "Complex Role of Hemoglobin and Hemoglobin-Haptoglobin Binding Proteins in Haemophilus influenzae Virulence in the Infant Rat Model of Invasive Infection," Infection and Immunity (2006), vol. 74, No. 11, pp. 6213-6225.

Morton, et al.; "Identification of a Haem-Utilization Protein (Hup) in Haemophilus influenzae," Microbiology (2004) vol. 150, pp. 3923-3933.

Hanson, et al.; "Identification of a Genetic Locus of Haemophilus influenzae Type b Necessary for the Binding and Utilization of Heme Bound to Human Hemopexin," Proc Natl Acad Sci USA (1992), vol. 89, pp. 1973-1977.

Morton, et al.; "The Haem-Haemopexin Utilization Gene Cluster (hxuCBA) as a Virulence Factor of Haemophilus influenzae," Microbiology (2007), vol. 153, pp. 215-224.

McCrea, et al.; "Relationships of Nontypeable Haemophilus influenzae Strains to Hemolytic and Nonhemolytic Haemophilus Haemolyticus Strains," J Clin Microbiol (2008), vol. 46, No. 2, pp. 406-416.

Yu, et al.; "PSORTb 3.0: Improved Protein Subcellular Localization Prediction With Refined Localization Subcategories and Predictive Capabilities for all Prokaryotes," Bioinformatics (2010) vol. 26, No. 13, pp. 1608-1615.

Postle et al.; "Touch and Go: Tying TonB to Transport," Mol Microbiol (2003) vol. 49, No. 4, pp. 869-882.

Wiener, Michael C. "TonB-Dependent Outer Membrane Transport: Going for Baroque?," Curr Opin Struct Biol (2005), vol. 15, pp. 394-400.

St. Geme, et al.; "A Prototype Two-Partner Secretion Pathway: The Haemophilus influenzae HMW1 and HMW2 Adhesin Systems," Trends in Microbiology (2009), vol. 17, No. 8, pp. 355-360.

Morton et al.; "Distribution of a Family of Haemophilus influenzae Genes Containing CCAA Nucleotide Repeating Units" FEMS Microbiology Letters (1999), vol. 174, pp. 303-309.

Hogg, et al.; "Characterization and Modeling of the Haemophilus influenzae Core and Supragenomes Based on the Complete Genomic Sequences of Rd and 12 Clinical Nontypeable Strains," Genome Biology (2007), vol. 8, No. 6, Article R103, 18 pages.

Novotny, et al.; "Epitope Mapping Immunodominant Regions of the PilA Protein of Nontypeable Haemophilus influenzae (NTHI) to Facilitate the Design of Two Novel Chimeric Vaccine Candidates," Vaccine (2010), 26 pages.

Whitby, et al.; "Antisera Against Certain Conserved Surface-Exposed Peptides of Nontypeable Haemophilus influenzae Are Protective," PLOS One (2015), vol. 10, No. 9: e0136867, 16 pages.

International Search Report, dated Nov. 28, 2016, in PCTUS2016/36180, filed Jun. 7, 2016.

Written Opinion of the International Searching Authority, dated Nov. 28, 2016, in PCTUS2016/36180, filed Jun. 7, 2016.

European Patent Office. Extended European Search Report for application 19201178.1, dated Jun. 30, 2020.

Dale, James B., "Multivalent group A streptococcal vaccine designed to optimize the immunogenicity of six tandem M protein fragments," Vaccine, Jan. 1999, vol. 17, Issue 2, pp. 193-200.

* cited by examiner

COMPOSITIONS AND TREATMENTS FOR HAEMOPHILUS INFLUENZAE

CROSS REFERENCE TO RELATED APPLICATIONS/INCORPORATION BY REFERENCE STATEMENT

This patent application is a US national stage application filed under 35 USC § 371 of International Application No. PCT/US2016/036180, filed Jun. 7, 2016; which claims benefit under 35 U.S.C. § 119(e) of provisional patent application U.S. Ser. No. 62/173,205, filed on Jun. 9, 2015; and provisional patent application U.S. Ser. No. 62/208,023, filed on Aug. 21, 2015. The entire contents of each of the above-referenced applications are expressly incorporated herein by reference.

BACKGROUND

*Haemophilus influenzae* (Hi) includes both typeable strains (types a, b, c, d, e, and f), which have capsules, and Nontypeable strains, which do not have capsules. Hi causes both invasive and noninvasive infections, including (but not limited to) otitis media, bacteremia, and exacerbations of chronic obstructive pulmonary disease; as such, Hi is a significant public health burden. The most commonly occurring infection caused by Nontypeable *Haemophilus influenzae* NTHi is acute otitis media (AOM). AOM accounts for 33% of visits by children to health care centers and is the most frequent reason children receive antibiotics. The incidence of AOM peaks between 6 and 12 months of life; almost 100% of children in developing communities and two-thirds of children in developed communities experience their first episode of OM (otitis media) by one year of age. By age 3 years, 80% of children in the U.S. have experienced at least one episode, and 40% have three or more recurrent episodes. Compared to children without AOM, those with acute AOM had 2 additional office visits, 0.2 additional emergency room visits, and 1.6 additional prescriptions per year. These visits lead to an estimated incremental increase in outpatient healthcare costs of $314 per year per child. The most common infections due to the typeable strains are bacteremia and meningitis caused by the type b strains.

Historically, *Streptococcus pneumoniae* was the most common AOM isolate, and NTHi was the second most common. Since the introduction of the PCV-7 *S. pneumoniae* vaccine in 2000, the number of cases of OM attributable to *S. pneumoniae* has markedly decreased. However, the overall number of cases of OM has been reduced only marginally, with reductions of about 7% reported when the PCV-7 vaccine is used in infancy. The relatively minor reduction in the incidence of OM is due to an increase in the proportion of OM attributable to NTHi, and NTHi is now reported as the predominant cause of AOM.

In previous decades, greater than 95% of the cases of invasive disease caused by *H. influenzae* were due to strains with the type b capsule. However, vaccines based on the type b capsular polysaccharide have virtually eliminated such infections in regions where the vaccine is extensively used. These vaccines are directed exclusively to the type b capsule. Since the NTHi strains do not have a capsule, these vaccines have no effect on NTHi, and NTHi continues to cause invasive disease principally in perinatal infants, young children, and those older than 65 years.

Several lines of evidence suggest that prevention of AOM due to NTHi is possible. First, AOM is largely a disease of infants in whom the serum and mucosal antibodies directed against common pathogens are low. Second, OM-prone children have lower levels of serum antibodies than healthy age-matched controls. Third, individuals with immunodeficiencies are predisposed to repeated NTHi infections. In addition, breast-feeding is associated both with a reduced frequency of AOM and higher levels of serum antibodies against NTHi in the nursing infant. Evidence from animal studies also supports the possibility of preventing AOM caused by NTHi.

For example, it is possible to protect against challenge by pre-immunization with pilins from the challenge isolate, although cross protection against unrelated isolates was not developed. Similarly, peptide motifs of the pilins were shown to protect, but only against homologous challenge. This lack of cross protection presumably results from known sequence heterogeneity of the pilin proteins. Other studies have assessed protection afforded by antibodies to a number of virulence factors, including major and minor outer membrane proteins (OMPs) and lipooligosaccharide. Finally, an 11-valent *S. pneumoniae* vaccine using *H. influenzae* protein D as a carrier molecule afforded partial protection (a reduction of 35%) against NTHi OM in a human clinical trial. However, a non-toxic, broadly cross-reactive immunoprotective NTHi vaccine composition has yet to be produced. It is an object of the present disclosure to provide such a composition.

BRIEF DESCRIPTION OF THE DRAWINGS

Several embodiments of the present disclosure are hereby illustrated in the appended drawings. It is to be noted, however, that the appended drawings only illustrate several typical embodiments and are therefore not intended to be considered limiting of the scope of the present disclosure.

DETAILED DESCRIPTION

Figure 1:
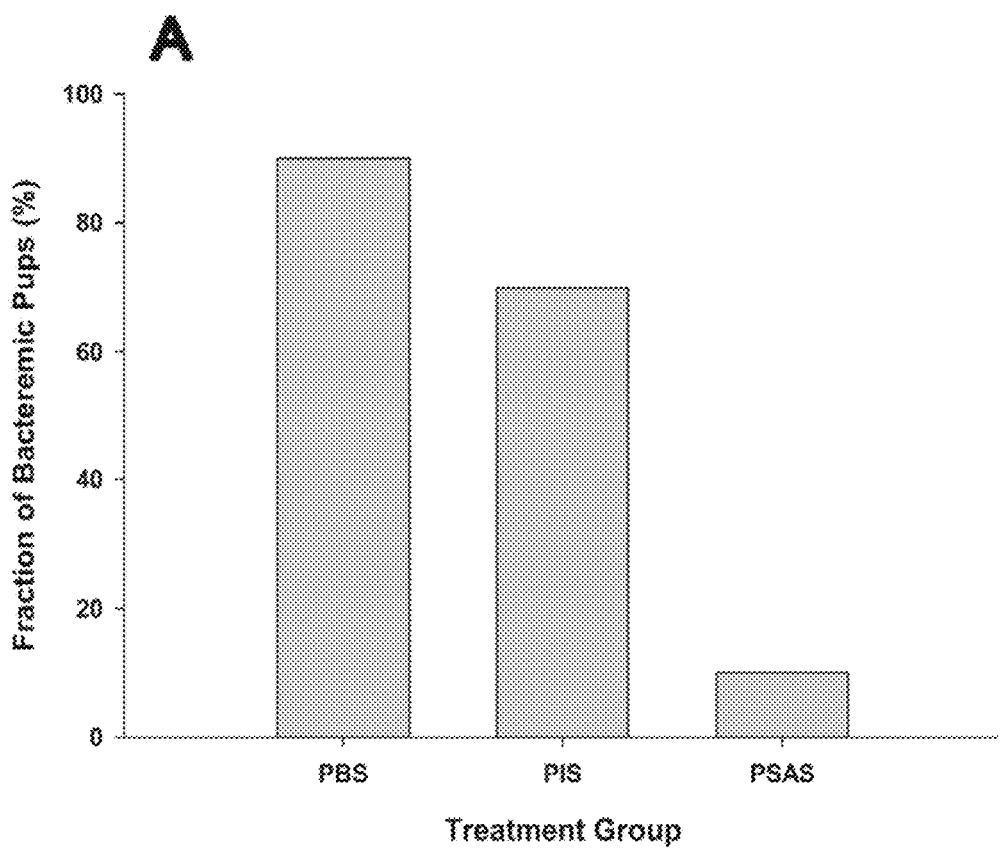
FIG. 1 depicts protection afforded by anti-HxuC antisera in the infant rat model of NTHi bacteremia. (A) Percentage of infected infant rats pretreated with pentavalent anti-HxuC antisera with detectable bacteremia 48 hours after infection. (B) Percentage of infected infant rats pretreated with antisera against specific HxuC peptides with detectable bacteremia 48 hours after infection. (C) Bacteremic titers in infected infant rats pretreated with antisera against specific HxuC peptides 48 hours after infection.
Figure 1:
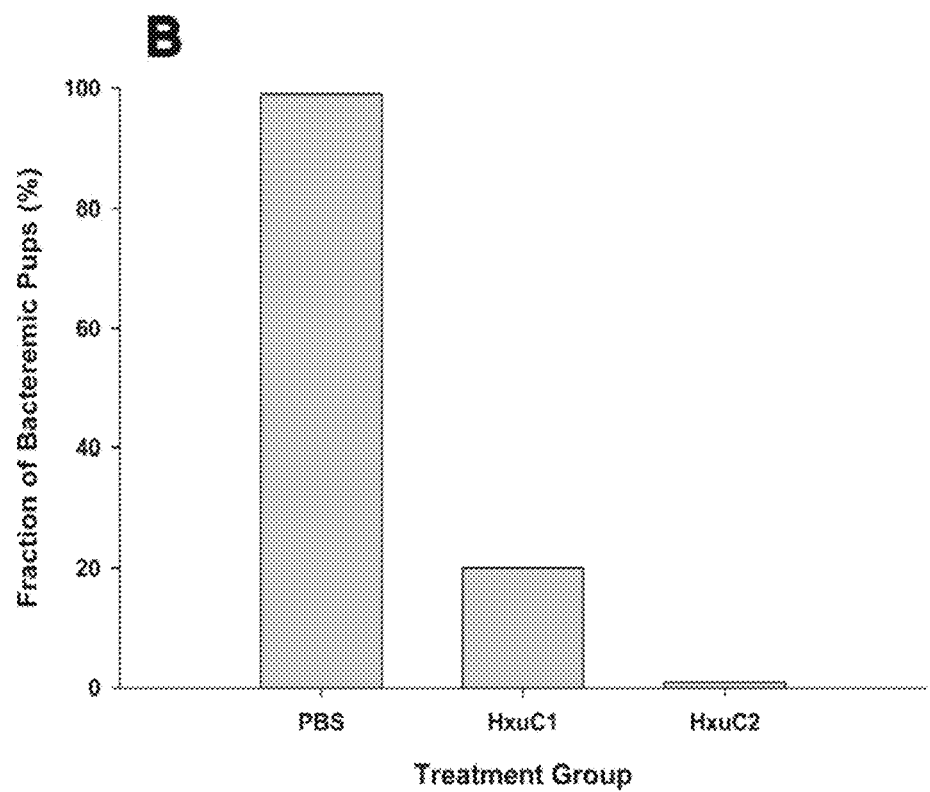
Figure 1:
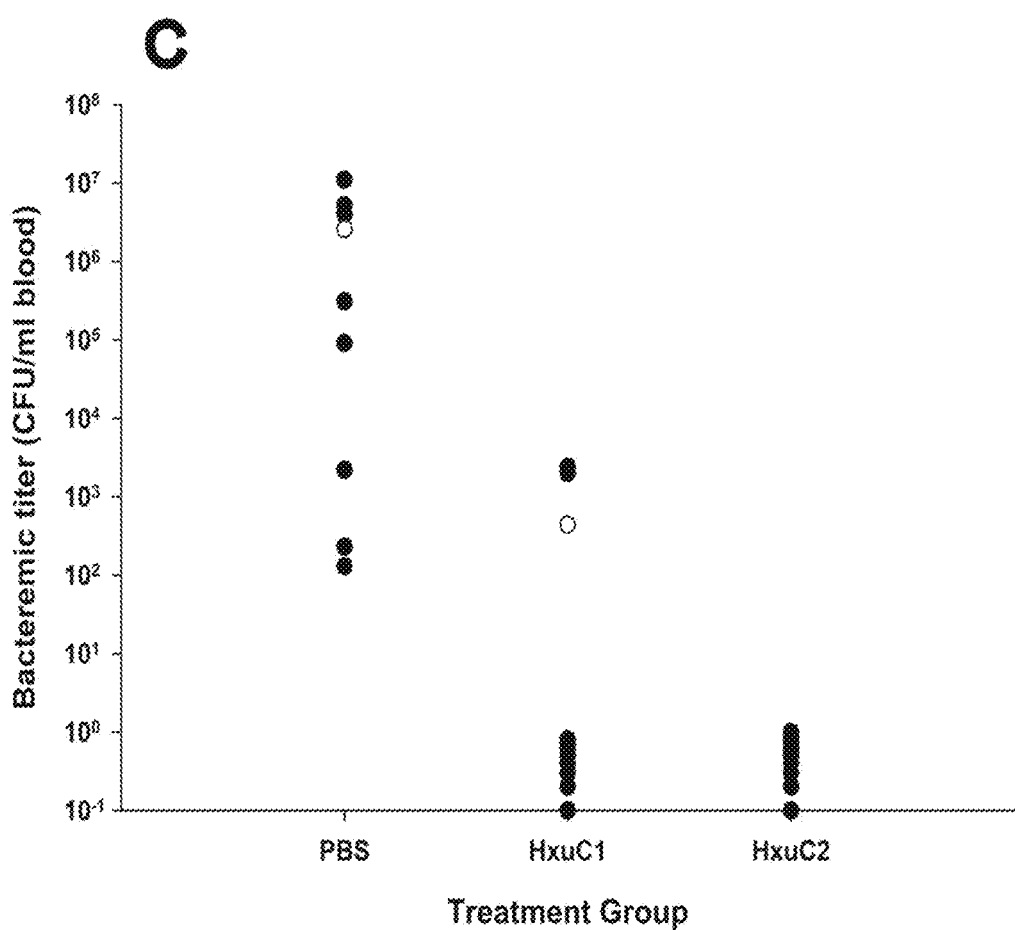

The present disclosure is directed, in certain embodiments, to immunogenic peptides that are able to elicit antibody production against *Haemophilus influenzae* (Hi). The present disclosure is also directed, in certain embodiments, to fusion polypeptides and carrier molecules that include the immunogenic peptides, and to immunogenic compositions that include these immunogenic peptides, fusion polypeptides, and/or carrier molecules bearing the peptides. The present disclosure is also directed, in certain embodiments, to methods of use of the above immunogenic peptides/polypeptides/carrier molecules/immunogenic compositions in causing an antibody response against one or more strains of Hi, for example (but not by way of limitation), as vaccines or for generating antisera for active or passive immunization of subjects against multiple strains of Hi; non-limiting strains to which the vaccines or antisera could be raised include both type b strains of Hi and Nontypeable *Haemophilus influenzae* (NTHi). The present disclosure further includes DNA and RNA nucleic acids that encode the immunogenic peptides, fusion polypeptides, and variants thereof disclosed elsewhere herein. The nucleic acids may be disposed in a vector such as a plasmid, or may be transfected into a host cell that may be cultured to produce the peptides and/or fusion polypeptides. In certain embodiments, the present disclosure is also directed to monoclonal and polyclonal antibodies generated against the immunogenic compositions described herein.

As noted above, NTHi causes significant disease, including (but not limited to) otitis media in children, exacerbations of chronic obstructive pulmonary disease, and invasive disease in susceptible populations. No vaccine is currently available to prevent NTHi disease. The interactions of NTHi and the human host are primarily mediated by lipooligosaccharide and a complex array of surface-exposed proteins (SEPs) that act as receptors, sensors, and secretion systems expressed on the bacterial cell surface. The work disclosed herein indicates that certain SEPs are present in all or nearly all NTHi strains and comprise antibody-accessible epitopes. Initially 15 genomic sequences available in the GenBank database were used. To attach confidence in the selection of conserved proteins, an additional twelve selected genomic sequences generated as part of the present disclosure were used to identify a core set of putative SEPs present in all strains. Sixty-two core SEPs were identified. Highly conserved epitopes from the core SEPs were selected for further assessment. Synthetic peptides based on a subset of these epitopes were used to raise antisera in rats. These antisera were used to assess passive protection in the infant rat model of invasive NTHi infection. Peptides that induced a protective antibody response represent epitopes that are protective and can be used in a vaccine composition to protect against NTHi infection, or against both Hi and NTHi, as described in more detail below. In contrast to the lack of capsule in NTHi, all type b Hi strains have surface exposed proteins, and the sequences of certain surface exposed peptides in these proteins are identical among both the NTHi strains and the encapsulated, typeable strains. Thus, the peptides described herein evoke antisera protective against invasive infections.

Before further description of various embodiments of the peptide, fusion polypeptide, and carrier molecule compositions, as well as methods of use thereof, of the present disclosure in more detail, it is to be understood that the present disclosure is not limited in application to the details of methods and compositions as set forth in the following description. The description provided herein is intended for purposes of illustration only and is not intended to be construed in a limiting sense. The present disclosure is capable of other embodiments or of being practiced or carried out in various ways. As such, the language used herein is intended to be given the broadest possible scope and meaning, and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that various embodiments of the present disclosure may be practiced without these specific details. In other instances, features that are well known to persons of ordinary skill in the art have not been described in detail to avoid unnecessary complication of the description. It is intended that all alternatives, substitutions, modifications, and equivalents apparent to those having ordinary skill in the art are included within the scope of the present disclosure as defined herein. Thus the examples described below, which include particular embodiments, will serve to illustrate the practice of the present disclosure, it being understood that the particulars shown are by way of example and for purposes of illustrative discussion of particular embodiments only and are presented in the cause of providing what is believed to be a useful and readily understood description of procedures, as well as of the principles and conceptual aspects of the present disclosure. All of the compositions and methods of production and application and use thereof disclosed herein can be made and executed without undue experimentation in light of the present disclosure. Thus, while the compositions and methods of the present disclosure have been described in terms of particular embodiments, it will be apparent to those of ordinary skill in the art that variations may be applied to the compositions and/or methods and in the steps or in the sequence of steps of the methods described herein without departing from the concept, spirit, and scope of the present disclosure.

All patents, published patent applications, and non-patent publications mentioned in the specification are indicative of the level of skill of those skilled in the art to which the present disclosure pertains. For example, U.S. Provisional patent applications Ser. No. 62/173,205 and Ser. No. 62/208,023, and all patents, published patent applications, and non-patent publications referenced in any portion of this application, are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB.

Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately," where used herein when referring to a measurable value such as an amount, a temporal duration, and the like, is meant to encompass, for example, variations of ±20%, or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, any reference to "one embodiment" or "an embodiment" means that a particular element, feature, composition, structure, or characteristic described in connection with the embodiment is included in at least one embodiment. The appearances of the phrase "in one embodiment" in various places in the specification are not necessarily all referring to the same embodiment.

The term "mutant" or "variant" is intended to refer to a protein, peptide, or nucleic acid which has at least one amino acid or nucleotide which is different from the wild type version of the protein, peptide, or nucleic acid, and includes, but is not limited to, point substitutions, multiple contiguous or non-contiguous substitutions, chimeras, or fusion proteins, and the nucleic acids which encode them. Examples of conservative amino acid substitutions include, but are not limited to, substitutions made within the same group such as within the group of basic amino acids (such as arginine, lysine, and histidine), acidic amino acids (such as glutamic acid and aspartic acid), polar amino acids (such as glutamine and asparagine), hydrophobic amino acids (such as leucine, isoleucine, and valine), aromatic amino acids (such as phenylalanine, tryptophan, and tyrosine) and small amino acids (such as glycine, alanine, serine, threonine, and methionine). Other examples of possible substitutions are described below.

The term "pharmaceutically acceptable" refers to compounds and compositions that are suitable for administration to humans and/or animals without undue adverse side effects (such as toxicity, irritation, and/or allergic response) commensurate with a reasonable benefit/risk ratio.

By "biologically active" is meant the ability to modify the physiological system of an organism without reference to how the active agent has its physiological effects.

As used herein, "pure" or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The terms "subject" and "patient" are used interchangeably herein and will be understood to refer to a warm-blooded animal, particularly a mammal. Non-limiting examples of animals within the scope and meaning of this term include dogs, cats, rabbits, rats, mice, guinea pigs, chinchillas, horses, goats, cattle, sheep, zoo animals, Old and New World monkeys, non-human primates, and humans.

"Treatment" refers to therapeutic treatments. "Prevention" refers to prophylactic or preventative treatment measures. The term "treating" refers to administering the composition to a patient for therapeutic purposes.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques that are well known in the art.

The term "effective amount" refers to an amount of an active agent that is sufficient to exhibit a detectable therapeutic effect without excessive adverse side effects (such as toxicity, irritation, and allergic response) commensurate with a reasonable benefit/risk ratio when used in the manner of the present disclosure. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "peptide" is used herein to designate a series of amino acid residues, connected one to the other typically by peptide bonds between the alpha-amino and carbonyl groups of the adjacent amino acids to form an amino acid sequence. In certain embodiments, the immunogenic peptides can range in length from 8 to 15 to 25 to 40 to 60 to 75 to 100 amino acids, for example, 8, 9, 10, 11, 12, 13, 14, 15, 16, 17, 18, 19, 20, 21, 22, 23, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. The term "polypeptide" or "protein" is used herein to designate a series of amino acid residues, connected one to the other typically by peptide bonds between the alpha-amino and carbonyl groups of the adjacent amino acids, wherein the length is longer than a single peptide. A "fusion protein" or "fusion polypeptide" refers to proteins or polypeptides (and may be used interchangeably) which have been created by recombinant or synthetic methods to combine peptides in a serial configuration.

As used herein "immunogenic composition" refers to a composition containing, for example, peptides, polypeptides, fusion proteins, or carrier molecules with peptides or polypeptides conjugated thereto, which elicits an immune response, such as the production of antibodies in a host cell or host organism. The immunogenic composition may optionally contain an adjuvant. In certain embodiments, the immunogenic composition is a vaccine.

Where used herein, the term "antigenic fragment" refers to a fragment of an antigenic peptide described herein that is also able to elicit an immunogenic response.

The term "homologous" or "% identity" as used herein means a nucleic acid (or fragment thereof) or an amino acid sequence (peptide or protein) having a degree of homology to the corresponding reference (e.g., wild type) nucleic acid, peptide, or protein that may be equal to or greater than 70%, or equal to or greater than 80%, or equal to or greater than 85%, or equal to or greater than 86%, or equal to or greater than 87%, or equal to or greater than 88%, or equal to or greater than 89%, or equal to or greater than 90%, or equal to or greater than 91%, or equal to or greater than 92%, or equal to or greater than 93%, or equal to or greater than 94%, or equal to or greater than 95%, or equal to or greater than 96%, or equal to or greater than 97%, or equal to or greater than 98%, or equal to or greater than 99%. For example, in regard to peptides or polypeptides, the percentage of homology or identity as described herein is typically calculated as the percentage of amino acid residues found in the smaller of the two sequences which align with identical amino acid residues in the sequence being compared, when four gaps in a length of 100 amino acids may be introduced to assist in that alignment (as set forth by Dayhoff, in Atlas of Protein Sequence and Structure, Vol. 5, p. 124, National Biochemical Research Foundation, Washington, D.C. (1972)). In one embodiment, the percentage homology as described above is calculated as the percentage of the components found in the smaller of the two sequences that may also be found in the larger of the two sequences (with the introduction of gaps), with a component being defined as a sequence of four contiguous amino acids. Also included as substantially homologous is any protein product that may be isolated by virtue of cross-reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul (Proc. Natl. Acad. Sci. USA (1990) 87:2264-2268; modified as in Karlin & Altschul (Proc. Natl. Acad. Sci. USA (1993) 90:5873-5877)). In at least one embodiment, "% identity" represents the number of amino acids or nucleotides that are identical at corresponding positions in two sequences of a protein having the same activity or encoding similar proteins. For example, two amino acid sequences each having 100 residues will have 95% identity when 95 of the amino acids at corresponding positions are the same. Similarly, two amino acid sequences each having 100 residues will have at least 90% identity when at least 90 of the amino acids at corresponding positions are the same. Similarly, two amino acid sequences each having 20 residues will have 95% identity when 19 of the amino acids at corresponding positions are the same, or 90% identity when at least 18 of the amino acids at corresponding positions are the same, or 85% identity when at least 17 of the amino acids at corresponding positions are the same, or 80% identity when at least 16 of the amino acids at corresponding positions are the same.

Further, where a sequence is described herein as having "at least X % identity to" a reference sequence, this is intended to include, unless indicated otherwise, all percentages greater than X %, such as for example, (X+1)%, (X+2)%, (X+3)%, (X+4)%, and so on, up to 100%.

Another example of a mathematical algorithm used for comparison of sequences is the algorithm of Myers & Miller (CABIOS (1988) 4:11-17). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman (Proc. Natl. Acad. Sci. USA (1988) 85:2444-2448).

Another algorithm is the WU-BLAST (Washington University BLAST) version 2.0 software (WU-BLAST version 2.0 executable programs for several UNIX platforms). This program is based on WU-BLAST version 1.4, which in turn is based on the public domain NCBI-BLAST version 1.4 (Altschul & Gish, 1996, Local alignment statistics, Doolittle ed., Methods in Enzymology 266, 460-480; Altschul et al., Journal of Molecular Biology 1990, 215, 403-410; Gish & States, Nature Genetics, 1993, 3: 266-272; Karlin & Altschul, 1993, Proc. Natl. Acad. Sci. USA 90, 5873-5877; all of which are incorporated by reference herein).

In addition to those otherwise mentioned herein, mention is made also of the programs BLAST, gapped BLAST, BLASTN, BLASTP, and PSI-BLAST, provided by the National Center for Biotechnology Information (Bethesda, Md.). These programs are widely used in the art for this purpose and can align homologous regions of two amino acid sequences. In all search programs in the suite, the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

The terms "polynucleotide sequence" or "nucleic acid," as used herein, include any polynucleotide sequence which encodes a peptide or fusion protein (or polypeptide) including polynucleotides in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand. The polynucleotide sequence encoding a peptide or fusion protein, or encoding a therapeutically effective variant thereof, can be substantially the same as the coding sequence of the endogenous coding sequence as long as it encodes an immunogenically-active peptide or fusion protein. Further, the peptide or fusion protein may be expressed using polynucleotide sequence(s) that differ in codon usage due to the degeneracies of the genetic code or allelic variations. Moreover, the peptides and fusion proteins of the present disclosure and the nucleic acids that encode them include peptide/protein and nucleic acid variants that comprise additional substitutions (conservative or non-conservative). For example, the immunogenic peptide variants include, but are not limited to, variants that are not exactly the same as the sequences disclosed herein, but which have, in addition to the substitutions explicitly described for various sequences listed herein, additional substitutions of amino acid residues (conservative or non-conservative) which substantially do not impair the activity or properties of the variants described herein. Examples of such conservative amino acid substitutions may include, but are not limited to: ala to gly, ser, or thr; arg to gln, his, or lys; asn to asp, gln, his, lys, ser, or thr; asp to asn or glu; cys to ser; gln to arg, asn, glu, his, lys, or met; glu to asp, gln, or lys; gly to pro or ala; his to arg, asn, gln, or tyr; ile to leu, met, or val; leu to ile, met, phe, or val; lys to arg, asn, gln, or glu; met to gln, ile, leu, or val; phe to leu, met, trp, or tyr; ser to ala, asn, met, or thr; thr to ala, asn, ser, or met; trp to phe or tyr; tyr to his, phe or trp; and val to ile, leu, or met. One of ordinary skill in the art would readily know how to make, identify, select, or test such variants for immunogenic activity against NTHi.

The terms "infection," "transduction," and "transfection" are used interchangeably herein and refer to introduction of a gene, nucleic acid, or polynucleotide sequence into cells such that the encoded protein product is expressed. The polynucleotides of the present disclosure may comprise additional sequences, such as additional coding sequences within the same transcription unit, controlling elements such as promoters, ribosome binding sites, transcription terminators, polyadenylation sites, additional transcription units under control of the same or different promoters, sequences that permit cloning, expression, homologous recombination, and transformation of a host cell, and any such construct as may be desirable to provide embodiments of the present disclosure.

In certain embodiments, the present disclosure includes expression vectors capable of expressing one or more fusion polypeptides described herein. Expression vectors for different cell types are well known in the art and can be selected without undue experimentation. Generally, the DNA encoding the fusion polypeptide is inserted into an expression vector, such as (but not limited to) a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Guidance can be found e.g., in Sambrook et al. (Molecular Cloning: A Laboratory Manual, 3d ed., Cold Spring Harbor Laboratory Press, N.Y. 2001)).

The optimum amount of each peptide to be included in the vaccine and the optimum dosing regimen can be determined by one skilled in the art without undue experimentation. For example (but not by way of limitation), the peptide or its variant may be prepared for intravenous (i.v.) injection, sub-cutaneous (s.c.) injection, intradermal (i.d.) injection, intraperitoneal (i.p.) injection, or intra-muscular (i.m.) injection. Particular, non-limiting routes of DNA injection are i.d., i.m., s.c., i.p., and i.v. The peptides may be substantially pure or combined with one or more immune-stimulating adjuvants (as discussed elsewhere herein), or used in combination with immune-stimulatory cytokines, or administered with a suitable delivery system, such as (but not limited to) liposomes. Adjuvants are substances that non-specifically enhance or potentiate the immune response (e.g., immune responses mediated by CTLs and helper-T (TH) cells to an antigen, and would thus be considered useful in the composition of the present disclosure when used as a vaccine. Suitable adjuvants include, but are not limited to: 1018 ISS, aluminium salts such as but not limited to alum (potassium aluminum sulfate), aluminum hydroxide, aluminum phosphate, or aluminum sulfate, Amplivax, AS15, BCG, CP-870,893, CpG7909, CyaA, Mologen's dSLIM, GM-CSF, IC30, IC31, Imiquimod, ImuFact IMP321, interferon-alpha or -beta, IS Patch, ISS, ISCOMs, JuvImmune, LipoVac, MF59, monophosphoryl lipid A, and other non-toxic LPS derivatives, Montanide IMS 1312, Montanide ISA 206, Montanide ISA 50\1, Montanide ISA-51, OK-432, and OM-174. Non-limiting examples of other pharmaceutically suitable adjuvants include nontoxic lipid A-related adjuvants such as, by way of non-limiting example, nontoxic monophosphoryllipid A (see, e.g., Persing et al., Trends Microbial. 10:s32-s37 (2002)), for example, 3 De-0-acylated monophosphoryllipid A (MPL) (see, e.g., United Kingdom Patent Application No. GB 2220211). Other useful adjuvants include QS21 and QuilA that comprise a triterpene glycoside or saponin isolated from the bark of the *Quillaja saponaria* Molina tree found in South America (see, e.g., Kensil et al., in Vaccine Design: The Subunit and Adjuvant Approach (eds. Powell and Newman, Plenum Press, N Y, 1995); and U.S. Pat. No. 5,057, 540). Non-limiting examples of other suitable adjuvants include polymeric or monomeric amino acids such as polyglutamic acid or polylysine, liposomes, and CpG (see, e.g., Klinman (Int. Rev. Immunol. (2006) 25(3-4): 135-54), and U.S. Pat. No. 7,402,572). Other examples of adjuvants that may be used in the compositions disclosed herein include but are not limited to those disclosed in U.S. Pat. No. 8,895,514.

Cytotoxic T-cells (CTLs) recognize an antigen in the form of a peptide bound to an MHC molecule (e.g., class I or II) rather than the intact foreign antigen itself. The MHC molecule itself is located at the cell surface of an antigen presenting cell (APC). Thus, an activation of CTLs is only possible if a trimeric complex of peptide antigen, WIC molecule, and APC is present. Correspondingly, certain embodiments of the present disclosure include compositions including APCs having the peptides displayed thereon via WIC molecules.

In other embodiments, the composition may include sugars, sugar alcohols, amino acids such as glycine, arginine, glutamic acid and others as framework former. The sugars may be mono-, di-, or trisaccharides. These sugars may be used alone as well as in combination with sugar alcohols. Non-limiting examples of sugars include: glucose, mannose, galactose, fructose or sorbose as monosaccharides; saccharose, lactose, maltose or trehalose as disaccharides; and raffinose as a trisaccharide. A sugar alcohol may be, for example (but not b y way of limitation), mannitol and/or sorbitol. Furthermore, the compositions may include physiological well tolerated excipients such as (but not limited to) antioxidants like ascorbic acid or glutathione; preserving agents such as phenol, m-cresol, methyl- or propylparaben, chlorobutanol, thiomersal (thimerosal), or benzalkoniumchloride; and solubilizers such as polyethylene glycols (PEG), e.g., PEG 3000, 3350, 4000 or 6000, or cyclodextrins, e.g., hydroxypropyl-cyclodextrin, sulfobutylethyl-cyclodextrin or y-cyclodextrin, or dextrans or poloxamers, e.g., poloxamer 407, poloxamer 188, Tween 20 or Tween 80.

In other embodiments, the present disclosure includes a kit comprising (a) a container that contains one or more pharmaceutical compositions as described herein, in solution or in lyophilized form; (b) optionally, a second container containing a diluent or reconstituting solution for the lyophilized formulation; and (c) optionally, instructions for (i) use of the solution or (ii) reconstitution and/or use of the lyophilized formulation. The kit may further comprise one or more of (iii) a buffer, (iv) a diluent, (v) a filter, (vi) a needle, or (vii) a syringe. The container is (in particular, non-limiting embodiments) a bottle, a vial, a syringe, or a test tube; and it may be a multi-use container. The container may be formed from a variety of materials such as (but not limited to) glass or plastic. The kit and/or container may contain instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous or intramuscular administration. The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution). The kit may further include other materials desirable from a commercial and user standpoint, including other buffers, diluents, filters, needles, syringes, and package inserts with instructions for use.

An antibody that specifically binds to an immunogenic peptide (and to a fusion polypeptide, dimeric peptide, full length or mature protein, or bacteria expressing the protein) may belong to any immunoglobulin class, for example IgG, IgE, IgM, IgD, or IgA. For characterizing the immunogenic peptides and fusion polypeptides described herein, use of polyclonal and/or monoclonal antibodies may be desired. The antibody may be obtained from or derived from an animal, for example, fowl (e.g., chicken) and mammals, which include but are not limited to a mouse, rat, chinchilla, hamster, rabbit, other rodent, a cow, horse, sheep, goat, camel, human, or other primate. As described herein, polyclonal antisera are obtained from an animal by immunizing the animal with an immunogenic composition comprising an immunogenic peptide, a plurality of immunogenic peptides, a fusion polypeptide, or a plurality of fusion polypeptides.

The level to which antibodies bind to an immunogenic peptide or fusion polypeptide as described herein can be readily determined using any one or more immunoassays that are routinely practiced by persons having ordinary skill in the art. By way of non-limiting example, immunoassays include ELISA, immunoblot, radioimmunoassay, immunohistochemistry, and fluorescence activated cell sorting (FACS).

Non-human animals that may be immunized with any one or more of the immunogenic peptides, fusion polypeptides, or immunogenic compositions comprising the same, include by way of non-limiting example: mice, rats, rabbits, hamsters, ferrets, dogs, cats, camels, sheep, cattle, pigs, horses, goats, chickens, llamas, and non-human primates (e.g., cynomolgus macaque, chimpanzee, rhesus monkeys, orangutan, and baboon). Adjuvants typically used for immunization of non-human animals include, but are not limited to, Freund's complete adjuvant, Freund's incomplete adjuvant, montanide ISA, Ribi Adjuvant System (RAS) (GlaxoSmithKline, Hamilton, Mont.), and nitrocellulose-adsorbed antigen. In general, after the first injection, a subject receives one or more booster immunizations according to a particular (but non-limiting) schedule that may vary according to, inter alia, the immunogen, the adjuvant (if any), and/or the particular subject species. In animal subjects, the immune response may be monitored by periodically bleeding the animal, separating the sera from the collected blood, and analyzing the sera in an immunoassay, such as (but not limited to) an ELISA assay, to determine the specific antibody titer. When an adequate antibody titer is established, the animal subject may be bled periodically to accumulate the polyclonal antisera. Polyclonal antibodies that bind specifically to the immunogen may then be purified from immune antisera, for example, by affinity chromatography using protein A or protein G immobilized on a suitable solid support, as understood by persons having ordinary skill in the art. Affinity chromatography may be performed wherein an antibody specific for an Ig constant region of the particular immunized animal subject is immobilized on a suitable solid support. Affinity chromatography may also incorporate use of one or more immunogenic peptides, or fusion proteins, which may be useful for separating polyclonal antibodies by their binding activity to a particular immunogenic peptide. Monoclonal antibodies that specifically bind to an immunogenic peptide and/or fusion protein, and immortal eukaryotic cell lines (e.g., hybridomas) that produce monoclonal antibodies having the desired binding specificity, may also be prepared, for example, using the technique of Kohler and Milstein ((Nature, 256:495-97 (1976); and Eur. J. Immunol. 6:511-19 (1975)) and improvements thereto.

The immunogenic compositions described herein may be formulated by combining a plurality of immunogenic peptides and/or a plurality of fusion polypeptides and/or carrier molecule-linked immunogenic peptides with at least one pharmaceutically acceptable excipient. As described herein the immunogenic compositions may further comprise a pharmaceutically suitable adjuvant. Typically, all immunogenic peptides or all fusion polypeptides intended to be administered to a subject are combined in a single immunogenic composition, which may include at least one pharmaceutically acceptable excipient and which may further include at least one pharmaceutically suitable adjuvant. Alternatively, for example, multiple immunogenic compositions may be formulated separately for separate administration, which could be by any route described herein or otherwise known in the art and which could be sequential or concurrent.

The immunogenic compositions described herein may be formulated as sterile aqueous or non-aqueous solutions, suspensions, or emulsions, which as described herein may additionally comprise a physiologically acceptable excipient (which may also be called a carrier) and/or a diluent. The immunogenic compositions may be in the form of a solid, liquid, or gas (aerosol). Alternatively, immunogenic compositions described herein may be formulated as a lyophilate (i.e., a lyophilized composition), or may be encapsulated within liposomes using technology well known in the art. As noted elsewhere herein, the immunogenic compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins (such as albumin), polypeptides or amino acids such as glycine, antioxidants, chelating agents such as EDTA or glutathione, stabilizers, dyes, flavoring agents, suspending agents, and/or preservatives. In general, as discussed herein, the type of excipient is selected on the basis of the mode of administration. The compositions and preparations described herein may be formulated for any appropriate manner of administration, including, for example (but not by way of limitation): topical, buccal, lingual, oral, intranasal, intrathecal, rectal, vaginal, intraocular, subconjunctival, transdermal, sublingual, or parenteral administration.

Dosage size may generally be determined in accordance with accepted practices in the art. The dose may depend upon the body mass, weight, or blood volume of the subject being treated. In general, the amount of an immunogenic peptide(s), fusion polypeptide(s), and/or carrier molecule composition(s) as described herein that is present in a dose, is in a range of, for example (but not limited to), about 1 μg to about 100 mg, from about 10 μg to about 50 mg, from about 50 μg to about 10 mg and comprising an appropriate dose for a 5-50 kg subject. Booster immunizations may be administered multiple times (e.g., two times, three times, four times, or more), at desired time intervals ranging from, for example, about 2 weeks to about 26 weeks, such as about 2, 4, 8, 12, 16, or 26 week intervals. The time intervals between different doses (e.g., between the primary dose and second dose, or between the second dose and a third dose) may not be the same, and the time interval between each two doses may be determined independently. Non-limiting embodiments of therapeutically effective amounts of peptides or fusion polypeptides of the present disclosure will generally contain sufficient active substance to deliver from about 0.1 μg/kg to about 100 mg/kg (weight of active substance/body weight of the subject). Particularly, the composition will deliver about 0.5 μg/kg to about 50 mg/kg, and more particularly about 1 μg/kg to about 10 mg/kg.

In certain embodiments, the present disclosure is directed to peptide compositions comprising at least one or two or three or four or five or more (e.g., 6, 7, 8, 9, 10, 11, 12, 13, 14, 15, 16, 17, 18, 19, 20 or more) different peptides having an amino acid sequence as set forth in the group of peptides shown in Table 1, Table 3, or Table 4, and/or a variant amino acid sequence thereof that has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99% identity to said peptide(s) in the group of Table 1, Table 3, or Table 4, and/or a polynucleotide containing a nucleic acid encoding a peptide in the group of Table 1, Table 3, or Table 4, or the variant amino acid sequence, and a pharmaceutically acceptable carrier. The peptides can be either concantenated (conjugated in series with or without linker sequences between the peptides to form one or more fusion polypeptides) or conjugated to one or more carrier molecules, as described in further detail below. For example, the peptides may be conjugated or otherwise coupled to a suitable carrier molecule such as, but not limited to, tetanus toxoid protein, diphtheria toxoid protein, CRM197 protein, *Neisseria meningitidis* outer membrane complex, *Haemophilus influenzae* protein D, pertussis toxin mutant, keyhole limpet haemocyanin (KLH), ovalbumin, and/or bovine serum albumin (BSA). Other examples of carrier proteins that may be used include, but are not limited to, those disclosed in U.S. Published Patent Applications 2013/0072881, 2013/0209503, and 2013/0337006.

In certain embodiments, the one or more immunogenic peptides comprise, or are contained within, a single fusion polypeptide, or are coupled to one or more carrier molecules. Additional peptides may optionally be provided in a separate fusion polypeptide or carrier molecule than the composition containing the first fusion polypeptide. In one particular embodiment, the fusion polypeptide or carrier molecule comprises at least 1, 2, 3, 4, 5, 6, 7, 8, 9, 10, or 11 immunogenic peptides, at least 5 of which are different from each other. The order in which the immunogenic peptides are linked on the fusion polypeptides may be readily determined by a person of ordinary skill in the art using methods and techniques described herein and routinely practiced in the art, and therefore the order does not require undue empirical, trial and error analysis to ensure optimization of the immunogenicity of each fusion polypeptide. In certain embodiments, the immunogenic peptide at the amino-terminal end of the fusion polypeptide is repeated (i.e., duplicated) at the carboxy terminal end of the fusion polypeptide. Methods of formation of such fusion polypeptides (fusion proteins) are known by persons having ordinary skill in the art; thus, it is not considered necessary to include a detailed discussion thereof herein. However, non-limiting exemplary methods for the formation of fusion polypeptides are shown in U.S. Pat. No. 8,697,085, the entirety of which is hereby explicitly incorporated by reference herein.

The individual immunogenic peptides and variants thereof of the present disclosure generally have an overall length in a range from 8 to 100 amino acids, for example in a range from 9 to 75 amino acids, in a range from 10 to 60 amino acids, and in a range from 12 to 30 amino acids, including any integeric value within any of said ranges, including, but not limited to, any of the peptides having a sequence as set forth in Table 1, Table 3, or Table 4. These sequences can be core sequences which further include amino acid flanking extensions on the C-terminal and/or the N-terminal ends. The extensions may comprise, for example, 1 to 12 amino acids, provided that the peptide retains its immunogenicity. As noted above, the variants of the individual immunogenic peptides may have amino acid sequences that have at least 80% or more identity to the peptides of Table 1, Table 3, or Table 4.

The embodiments of the present disclosure will be more readily understood by reference to the following examples and description, which as noted above are included merely for purposes of illustration of certain aspects and embodiments of the present disclosure, and are not intended to be limiting. The following detailed examples and methods describe how to make and use various peptides, fusion proteins, and peptide-linked immunogenic carrier molecules of the present disclosure and are to be construed, as noted above, only as illustrative, and not limitations of the disclosure in any way whatsoever. Those skilled in the art will promptly recognize appropriate variations from the materials and procedures described herein.

EXAMPLES

Materials and Methods

Bacterial Strains and Growth Conditions

The NTHi strain R2866 was isolated from the blood of an immunocompetent child with clinical signs of meningitis subsequent to AOM [1]. This strain has previously been utilized in the infant rat model of invasive *H. influenzae* disease [2]. NTHi strain sequences used to generate alignments included sequences available through GenBank as well as multiple strains sequenced in house. Sequences obtained through GenBank were from the following strains: 3655, 6P18H1, 7P49H1, PittAA, PittEE, PittGG, PittHH, PittII, R3021, R2846, R2866, 22.1-21, 22.4-21, 86-028NP, and NT127. Strains sequenced in house were from the inventor's laboratory collection and included several selected from those typed by electrophoretic mobility of 15 metabolic enzymes [3]. These strains were selected to represent the breadth of the species as defined by electrophoretic type (ET) and were HI1373, HI1374, HI1388, HI1394, HI1408, HI1417, and HI1426 representing, respectively, ET's 13, 26, 43, 53, 68, 77, and 86. An additional five clinical isolates selected from the inventor's collection were also sequenced: HI1722, HI1974, HI2114, HI2116, and HI2343.

Isolates of *H. influenzae* were routinely maintained on chocolate agar with bacitracin at 37° C. Broth cultures of *H. influenzae* were grown in brain heart infusion (BHI) agar supplemented with 10 µg/ml heme and 10 µg/ml β-NAD (supplemented BHI; sBHI).

Genome Sequencing of NTHi Strains

Chromosomal DNA was isolated from bacteria recovered from fresh 12 hour broth cultures using the DNeasy Blood and Tissue Kit (Qiagen, Hilden, Germany) as described by the manufacturer. Genome sequences of the NTHi strains were obtained using the SOLiD™ V3.0 platform (Applied Biosystems, Foster, Calif.) at the Laboratory for Molecular Biology and Cytometry Research, University of Oklahoma Health Sciences Center (Oklahoma City, Okla.). A 10 µg sample of chromosomal DNA was sonicated with the Covaris S2 focused-ultrasonicator in order to generate fragments of 80-110 bp to be used for building fragment DNA libraries per existing SOLiD™ protocols (Applied Biosystems, Foster City, Calif.). After shearing, DNA was end repaired and purified using PureLink PCR purification columns (Invitrogen, Carlsbad, Calif.) per the manufacturer's protocols. SOLID™ sequencing adapters (P1 and P2) were ligated to the DNA fragments, and the samples were run on agarose gels in order to size select and gel purify the 150-200 bp products, followed by PCR amplification and nick translation for the adapter ligated products. Each DNA fragment library was column purified (Qiagen min-elute columns) and quantified using the Invitrogen Qubit fluorometer and broad range DNA assay. A standard amount (60 pg) for each library was used for separate emulsion PCR reactions (ePCR) following existing SOLiD™ protocols. Approximately $2.5 \times 10^7$ beads were deposited for each sample onto a separate region of an octet slide for sequencing. Using the SOLiD™ V3.0, 50-bp sequencing reads were generated for each sample. Resulting high quality reads were compared and aligned to the existing genome sequences of the *H. influenzae* strains Rd KW20, 86-028NP and 10810 to determine sequence homology using the SETS software tool that is integrated into the SOLiD™ platform. Additional reference alignments and/or assembly of orphan reads were processed using the CLC Genomics Workbench software package (CLC Bio USA, Cambridge, Mass.) and default parameters for de novo assembly.

Annotation of the NTHi genomic sequences was performed in house and was based on comparative analyses between Rd KW20 [4], NTHi 86-028NP [5], and the NTHi R2846 sequences (GenBank Accession number CP002277.1). Genes were predicted using GLIMMER [6], trained on the codon usage pattern in strain Rd KW20. Predicted amino acid sequences for each called gene were compared between strains to determine consensus start sites and to account for frameshifted genes present in each strain. Manual annotation of non-redundant genes was performed by comparison to complete genomic sequences in other bacterial species. Using the sequences of Rd KW20, 86-028NP, R2846, and R2866, the probable ORFs were predicted.

Identification of SEPs Present in all NTHi Strains

Initially, the complement of putative surface-exposed proteins (SEPs) of the isolate NTHi 86-028NP was determined based on the reported annotation of this isolate [5]. Hypothetical proteins were individually examined to determine the presence of leader sequences and/or other indicators that they may be secreted or membrane bound. All identified proteins were then used to query the presence of homologs in the other sequenced NTHi. Absence of a homolog in any of the sequenced NTHi excluded that protein from further consideration. Once each core SEP was identified, Geneious software (Biomatters Ltd., Auckland, New Zealand) was used to perform sequence alignments with all the known homologs of a given protein in all the available NTHi genomes.

Molecular Modeling

The identified core SEP genes of NTHI 86-028NP were individually examined to determine homology to other known structurally defined proteins. Structures were generated using Modweb web server (University of California, San Francisco) based on the Modeller algorithm [7,8], the Molecular Modeling Database (Cn3D) and other stand-alone structural prediction algorithms. Proteins that shared no significant similarities with other modeled proteins were examined to determine regions indicative of secondary structure using PRED-TMBB, BOMP (β-barrel), and TMHMM (α-helix) [9-11].

Selection of Peptides

From these models, predicted surface-exposed regions greater than 10 amino acids long were selected. Multiple sequence alignments were performed with each core protein. All NTHi homologs of each protein from both complete and partial gene and genome sequences were used to perform these alignments. For the majority of proteins, more than 40

NTHi sequences were aligned. External regions greater than 10 amino acids in length were further examined to identify the degree of conservation of sequence across the NTHi. Regions with high conservation were selected as potential antigens. Some selected external loops were longer than 25 amino acids. In these cases, AbDesigner [12] was used to determine the most immunogenic region. A truncated synthetic peptide was then selected from this region for further study. Synthetic peptides with >95% purity were synthesized by SynBioSci Corp. (San Francisco, Calif.), Peptide 2.0 Inc. (Chantilly, Va.), or Thermo Fisher (Waltham, Mass.). During synthesis, an aliquot of each peptide was conjugated to Keyhole limpet haemocyanin (KLH) to facilitate immunization studies. A second aliquot was conjugated to biotin for use in ELISA assays.

Immunization of Rats and Production of Antisera

Antisera against each synthetic peptide were raised either in-house or by Thermo Fisher in two adult Sprague-Dawley rats (~300 g) using an 80-day protocol. Initially a pre-immune bleed of approximately 1 ml was performed on each rat. On the following day, rats were immunized with 100 µg of antigen in Complete Freund's Adjuvant. Booster injections were performed on days 21, 42, and 62 with 50 µg of emulsified peptide preparation in Incomplete Freund's Adjuvant. All immunizations were administered subcutaneously to the dorsum at four to six separate locations to minimize swelling and distress. On day 50, serum samples were collected and antibody titers determined by peptide specific ELISA. Samples with a titer in excess of 3200 were considered suitable for protection studies, and these animals were exsanguinated on day 80. Antisera from Thermo Fisher were shipped on dry ice. All antisera were stored frozen at −80° C. until protection studies were performed.

Rat Model of Hi Bacteremia and Passive Protection Assay

The rat model of bacteremia following intraperitoneal infection with *H. influenzae* was used to compare the abilities of antisera to protect against invasive disease as previously described [13-15]. Specified pathogen free (SPF), timed-pregnant Sprague-Dawley rats (Charles Rivers, Wilmington, Mass.) were received approximately five days prior to giving birth. These pregnant females were single housed on hardwood litter with ad *libitum* access to water and a standard pelleted food (Purina Lab Rodent Diet 5001). They were maintained on a 12 hour light-dark cycle in separate forced air cubicles in a bio-containment facility (ABSL2) to prevent cross-contamination. Newborn pups from different mothers were pooled and randomly reassigned to the mothers (n=10 pups per female).

In each experiment, cohorts of ten 4-day old infant rats were injected subcutaneously with 100 µl of either pre-immune serum, antiserum raised to a specific peptide, or PBS. The following day, each infant rat was challenged by intraperitoneal injection of approximately $1.5 \times 10^5$ CFU of R2866. Inocula were prepared as previously described [15], and the actual infective dosage was confirmed by quantitative plating. At 24 or 48 hours post-infection, blood samples (50 µl) were obtained from the anesthetized infant rats (gaseous isoflourane) by cardiac puncture. Bacterial titers were determined using a modified track-dilution method as previously described [15]. All plates were incubated at 37° C. for 24-48 hours to quantify CFU/ml. The Fisher Exact Test was used to determine the statistical significance of differences in the fraction of animals developing bacteremia in different infant rat cohorts. The Kruskal-Wallis test was used to determine the statistical significance of differences in the mean bacteremic titers between groups of infant rats. A P value <0.05 was taken as statistically significant.

Results

Immunological Examination of NTHi Peptides

Preliminary experiments were performed to gauge the likelihood that conserved SEPs represent protective epitopes. These experiments were initiated when the available sequenced *H. influenzae* genomes were limited. Five complete genomes were utilized in these studies and were the originally sequenced isolate Rd KW20, a sequenced type b isolate 10810, and three NTHi isolates (86-028NP, R2866, and R2846). The protein of interest in these studies was the heme-hemopexin utilization protein HxuC [16-17]. The HxuC protein sequences from the five genome-sequenced isolates, as well as several stand-alone HxuC protein sequences from additional strains, were used to perform sequence alignments. At the same time, a predicted molecular model was constructed, and the putative surface-exposed regions were determined. Peptide epitopes from 31 regions showing a high degree of sequence conservation were selected for immunological examination (Table 1).

In a screening experiment (FIG. 1), the five KLH-conjugated peptides were mixed to provide a pentavalent preparation that was used to immunize two adult rats as described. FIG. 1 depicts protection afforded by anti-HxuC antisera in the infant rat model of NTHi bacteremia. Panel A shows the percentage of infected infant rats pretreated with pentavalent anti-HxuC antisera with detectable bacteremia 48 hours after infection. Twenty-four hours prior to infection, cohorts of infant rats were pretreated with phosphate-buffered saline (PBS), pre-immune serum (PIS), or peptide-specific antiserum (PSAS). Fisher's exact test was used to compare percentages of bacteremic pups (P=0.0011 for PBS vs PSAS and P=0.0198 for PIS vs PSAS). Panel B shows the percentage of infected infant rats pretreated with antisera against specific HxuC peptides with detectable bacteremia 48 hours after infection. Fisher's exact test was used to compare percentages of bacteremic pups (P=0.0011 for PBS vs HxuC1 and P=0.0001 for PBS vs HxuC2). Panel C shows bacteremic titers in infected infant rats pretreated with antisera against specific HxuC peptides 48 hours after infection. Filled dots represent the bacteremic titer in each individual animal in a cohort. The unfilled dot represents the average bacteremic titers in all members of the cohort. Values of 1 or below represent animals with no detectable bacteremia. The Kruskal-Wallis test was used to compare bacteremic titers (means±SD) (P=0.002 for PBS vs HxuC1 and P=0.0004 for PBS vs HxuC2).

The results indicate that antisera raised to the pentavalent peptide preparation provided significant protection against NTHi bacteremia by comparison with both PBS control and pre-immune sera from the same animals (FIG. 1A). Having demonstrated that antisera raised to the pentavalent-peptide preparation were protective, each of the five HxuC-derived peptides was examined individually. Antisera specifically against two of the peptides (HxuC1-SEQ ID NO: 97, and HxuC2-SEQ ID NO:101) were highly protective (FIG. 1). All animals receiving antisera to HxuC2 failed to develop bacteremia, while in the cohort receiving HxuC1 antisera 2 of 10 infected animals developed bacteremia (FIG. 1B). In the two animals in the HxuC1-antisera treated group that developed bacteremia, the bacterial titers were approximately 1000-fold less than control animals (FIG. 1C). Antisera to the remaining three peptides from HxuC, HxuC3, HxuC4, and HxuC5 did not provide statistically significant protection against NTHi invasive disease. Since certain peptides derived from HxuC gave rise to protective antisera, the study was extended to include additional potentially surface-exposed proteins from *H. influenzae* (Table 1).

TABLE 1

Peptides (epitopes) used for polyclonal antisera production

| Protein[a] | Peptide Sequence[b] | SEQ ID NO: |
|---|---|---|
| HxuC-1 | LYNNKTIEKEQRKV (peptide no. 3a) | 97 |
| HxuC-2 | DHYDTSSKTVKYKD (peptide no. 5b) | 101 |
| HxuC-3 | APSMQERFVSGAHFG (peptide no. 6a) | 102 |
| HxuC-4 | KGKDKDSGEALSNIAASK (peptide no. 7b) | 104 |
| HxuC-5 | ENLFDRKYQPAFSLMEGTGRN (peptide no. 9a) | 109 |
| ComE-1 | TLNKDDG(V/I)YYLNGSQSGKGQ (peptide no. 1a and 1b) | 589 |
| Hel-1 | DNSPYAGWQVQNNKPFDGKD (peptide no. 1a) | 562 |
| Hel-2 | GDNLDDFGN(T/S)VYGKLNADRR (peptide no. 2a and 2b) | 590 |
| TdeA-1 | QRRVDISTNSA(I/T)SHK (peptide no. 1a and 1b) | 591 |
| OmpU-1 | SWDYQKSTSNHAFYRYDKNR (peptide no. 1a) | 275 |
| NTHi1140-1 | EQCVYPNLTRILQQHFSKEDSYIHSQYVFFYPLEKIIGEQYVKIIQ (peptide no. 1a) | 308 |
| Hap-1 | QDKRRYDSDAFRAYQQKTNLR (peptide no. 1a) | 123 |
| NlpI-2 | LNEQKLKPQEAQTNLVERAKGLSED (peptide no. 2a) | 139 |
| NTHi0353-1 | SVGDGIIAKDFTRDKSQNDFTSFVSGDYVWNVDSGL (no. 1a) | 128 |
| Lpp-1 | VTGCANTDIFSGDVYSASQAKEARSITYGTIV (peptide no. 1a) | 245 |
| TpsB-21 | GISKSGKLVGSIGEVFGIQDLNLGTSGVGDKSKVTVSGNIT (no. 21a) | 460 |
| Pal-1 | KVLVEGNTDERGTPEYNIALGQRRADAVKGYL (no. 1a) | 46 |
| Pal-2 | GKGVDAGKLGTVSYGEEKPAVLGHDEAAYSKNRRAVLAY (no. 2a) | 47 |
| BamA-2 | FALEYNRNLYIQSMKFKGNGIKTN (peptide no. 2a) | 327 |
| BamA-3 | GFGNKRLPFYQTYTAGGIGSLRGFAYGSIGPNAIY (no. 3a) | 328 |
| BamA-4 | IKKYENDDVEQF (peptide no. 4a) | 329 |
| Spr-1 | QLTGLINNLEKDNRTGIFHKVRTNRSSALMG (peptide no. 1a) | 205 |
| OmpE-2 | GLYVYPEPKRYARSVRQYKILNCANYHLTQ (peptide no. 2a) | 153 |
| MltF-1 | WQLAYRKNENRPKNLGNVKKDIYISNNLA (peptide no. 1a) | 130 |
| LppC-2 | CYYGLSPEDEAESAANKMWNDGVRNPL (peptide no. 2a) | 202 |
| LptE-2 | PILRINKQITSDQVASIFKHGREAEK (peptide no. 2a) | 321 |
| LptE-4 | EVIWNDMREQVARQLIVKIIALQNQIK (peptide no. 4a) | 325 |
| NucA-1 | TGSAMPGGSANRIPNKAGSNPEGSIA (peptide no. 1a) | 145 |
| OapB-1 | QKMQVEKVDKALQKGEADRYLCQDD (peptide no. 1a) | 57 |
| BamD-6 | QDALARMAYIKDALARHELEIAKFY (peptide no. 6a) | 164 |
| NlpB-4 | PLAIIQNSITKFDGERSLIVYPKQ (peptide no. 4a) | 122 |
| LolB-3 | DGSQWTADYLTYHSNNSMPENILL (peptide no. 3a) | 257 |
| PilF-1 | TISKQLSAVIFPFIFSACVSQS (peptide no. 1a) | 48 |
| MltC-2 | LVASRKDYVKYTDSFYTRSHVS (peptide no. 2a) | 350 |
| NTHi1387-3 | LYNDDYSVAVLDFLVNKIEQE (peptide no. 3a) | 268 |
| SmpA-1 | DVPQGNYLEATTVAQVKEGM (peptide no. 1a) | 341 |

TABLE 1-continued

Peptides (epitopes) used for polyclonal antisera production

| Protein[a] | Peptide Sequence[b] | SEQ ID NO: |
|---|---|---|
| HemR-4 | DNLFNRAYNPYLGELASGTGRN (peptide no. 4a) | 488 |
| Hup-1 | FYSTALDSGQSGGSSQF (peptide no. 1a) | 490 |
| Tbp-1 | HCSLYPNPSKNCRPTLDKPY (peptide no. 1a) | 517 |
| HgpC-1 | DGLRQAETLSSQGFKELFEGYGNFNNTRNSIE (no. 1a) | 537 |

[a]Annotated name of the protein in the NTHi isolates (suffix indicates peptide number).
[b]Amino acid sequence of the select peptide. Residues in parentheses represent variant residues at that single position.

Genome Sequencing of Genetically Characterized Diverse NTHi Isolates

At the time that the HxuC peptides were selected, the number of sequenced genomes was too low to confidently determine conservation across the NTHi of any single gene and insufficient to determine the breadth of variation of each individual surface-exposed loop. Currently, over 30 NTHi genome sequences are publicly available. However, only nine of these sequences are complete; the rest are partial sequences that are not closed or expertly annotated. The partial sequences are only useful to confirm the presence and sequence of a particular gene within the respective genome. However, since all genes may not be present, absence of a SEP in an inadequately annotated genome sequence cannot exclude it from further consideration as a core SEP. To assure that the peptide selection included regions found in all NTHi, the genomes of an additional 12 NTHi isolates were sequenced. To assure genetic diversity, isolates for sequencing were chosen from strains previously used to define the breadth of the species by electrophoretic typing [3], as well as other NTHi clinical isolates from the inventor's culture collection. A multi-locus sequence analysis system based on five gene loci (adk, pgi, recA, infB, and 16S rRNA) was applied to these newly sequenced genomes [18].

Figure 2:
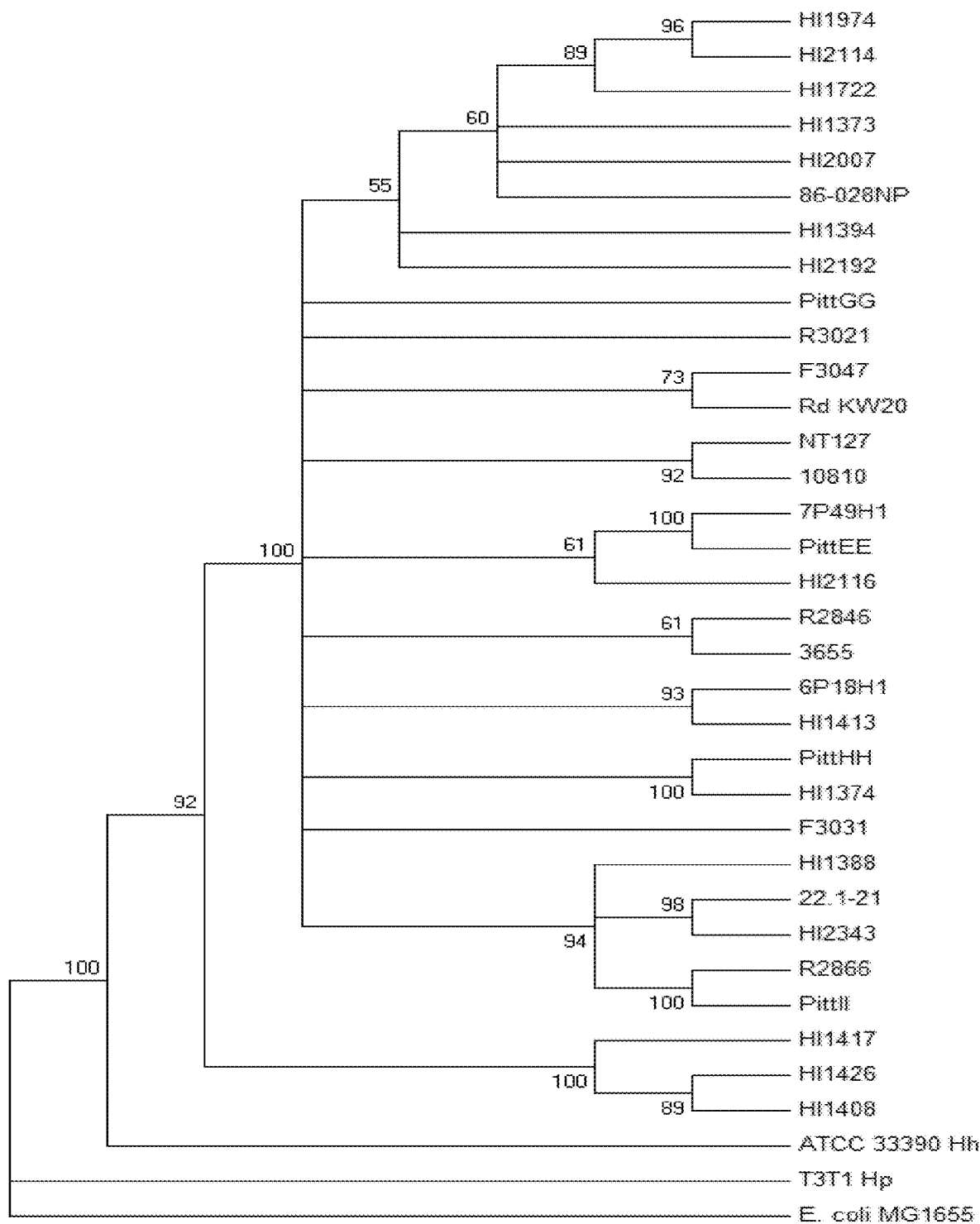
FIG. 2 depicts distribution of sequenced NTHi isolates using a neighbor joining dendogram of NTHi strains used in the present disclosure. The tree is rooted with *Escherichia coli* MG1655 and is based on sequence comparisons of the concatenated adk, pgi, recA, infB, and 16s rRNA gene sequences, with bootstrap values of greater than 50% of 1,000 bootstraps indicated. Also included are several non-NTHi sequences: Hp (*H. parainfluenzae* T3T1), HH (*H. haemolyticus* ATCC 33390), *H. influenzae* strain Rd KW20, and the *H. influenzae* type b strains F3031 and 10810.

Using these concatenated sequences from all the sequenced NTHi, a dendrogram was constructed to demonstrate the distribution of the newly sequenced isolates within the species (FIG. 2).

Identification of Core SEPs Present in the *H. influenzae*

Initially the complement of putative SEPs were identified in the NTHi strain 86-028NP. Such proteins were identified based on known annotation, the presence of export signal sequences, and their similarity to known OMPs in other species. Each coding region was analyzed using PSORTb and PSORT [19]. Proteins with localization signals indicating export across the cytoplasmic membrane were analyzed for homology to experimentally determined OMPs from other organisms. Finally, those proteins in which localization to the OM was putative were further subjected to analysis for structural motifs indicative of membrane-spanning domains. Ninety-six SEPs were identified in strain 86-028NP. This data set was then used to establish the presence of each allele in each of the 21 complete NTHi genome sequences. From these 21 complete sequences, a set of 62 NTHi core SEPs was identified (Table 2). Using all of the available genome and stand-alone gene sequences, the sequence conservation of each individual OMP gene was determined.

TABLE 2

Core Surface-Exposed Proteins of the Hi[a]

| 86-026NP locus | Gene designation | Rd KW20 locus | Gene description | Probable Type[b] |
|---|---|---|---|---|
| NTHI0579 | ytfL | HI0452 | Putative hemolysin (probable inner membrane) | α-helix |
| NTHI0576 | | HI0449 | Conserved hypothetical protein | Amorphous |
| NTHI0560 | comE | HI0435 | Outer membrane secretin ComE | Amorphous |
| NTHI0522 | ompP1 | HI0401 | Outer membrane protein P1 | β-barrel |
| NTHI0509 | yeaY | HI0389 | Slp family OM lipoprotein | Amorphous |
| NTHI0501 | pal | HI0381 | Peptidoglycan associated OMP | Amorphous |
| NTHI0486 | pilF | HI0366 | Transformation and Tfp-related protein PilF | Amorphous |
| NTHI0449 | oapB | HI0331 | Opacity associated adhesion protein B | Amorphous |
| NTHI0448 | oapA | HI0330 | Opacity associated adhesion protein A | α-helix |
| NTHI0409 | pilA | HI0299 | Type II secretory pathway, major prepilin PilA | Amorphous |
| NTHI0370 | hxuB | HI0263 | Heme-hemopexin utilization protein B | β-barrel |
| NTHI0369 | hxuC | HI0262 | Heme-hemopexin utilization protein C | β-barrel |
| NTHI0363 | nlpB | HI0256 | OMP assembly complex subunit NlpB/BamC | Amorphous |
| NTHI0354 | hap | HI0247 | Adhesion and penetration protein precursor | β-barrel |
| NTHI0353 | | HI0246 | Putative lipoprotein | Amorphous |
| NTHI0338 | mltF | HI0232 | Membrane-bound lytic murein transglycosylase F | Amorphous |
| NTHI0335 | nlpI | HI0230 | Lipoprotein NlpI | Amorphous |
| NTHI0303 | nucA | HI0206 | 5'-nucleotidase NucA | Amorphous |
| NTHI0267 | ompE | HI0178 | Adhesin protein E | Amorphous |
| NTHI0266 | bamD | HI0177 | OMP assembly complex subunit BamD | Amorphous |
| NTHI0252 | yajG | HI0162 | Putative lipoprotein | Amorphous |
| NTHI0225 | ompP2 | HI0139 | Outermembrane protein P2 | β-barrel |
| NTHI0220 | | HI0134 | Putative OMP assembly protein | β-barrel |
| NTHI0205 | mltA | HI0117 | Membrane-bound lytic murein transglycosylase A | Amorphous |

TABLE 2-continued

Core Surface-Exposed Proteins of the Hi[a]

| 86-026NP locus | Gene designation | Rd KW20 locus | Gene description | Probable Type[b] |
|---|---|---|---|---|
| NTHI0202 | hemR | HI0113 | Probable TonB-dependent heme receptor | β-barrel |
| NTHI1987 | yccT | HI1681 | Conserved hypothetical protein | Amorphous |
| NTHI1960 | yraP | NA | Lipoprotein YraP | Amorphous |
| NTHI1957 | lppC | HI1655 | Lipoprotein LppC | Amorphous |
| NTHI1954 | spr | HI1652 | Lipoprotein Spr, probable murein endopeptidase | Amorphous |
| NTHI1930 | | HI1236m | Conserved hypothetical protein | β-barrel |
| NTHI1627 | nlpC | HI1314 | Lipoprotein NlpC | Amorphous |
| NTHI1668 | tdeA | HI1462 | Outer membrane efflux porin TdeA | β-barrel |
| NTHI1794m | | HI1369 | Probable TonB-dependent transporter | β-barrel |
| NTHI1473 | lpp | HI1579 | 15 kDa peptidoglycan-associated lipoprotein | α-helix |
| NTHI1437 | ygiM | HI1605 | Conserved hypothetical protein | β-barrel |
| NTHI1435 | lolB | HI1607 | OM lipoprotein insertion protein LolB | Amorphous |
| NTHI1390 | hup | HI1217 | Heme utilization protein | β-barrel |
| NTHI1387 | | HI1215 | Conserved hypothetical protein | Amorphous |
| NTHI1342 | olpA1 | HI1174m | Probable surface adhesion OlpA1 | β-barrel |
| NTHI1332 | ompP5 | HI1164 | Outer membrane protein OmpP5 | β-barrel |
| NTHI1262 | | HI1098m | Conserved hypothetical protein | Amorphous |
| NTHI1171 | ompU | HI0997m | Putative OM protein OmpU | β-barrel |
| NTHI1169 | tbp2 | HI0995 | Transferrin binding protein 2 | Amorphous |
| NTHI1168 | tbp1 | HI0994 | Transferrin binding protein 1 | β-barrel |
| NTHI1164 | igA1 | HI0990 | IgA1 protease | β-barrel |
| NTHI1140 | | HI0966 | Conserved hypothetical protein | β-barrel |
| NTHI1133 | ycfL | HI0960 | Putative lipoprotein YcfL | Amorphous |
| NTHI1101 | | HI0930 | Putative lipoprotein | Amorphous |
| NTHI1091 | lptE | HI0922 | LPS assembly OM complex LptDE component | β-barrel |
| NTHI1084 | bamA | HI0917 | OM protein assembly factor BamA | β-barrel |
| NTHI1083 | skp | HI0916 | Chaperone Skp (Omp26) | Amorphous |
| NTHI1005 | smpA | HI0838 | omp assembly complex subunit SmpA/BamE | Amorphous |
| NTHI0921 | mltC | HI0761 | Membrane bound-lytic murein transglycosylase C | Amorphous |
| NTHI0915 | envC | HI0756 | Putative membrane-bound metalloprotease | Amorphous |
| NTHI0889 | lptD | HI0730 | LPS assembly OM complex LptDE, protein LptD | β-barrel |
| NTHI0849 | mlaA | HI0718 | Outer membrane lipid asymmetry protein MlaA | α-helix |
| NTHI0840m | hgpC | HI0712 | Hemoglobin-haptoglobin utilization protein C | β-barrel |
| NTHI0830 | lppB | HI0706 | OM antigenic lipoprotein B (NlpD) | Amorphous |
| NTHI0821 | tpsA | HI0698 | Probable 2 partner secretion system TamA homolog | β-barrel |
| NTHI0820 | tpsB | HI0696 | secretion system β-helical exported protein | β-helix |
| NTHI0816 | hel | HI0693 | Outer membrane protein P4 | Amorphous |
| NTHI0811 | glpQ | HI0689 | Glycerophosphodiesterase | Amorphous |
| NTHI0782 | hgpB | HI0661 | Hemoglobin-haptoglobin utilization protein B | β-barrel |

[a]Proteins were initially identified as putative members of the OMP complement using PSORT and PSORTb analysis of cellular localization of predicted protein sequences and/or due to homology to known OMP localized proteins. Lists were narrowed by excluding OMPs not conserved across the sequenced NTHi isolates and removal of proteins that lacked a strong probability of being localized to the outer membrane and having surface exposed residues.
[b]Probable structure based on modeling. PRED-TMBB and BOMP (β-barrel), TMHMM (α-helix), amorphous for proteins that fit neither model or have components of both.

Molecular Modeling to Assess Surface-Exposed Regions of the SEPs

The presently disclosed SEPs fall into three main structural categories: β-barrel, α-helix, and amorphous. The majority of OMPs that are embedded in the membrane adopt the β-barrel structure, while the remaining OMPs have an α-helix based structure. The OMPs that are either secreted or bound to the outer membrane by a small lipophilic tail are more amorphous, often with no clearly defined common structural features. The inventor's previous studies focused on HxuC, a defined OMP with the β-barrel conformation. In the outer membrane, such proteins fold to create a barrel-like structure with a core, or plug, which can be shifted to allow ingress of a transported molecule [20,21]. Referred to as "gated porins," these OMPs have been the focus of numerous X-ray crystallization studies. Since they are structurally constrained, it is possible to both map the NTHi OMPs to those with known crystal structure and to use computer assisted molecular modeling algorithms to determine the potential externally-exposed loops. In some cases, an external loop is small, comprising one or two residues, while other loops are longer and show variable degrees of sequence heterogeneity. A structure of one such NTHi conserved OMP (NTHI1794m in strain 86-028NP) has been proposed to demonstrate the topography and location of the OM loops. A Loop 3 is relatively conserved and satisfies the criteria for selection as a suitable peptide motif for generation of antisera. Similarly, the OMPs determined to have the α-helix conformation were mapped where possible to the conserved residues of OMPs in other species that have deduced crystal structures. OMPs which are loosely attached to the membrane have proven more difficult to map. To determine potentially exposed regions on these OMPs, numerous molecular prediction algorithms were utilized to identify potential transmembrane and exposed residues. These are usually based on hydrophobicity/hydrophilicity plots and periodicity of residues in these regions. Of the 62 core OMPs, 25 appear to have the β-barrel structure and four the α-helix structure, while the remaining OMPs appear to be amorphous structures anchored to the membrane by a polypeptide tail. To date, 46 of the core OMPs have been sufficiently modeled to identify surface exposed peptide motifs. These include 16 of the β-barrels, 2 of the α-helical proteins, and 23 of the amorphous structures (Table 2). Combining putative structure with the sequence alignments allows identification of conserved, putatively surface exposed regions. Tables 1, 3, and 4 show non-limiting examples of NTHi protein epitopes which can be used as peptides in immunogenic formulations of the present disclosure. Approximately 100 of the epitopes shown in Table 4 have 100% conservation among the OMPs.

Characterization of Protective Epitopes

In a subsequent experiment, from the sequence alignments, 5 external OM loops that showed conservation and that were a minimum of 10 amino acid residues in length were selected. The 5 selected epitopes were in addition to the 5 from HxuC peptides examined above (Table 1). The 5 additional epitopes were from 4 different proteins ComE, Hel, TdeA, and OmpU and were designated, respectively, ComE1, Hel1, Hel2, TdeA1, and OmpU1 (Table 2).

Figure 3:
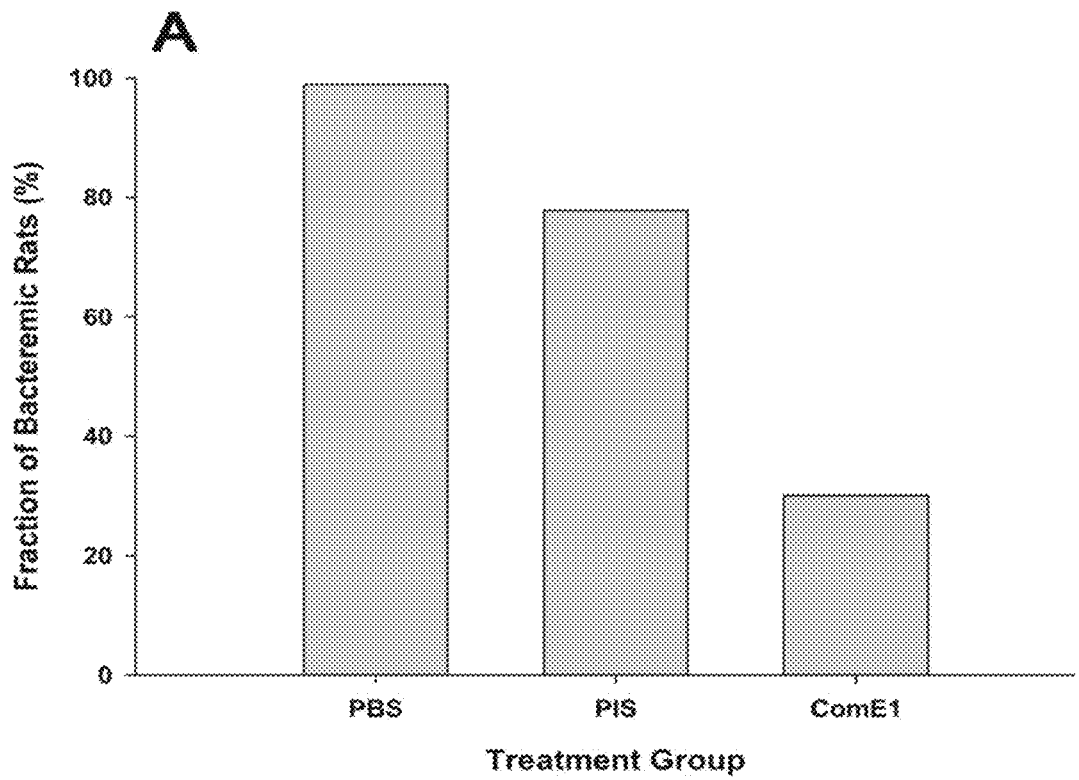
FIG. 3 depicts protection afforded by antisera raised against ComE and Hel derived peptides in the infant rat model of NTHi bacteremia. (A) Percentage of infected infant rats pretreated with anti-ComE1 antiserum with detectable bacteremia 24 hours after infection. (B) Bacteremic titers in infant rats pretreated with anti-ComE1 antisera 24 hours after infection. (C) Percentage of infected rats pre-treated with anti-Hel1 antisera with detectable bacteremia 24 hours after infection. (D) Bacteremic titers in infant rats pretreated with anti-Hel1 antiserum with detectable bacteremia 24 hours after infection.
Figure 3:
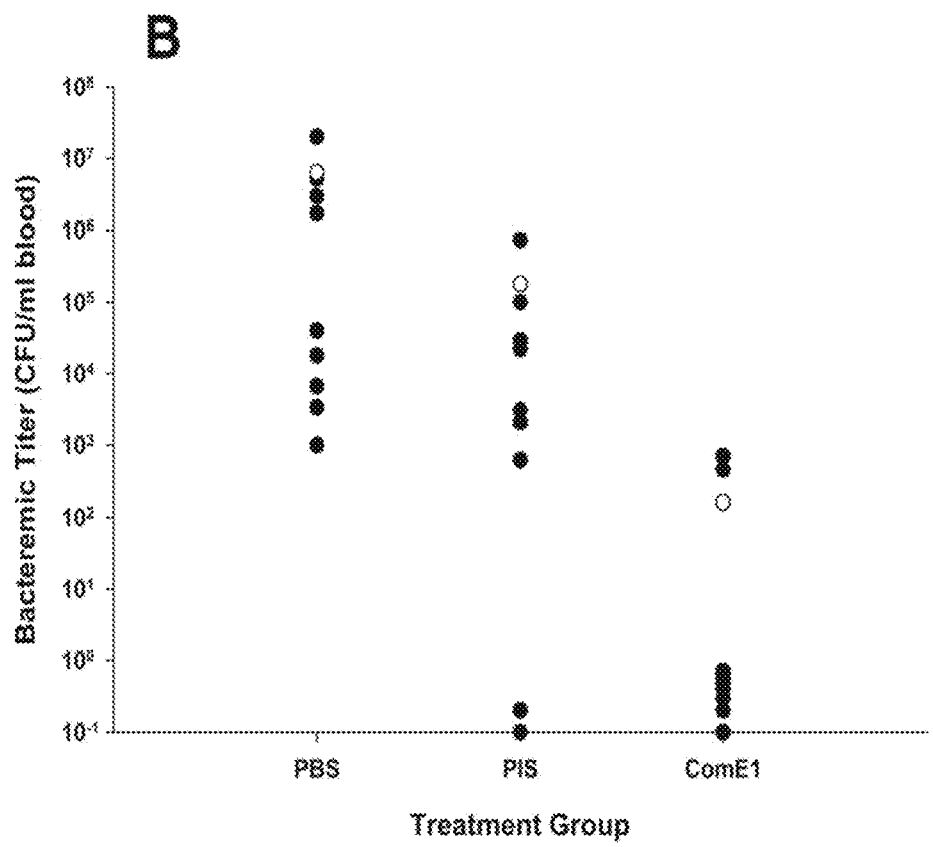
Figure 3:
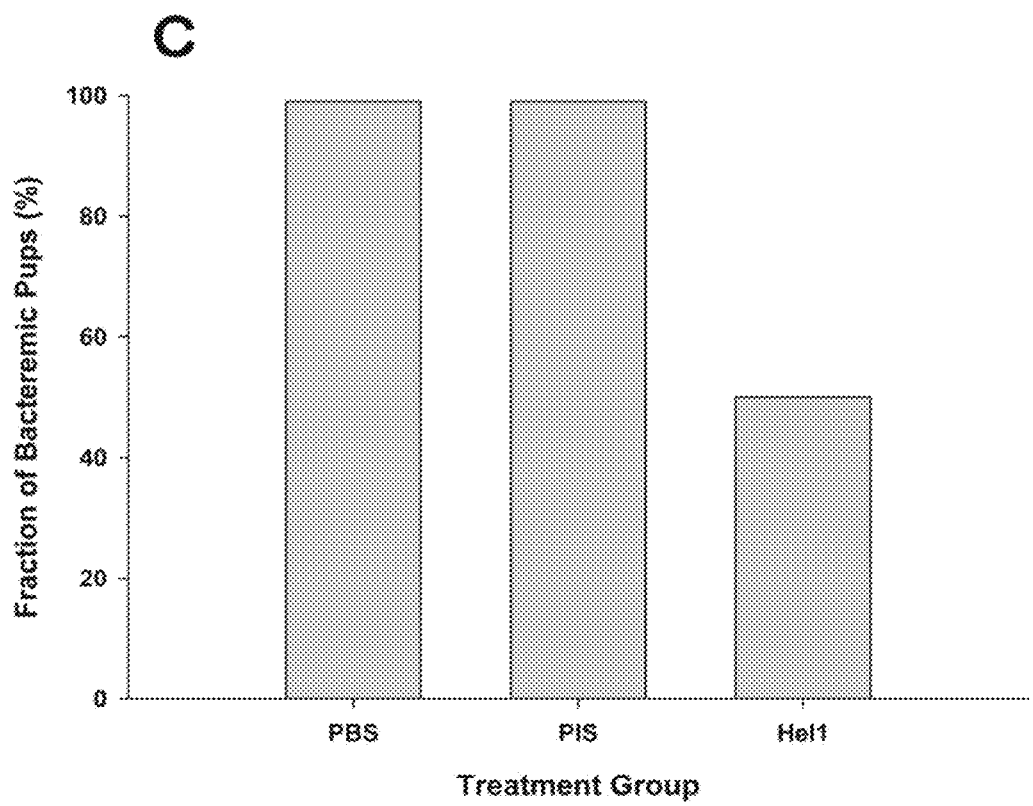
Figure 3:
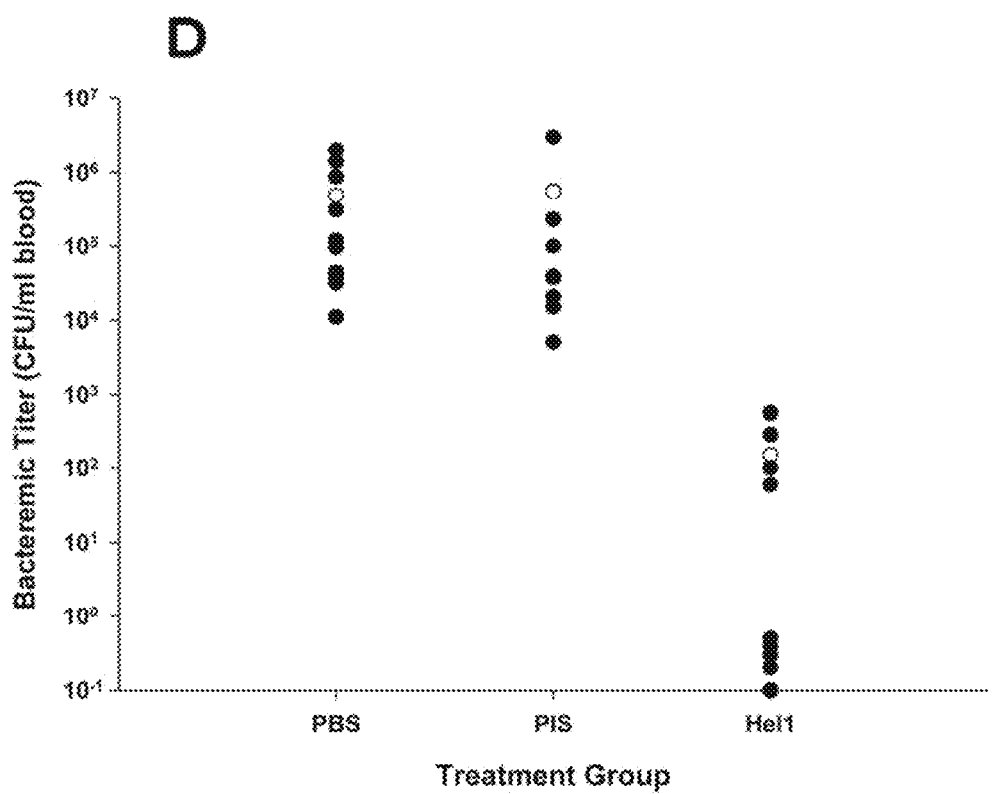

Each of these five epitopes was used in the immunization protocol described herein. The results in FIG. 3 depict protection afforded by antisera raised against ComE and Hel derived peptides in the infant rat model of NTHi bacteremia. Panel A shows the percentage of infected infant rats pre-treated with anti-ComE1 antiserum with detectable bacteremia 24 hours after infection. Twenty-four hours prior to infection, cohorts of infant rats were pretreated with phosphate-buffered saline (PBS), pre-immune serum (PIS), or anti-ComE1 antiserum (ComE1). Fisher's exact test was used to compare percentages of bacteremic pups (P=0.0031 for PBS vs ComE1 and P=0.0698 for PIS vs ComE1). Panel B shows bacteremic titers in infant rats pretreated with anti-ComE1 antisera 24 hours after infection. Filled dots represent the bacteremic titer in each individual animal in a cohort. Each unfilled dot represents the average bacteremic titers in all members of the cohort. Values of 1 or below represent animals with no detectable bacteremia. The Kruskal-Wallis test was used to compare bacteremic titers (mean±SD) (P=0.07 for PBS vs PIS, P=0.0002 for PBS vs ComE1 and P=0.01 for PIS vs ComE1). Panel C shows the percentage of infected rats pre-treated with anti-Hel1 anti-sera with detectable bacteremia 24 hours after infection. Twenty-four hours prior to infection, cohorts of infant rats were pretreated with phosphate-buffered saline (PBS), pre-immune serum (PIS), or anti-Hel1 antiserum (Hel1). Fisher's exact test was used to compare percentages of bacteremic pups (P=0.0325 for both PBS vs Hel1 and PIS vs Hel1). Panel D shows the bacteremic titers in infant rats pretreated with anti-Hel1 antiserum with detectable bacteremia 24 hours after infection. Filled dots represent the bacteremic titer in each individual animal in a cohort. Each unfilled dot represents the average bacteremic titers in all members of the cohort. Values of 1 or below represent animals with no detectable bacteremia. The Kruskal-Wallis test was used to compare bacteremic titers (mean±SD) (P=0.15 for PBS vs PIS, P=0.0003 for PBS vs Hel1 and P=0.0005 for PIS vs Hel1).

The TdeA1 peptide did not induce an antibody titer sufficient (absent further purification) to proceed with further study of that antigen. Antisera raised to the OmpU1 peptide also did not appear to provide a significant protective effect in the infant rat model. Seven of 10 infant rats pretreated with antiserum raised to ComE1 failed to develop bacteremia (FIG. 3A). While the rate of bacteremia of the anti-ComE1 treated group was significantly lower than the rate for the PBS treated group (P=0.0031), it did not significantly differ from the pre-immune serum treated group (P=0.0698), probably due to a small cohort size in the latter group (FIG. 3A). However, the bacteremic titer in the anti-ComE1 antiserum cohort was significantly lower than that seen in either of the control groups (FIG. 3B). Antiserum raised to the Hel1 was significantly protective when given to infant rats 24 hours prior to challenge with NTHi strain R2866. While all rats pretreated with either PBS or the pre-immune serum had detectable bacteremia 24 hours after infection 5 of 10 animals pretreated with anti-Hel1 antiserum were abacteremic (P=0.0325) (FIG. 3C). Bacteremic titers were also significantly lower in those rats pretreated with anti-Hel1 antiserum than those rats pretreated with either PBS or pre-immune serum (FIG. 3D). Antiserum raised to the Hel2 peptide gave similar results to those seen for Hel1 (data not shown).

In all, the passive protection by sera produced from the forty different peptide sequences in Table 1 was evaluated using the passive protection assay described above. Of the 40 epitopes evaluated, antisera raised against 20 of the 40 peptides provided significant protection in infant rats challenged with NTHi strain 82866 (Table 3).

TABLE 3

Peptide sequences (epitopes) producing polyclonal antisera that protected infant rats challenged with NTHi strain R2866.

| Protein[a] | Peptide Sequence[b] | SEQ ID NO: |
|---|---|---|
| HxuC-1 | LYNNKTIEKEQRKV (peptide no. 3a) | 97 |
| HxuC-2 | DHYDTSSKTVKYKD (peptide no. 5b) | 101 |
| ComE-1 | TLNKDDG(V/I)YYLNGSQSGKGQ (peptide no. 1a and 1b) | 589 |
| Hel-1 | DNSPYAGWQVQNNKPFDGKD (peptide no. 1a) | 562 |
| Hel-2 | GDNLDDFGN(T/S)VYGKLNADRR (peptide no. 2a and 2b) | 590 |
| NTHi1140-1 | EQCVYPNLTRILQQHFSKEDSYIHSQYVFFYPLEKIIGEQYVKIIQ (peptide no. 1a) | 308 |
| Hap-1 | QDKRRYDSDAFRAYQQKTNLR (peptide no. 1a) | 123 |
| NlpI-2 | LNEQKLKPQEAQTNLVERAKGLSED (peptide no. 2a) | 139 |
| Lpp-1 | VTGCANTDIFSGDVYSASQAKEARSITYGTIV (peptide no. 1a) | 245 |
| TpsB-21 | GISKSGKLVGSIGEVFGIQDLNLGTSGVGDKSKVTVSGNIT (no. 21a) | 460 |
| BamA-3 | GFGNKRLPFYQTYTAGGIGSLRGFAYGSIGPNAIY (no. 3a) | 328 |

TABLE 3-continued

Peptide sequences (epitopes) producing polyclonal antisera that protected infant rats challenged with NTHi strain R2866.

| Protein[a] | Peptide Sequence[b] | SEQ ID NO: |
|---|---|---|
| BamA-4 | IKKYENDDVEQF (peptide no. 4a) | 329 |
| OmpE-2 | GLYVYPEPKRYARSVRQYKILNCANYHLTQ (peptide no. 2a) | 153 |
| LptE-2 | PILRINKQITSDQVASIFKHGREAEK (peptide no. 2a) | 321 |
| LptE-4 | EVIWNDMREQVARQLIVKIIALQNQIK (peptide no. 4a) | 325 |
| NucA-1 | TGSAMPGGSANRIPNKAGSNPEGSIA (peptide no. 1a) | 145 |
| MltC-2 | LVASRKDYVKYTDSFYTRSHVS (peptide no. 2a) | 350 |
| NTHi1387-3 | LYNDDYSVAVLDFLVNKIEQE (peptide no. 3a) | 268 |
| SmpA-1 | DVPQGNYLEATTVAQVKEGM (peptide no. 1a) | 341 |
| Tbp-1 | HCSLYPNPSKNCRPTLDKPY (peptide no. 1a) | 517 |

[a] Annotated name of the protein in the NTHi isolates (suffix indicates peptide number).
[b] Amino acid sequence of the select peptide. Residues in parentheses represent variant residues at that single position.
Protection was determined in passive protection assays in the infant-rat model of NTHi bacteremia (See FIGS. 1 and 4 for examples of data). Protection is based on the percentage of animals in the antisera-treated cohort with no detectable bacteremia 24-hours following infection compared to the pre-immune antisera and PBS-treated cohorts Yes, $P < 0.05$; No, $P > 0.05$ Ultimately, 591 peptide epitopes (SEQ ID NO:1-SEQ ID NO:591) were evaluated for sequence conservation across multiple NTHi genomes (Table 4).

TABLE 4

Eptiopes of Nontypeable Haemophilus influenzae (NTHi)

| Protein[a] | Peptide No. | Peptide Sequence | SEQ ID NO |
|---|---|---|---|
| ComE | 1a | TLNKDDGVYYLNGSQSGKGQ | 1 |
| | 1b | TLNKDDGIYYLNGSQSGKGQ | 2 |
| | 1c | LTLNKDDGVYYLNGSQSGKGQVAGNLTTNEPHL | 3 |
| | 1d | LTLNKDEGIYYLNGGQSGKGQVAGNLATNEPHL | 4 |
| | 1e | LTLNKDEGIYYLNGGQSGKGQVAGNLTTNEPHL | 5 |
| | 1f | LTLNKDEGIYYLNGGLSGKGQVAGNLTTNEPHL | 6 |
| | 1g | LTLNKDEGIYYLNGGLSGKEQVAGNLTTNEPHL | 7 |
| | 1h | LTLNKDEGIYYLNCSQSGKGQVAGNLTTNEPHL | 8 |
| | 2a | NPKTDNECFFIRLSQAPLA | 9 |
| | 2b | NPKTDNERFFIRLSQAPLA | 10 |
| | 3a | TTGSGSLLSPDGSITFDDRSNLLVIQDEPR | 11 |
| | 3b | TTGSGSLLSPAGSITFDDRSNLLVIQDEPR | 12 |
| | 3c | TTGSGSLLSPVGSITFDDRSNLLVIQDEPR | 13 |
| | 3d | TTGSGSLLSSAGSITFDDRSNLLVIQDEPR | 14 |
| OmpP1 | 1a | GSASQRNVVPG | 15 |
| | 1b | GSASERNVVPG | 16 |
| | 1c | GSASARNVVPG | 17 |
| | 1d | GSASQRNVIPG | 18 |
| | 2a | EYDDSYDAGIFGGK | 19 |
| | 2b | KYDDSYDAGIFGGK | 20 |
| | 2c | KYDDSYDAGVFGGK | 21 |
| | 2d | EYGDSYNAGIFGGK | 22 |
| | 2e | EYGDSYNAGVFGGK | 23 |
| | 3a | SKDKSVVSLQDRA | 24 |
| | 3b | SQDKSVVSLQDRA | 25 |
| | 3c | SKDTSVVSLQDRA | 26 |
| | 3d | SKDKSVVSLQDKA | 27 |
| | 3e | SKDTSVVSLQDSA | 28 |
| | 4a | KVDIDFTDRTATS | 29 |
| | 4b | KVDIDFTDRTASS | 30 |
| | 4c | KVDIDFADRTATS | 31 |
| | 5a | WSRLTKLHASFEDGKKAFDKELQYS | 32 |
| | 5b | WSRLTKLNASFEDGKKAFDKELQYS | 33 |
| | 5c | WSRLTKLHASFENGKKAFDKELQYS | 34 |
| | 5d | WSRLTRLYASSENGKKAFDKELQYS | 35 |
| | 5e | WSRLTKLNANFEDGKKAFDKELQYS | 36 |

TABLE 4-continued

Epitopes of Nontypeable Haemophilus influenzae (NTHi)

| Protein<sub>a</sub> | Peptide No. | Peptide Sequence | SEQ ID NO |
|---|---|---|---|
| | 5f | WSRLTKLHASYENGEKAFDKELQYS | 37 |
| | 5g | WSRLTKLHASFEDGKKAFEKELQYS | 38 |
| | 6a | DQAASRHHRSAAIPDTDRT | 39 |
| | 6b | DQAASRHQRSAAIPDTDRT | 40 |
| | 6c | DQAASRHQRSAAIPDTNRT | 41 |
| | 7a | TTANYTSQAHA | 42 |
| | 7b | STANYTSQAHA | 43 |
| | 7c | ATANYTSQAHA | 44 |
| | 7d | TNANYTSQAHA | 45 |
| Pal | 1a | KVLVEGNTDERGTPEYNIALGQRRADAVKGYL | 46 |
| | 2a | GKGVDAGKLGTVSYGEEKPAVLGHDEAAYSKNRRAVLAY | 47 |
| PilF | 1a | TISKQLSAVIFPPFIFSACVSQS | 48 |
| | 2a | LSYLQQNNPQLAKINLDKALQHDKNYYLVHS | 49 |
| | 2b | LSYLQQNNPQLAKINLDKALLHDKNYYLVHS | 50 |
| | 2c | LSYLQQNNPQLAKINLDNALQHDKNYYLVHS | 51 |
| | 3a | REYEIAVKLNHKQGDVHNNFGTFLCSQKKFEQAQQQ | 52 |
| | 3b | REYEIAVNLNHKQGDVHNNFGTFLCSQKKFEQAQQQ | 53 |
| | 3c | REYEIAVNLNYKQGDVHNNFGTFLCSQKKFEQAQQQ | 54 |
| | 4a | MDIYQQTLEKLRQIDGKRAEKFNSLK | 55 |
| | 4b | MDIYQQTLEKLRQINGKRAEKFNSLK | 56 |
| OapB | 1a | QKMQVEKVDKALQKGEADRYLCQDD | 57 |
| | 2a | SEKLTLMISERGKNYANIRWMWQERDDFSTLKTNLGE | 58 |
| | 2b | SEKLTLMISERGKNYANIRWMWQERDDFSMLKTNLGE | 59 |
| OapA | 1a | QTNFQQRKEPTFG | 60 |
| | 2a | TEENISAVDEEI | 61 |
| | 3a | VEKAEKPILAQPEKWK | 62 |
| | 4a | LPAKHRRLFM | 63 |
| | 5a | VLVILLIIFFALKPSSDTVESFTQSNSNE | 64 |
| | 6a | FRDNQLNISDVNAMSKA | 65 |
| | 7a | GAGNVLSSFKSGDKVTVSVNNQGRVNEMRLSN | 66 |
| | 7b | GAGNVLSNFKSGDKVTVSVNNQGRVNEMRLSN | 67 |
| PilA | 1a | VSELLQASAPYKADVELCVYST | 68 |
| | 1b | VSELLQASAPYKSDVELCVYST | 69 |
| HxuB | 1a | NQGNKYTGRY | 70 |
| | 2a | TANYLDYKLGGNFKSLQSQ | 71 |
| | 2b | TANYLHYKLGGNFKSLQSQ | 72 |
| | 3a | QQAVYAKQKRK | 73 |
| | 3b | QQAVNVKQKRK | 74 |
| | 3c | QQAVYVKQKRK | 75 |
| | 3d | QQAVTVKQKRK | 76 |
| | 3e | QQAVSVKQKRK | 77 |
| | 3f | QQAATAKQKRK | 78 |
| | 3g | QQAVDAKQKRK | 79 |
| | 4a | GNLANQTSEK | 80 |
| | 4b | GNLANQTNEK | 81 |
| | 4c | GNLANQTSEQ | 82 |
| | 4d | GNLANQTNEQ | 83 |
| | 4e | GNLANQTNET | 84 |
| | 4f | GNLANQTNER | 85 |
| | 5a | QFADKTLESSQKMLLGGLS | 86 |
| | 5b | QFADKNLESSQKTLLGGLS | 87 |
| | 5c | QFADKNLESSQKMLLGGLS | 88 |
| | 6a | KPLDNNINNADKHQ | 89 |
| | 6b | KPLDNNIDNADKHQ | 90 |
| | 6c | KPLDNNIDNTDKHQ | 91 |
| HxuC | 1a | DNLRTGKGNK | 92 |
| | 1b | DNLRIGKGNK | 93 |
| | 2a | KQTAPSNNEVEVELTWEQI | 94 |
| | 2b | KQTAPSNNEVEVELTWEKI | 95 |
| | 2c | KQTAPGNNEAKVELTWEQI | 96 |
| | 3a | LYNNKTIEKEQRKV | 97 |
| | 4a | DAKFRADPYNANS | 98 |
| | 4b | DAKFRAEPYNANS | 99 |
| | 5a | DTSSKTVKYKD | 100 |
| | 5b | DHYDTSSKTVKYKD | 101 |
| | 6a | APSMQERFVSGAHFG | 102 |
| | 7a | DKDSGEALSNIAAS | 103 |
| | 7b | KGKDKDSGEALSNIAASK | 104 |

TABLE 4-continued

Eptiopes of Nontypeable Haemophilus influenzae (NTHi)

| Protein[a] | Peptide No. | Peptide Sequence | SEQ ID NO |
|---|---|---|---|
| | 7c | KGRDKDSGEALSNIAASK | 105 |
| | 8a | RVPKDHSVTYPSY | 106 |
| | 8b | RVPKDHAVTYPSY | 107 |
| | 8c | RVPKDHGVTYPSY | 108 |
| | 9a | ENLFDRKYQPAFSLMEGTGRN | 109 |
| | 9b | ENLFDRKYQPAFSLIEGTGRN | 110 |
| NlpB | 1a | MRRDGIIFTPNVSDKQYYTSERLNRIV | 111 |
| | 1b | MRRDGIIFTPNISDKQYYTSERLNRIV | 112 |
| | 2a | GCSSNPETLKASNDSFQKSEASIPHFSPLATGGVQ | 113 |
| | 2b | GCSSNPETLKATNDSFQKSEASIPHFSPLATGGVQ | 114 |
| | 2c | GCSSNPETLKATNDSFQKSETSIPHFSPLATGGVQ | 115 |
| | 2d | GCSSNPETLKATNDSFQKSETNIPHFSPLATGGVQ | 116 |
| | 2e | GCSSNPETLKATNDSFQKSETSIPHFSPLATGGVQ | 117 |
| | 3a | LPKADDAYSLPNIEVKKRGDIDIR | 118 |
| | 3b | LSKADDAYSLPNIEVKKRGDIDIR | 119 |
| | 3c | LPKADNAYSLPNIEVKKRGDIDIR | 120 |
| | 3d | LPKADDSYSLPNIEVKKRGDIDIR | 121 |
| | 4a | PLAIIQNSITKFDGERSLIVYPKQ | 122 |
| Hap | 1a | QDKRRYDSDAFRAYQQKTNLR | 123 |
| | 1b | QDKRRYDSDAFRAYQQKANLR | 124 |
| | 2a | VDVSNANVQTTVN | 125 |
| | 3a | LQQSFGRYW | 126 |
| | 3b | LQQPFGRYW | 127 |
| NTHI0353 | 1a | SVGDGIIAKDFTRDKSQNDFTSFVSGDYVWNVDSGL | 128 |
| | 1b | SVGDGIIAKDFIRDKSQNDFTSFVSGDYVWNVDSGL | 129 |
| MltF | 1a | WQLAYRKNENRPKNLGNVKKDIYISNNLA | 130 |
| | 2a | SIVNYHRVQENQTTNDNTNNESAVKNLEE | 131 |
| | 2b | SIVNYHRVQENQTTNDNANNESAVKNLEE | 132 |
| | 2c | SIVNYHRVQENQIINDNASNESAVKNLEE | 133 |
| | 2d | SIVNYHRVQENQTINDNASNESAVKNLEE | 134 |
| NlpI | 1a | ELDSGYDYTHLNRGLNFYYVGRYHLA | 135 |
| | 1b | ELDSSYDYTHLNRGLNFYYVGRYHLA | 136 |
| | 1c | ELDSGYDYTHLNRGLNFYYVGHYHLA | 137 |
| | 1d | ELDSGYDYTHLNRGLNFYYVGRYPLA | 138 |
| | 2a | LNEQKLKPQEAQTNLVERAKGLSED | 139 |
| | 3a | LQQRASEFAENSQQYA | 140 |
| | 3b | LQQRANGFAENSQQYA | 141 |
| | 4a | ILTETYFYLAKQKLNVGL | 142 |
| | 5a | VDEAAALFKLAMANQ | 143 |
| | 5b | VEYRFAAFELMKLK | 144 |
| NucA | 1a | TGSAMPGGSANRIPNKAGSNPEGSIA | 145 |
| | 2a | YVAGGKDGYKTFGKLFNDPKYEGVD | 146 |
| | 2b | YVAGGKDGYKTFGKLFNDPKYEGID | 147 |
| | 3a | LPDAESFIKFMKKHPHFEAY | 148 |
| OmpE | 1a | SGYIRLVKNVNYYIDSESIWDNQEPQIVHFD | 149 |
| | 1b | SGYVRLVKNVNYYIDSESIWDNQEPQIVHFD | 150 |
| | 1c | SGYIRLVKNVNYYIDSESIVDNQEPQIVHFD | 151 |
| | 1d | SGYIRLVKNVNYYIDSESIWDNQESQIVHFD | 152 |
| | 2a | GLYVYPEPKRYARSVRQYKILNCANYHLTQ | 153 |
| | 3a | DFYDEFWGQGLRAAPKKQKHTLSLTPDTTLYNAAQIICANYG | 154 |
| | 3b | DFYDEFWGQGLRAAPKKKHTLSLIPDTTLYNAAQIICANYG | 155 |
| BamD | 1a | ASVNELYTKGTTSLQEGS | 156 |
| | 2a | YSEAIRYLKATTERFPGS | 157 |
| | 2b | YSEAIRYLKATTERFPSS | 158 |
| | 3a | QDYTQVLLMVDSFLHQF | 159 |
| | 3b | QDYTQVLLTVDSFLHQF | 160 |
| | 4a | NQAYAVYMAGLTNAATGDNFIQDFF | 161 |
| | 4b | NQAYAVYMAGLTNAATGDNVIQDFF | 162 |
| | 5a | ETTSMRTAFSNFQNLVR | 163 |
| | 6a | QDALARMAYIKDALARHELEIAKFY | 164 |
| | 7a | WVAVANRVVGML | 165 |
| | 8a | TKATYEGLFLMQEAYEKM | 166 |
| | 9a | ANDTQKIIDANKDKTFAPIEKPNEPDLKVPAV | 167 |
| | 9b | ANDTQKIIDANKDKTFSPIEKPNEPDLKVPAV | 168 |

TABLE 4-continued

Eptiopes of Nontypeable Haemophilus influenzae (NTHi)

| Protein[a] | Peptide No. | Peptide Sequence | SEQ ID NO |
|---|---|---|---|
| YajG | 1a | SNAWVTVDVREFGTQVEQGNLRYKLNTKIQ | 169 |
| | 1b | SNAWVTVDLREFGTQVEQGNLRYKLNTKIQ | 170 |
| | 1c | SNAWVTVDVHEFGTQVEQGNLRYKLNTKIQ | 171 |
| | 1d | SNAWVTVDVREFSTQVEQGNLRYKLNTKIQ | 172 |
| | 1e | SNAWVTVDVREFATQVEQGNLRYKLNTKIQ | 173 |
| | 2a | VYVQGAKGSYNKSFNVTHSQEGVFNAGNDEI | 174 |
| | 2b | VYVQGAKGSYNKSFNVTRSQEGVFNADNDEI | 175 |
| | 2c | VYVQGAKGSYNKSFNVTHSQEGVFNADNDEI | 176 |
| | 2d | VYVQGAKGSYNKSFNVTHSQEGVFNAENDEI | 177 |
| | 3a | TFNDIVNNIYQDQEVAAAINQYSN | 178 |
| | 3b | TFNDIVNNIYQDQEVAVAINQYSN | 179 |
| OmpP2 | 1a | ITSAEDKEYGV | 180 |
| | 1b | ITTAEDKEYGL | 181 |
| | 1c | ITTAEDKEYGV | 182 |
| MltA | 1a | CTSNTKNTQIPTTPNGSDPQQFGAKYTNRTYQQTA | 183 |
| | 1b | CTSNTKNTQIPTTSNGSDPQQFGAKYTNRTYQQTA | 184 |
| | 1c | CTSNTKNTQIPTTLNGSDPQQFGAKYTNRTYQQTA | 185 |
| | 1d | CTSNIKNIQIPTTLNGSDPQQFGAKYTNRTYQQAA | 186 |
| | 2a | SNIKNYSSKLSTNFYDNYEKITNWVL | 187 |
| | 2b | SNIKIIQVNFPPIFTYNYEKITNWVL | 188 |
| | 3a | SDSMLENFLLGVQGSGYVDF | 189 |
| | 4a | YTAIGRLLVEDGEI | 190 |
| | 5a | SIQAIREWGNRN | 191 |
| | 5b | SIQAIREWSNRN | 192 |
| | 6a | RAGHIAGLSKHYGRVWVL | 193 |
| Ycct | 1a | LAIDGQKASKSLGKAKTFTVDDTQNHQVVVRL | 194 |
| | 1b | LAIDGQKASKSLGKAKTFTIDDTQNHQVVVRL | 195 |
| | 1c | LAIDGQKASKSLGKAKTFTVDDTQSHQVVVRL | 196 |
| | 1d | LVIDGQKAAKSLLKNTKTFNVSDTKHQVVVRL | 197 |
| | 2a | IRNLDSGDKFNQMPNITVKTKSGNATSA | 198 |
| | 2b | IRNLDSGDKFNEMPNITVKTKSGNATSA | 199 |
| LppC | 1a | ARIEMDKNLTDVQRRQDNIDKTWAL | 200 |
| | 1b | ARIEMDKNLTDVQRHQDNIDKTWAL | 201 |
| | 2a | CYYGLSPEDEAESAANKMWNDGVRNPL | 202 |
| | 3a | DIPFFKDTNSPQYHKLAKSTGGEYQLMR | 203 |
| | 4a | LSADTNCNVERDMTWYQYQDGAI | 204 |
| Spr | 1a | QLTGLINNLEKDNRTGIFHKVRTNRSSALMG | 205 |
| | 2a | FGIELPRSTAEQRHLGRKINKSELKKGDLVFF | 206 |
| | 2b | FGIELPRSTAEQRHLGRKINKSELKRGDLVFF | 207 |
| | 3a | GQGVTISSLDEKYWARTYTQ | 208 |
| NTHI1930 | 1a | VPAIFSSQTLLGKNATTQAFFDI | 209 |
| | 1b | VPTIFSSQTLLGKNATTQAFFDI | 210 |
| | 1c | VPAIFSSQTLLEKNATTQAFFDI | 211 |
| | 1d | VPAIFSSQTLLGKNAATQAFFDI | 212 |
| | 2a | GNAELKLASGQYHNEQSKTDFDWSNVVLN | 213 |
| | 2b | GNAELKLASGQYHNEQSKADFDWSNVVLN | 214 |
| | 2c | GNAELKLASGQYHNEQSKAELDWSNVVLN | 215 |
| | 2d | GNAELKLASGQYHNEQSKADFDWSNIILN | 216 |
| | 2e | GNAELKLASGQYHNEQSKADFDWSNIVLN | 217 |
| | 3a | KTNLDELHINGNNLGKVTNNVEFNHIDGNA | 218 |
| | 3b | KTNMDELHINGKNLGKFTNNLELNHIDGNA | 219 |
| | 3c | KTNLDELHINGNNLGKVSNNVEFNHIDGNA | 220 |
| | 4a | VQKLQQAGMIIANNQPQIKFTPLSISDEKGK | 221 |
| | 4b | VQKLQQAGMEIANNQPQIKFTPLSISDEKGK | 222 |
| | 4c | VQKLQQAGMEIANNQSQIKFTPLSISDEKGK | 223 |
| | 4d | VQKLQQAGMVIANNQAQIKFTPLSISDEKGK | 224 |
| | 4e | VQKLQQAGMTIANNQPQIKFTPLSISDEKGK | 225 |
| | 4f | VQKLQQAGMAIANNQPQIKFTPLSISDEKGK | 226 |
| | 4g | VQKLQQAGMLIANNQPQIKFTPLSISDEKGK | 227 |
| | 4h | VQKLQQAGMIIANNQLQIKFTPLSISDEKGK | 228 |
| | 5a | LENNDLKLNGKPIPEEQ | 229 |
| | 5b | LENNELKLNGKPIPEEQ | 230 |
| NlpC | 1a | ASLFLFACSSFQNDDYAMNYKGQIGDPIMAIAM | 231 |
| | 2a | DRFNLRLPRSTVEQANYGKHVRKEDIQTGDLI | 232 |
| | 2b | DRFNLRLPRSTTEQANYGKHVRKEDIQTGDLI | 233 |
| | 2c | DRFNLRLPRSTVEQANYGKHVRKEHIQTGDLI | 234 |

TABLE 4-continued

Eptiopes of Nontypeable Haemophilus influenzae (NTHi)

| Protein | Peptide No. | Peptide Sequence | SEQ ID NO |
|---|---|---|---|
| | 3a | FFKTGRGPNGYHVGIYVKEDKFLHAS | 235 |
| | 3b | FFKTGLGPNGYHVGIYVKEDKFLHAS | 236 |
| | 3c | FFKTGRGPNGYHVGIYVKEGKFLHAS | 237 |
| | 4a | GVVYSSMNNPYWSKAFWQVRRI | 238 |
| | 4b | GVVYSSMNNLYWSKAFWQVRRI | 239 |
| TdeA | 1a | QRRVDISTNSAISHK | 240 |
| | 1b | QRRVDISTNSATSHK | 241 |
| | 1c | QRRVDTSTNSATSHK | 242 |
| | 2a | ASTVGTALHNP | 243 |
| | 2b | ASTIGTALHNP | 244 |
| Lpp | 1a | VTGCANTDIFSGDVYSASQAKEARSITYGTIV | 245 |
| | 1b | VTGCANTDVFSGDVYSASQAKEARSITYGTIV | 246 |
| | 1c | VAGCTNTDIFSGDVYSASQAKEARSITYGTIV | 247 |
| | 2a | IEEKMSQVNGAELVIKKDDGQEIVV | 248 |
| | 2b | IEEKVSQVNGAELVIKKDDGQEIVV | 249 |
| LolB | 1a | ISPTERFSSRFEWQYQNPKSYTLKL | 250 |
| | 1b | ISPKERFSSRFEWQYQNPKSYTLKL | 251 |
| | 1c | ISPTERFSSHFEWQYQNPKSYTLKL | 252 |
| | 2a | IQMHQSGMTISDNNGNQQYAANAKQLLQE | 253 |
| | 2b | IQMHQSGMTISDNNGNQQSADNAKLLLQE | 254 |
| | 2c | IQMNQSGMTISDNNGNQQSADNAKLLQE | 255 |
| | 2d | IQMHQSGMTISDNNGNQQYAANSKQLLQE | 256 |
| | 3a | DGSQWTADYLTYHSNNSMPENILL | 257 |
| NTHI1387 | 1a | EFSVQNSPHLPSRDTIYFEDGRDYFSYKEPIEQASR | 258 |
| | 1b | EFSVQKSPHLPSRDTIYFEDGRDYFSYKEPIEQASR | 259 |
| | 1c | EFSVQNSPYLPSRDTIYFEDGRDYFSYKEPIEQASR | 260 |
| | 1d | EFSVQNSPYLPSRDTIYFEDGRDYFSYQEPIEQASR | 261 |
| | 1e | EFSVQNSPYLPSRDTIYFEDGRDYFSYQEPIEQVSR | 262 |
| | 1f | EFSVQNSPYLPSRDTIYFEDGRDYFSYKEPIEQVSR | 263 |
| | 2a | LLFETSEKSRYTELSTSNKIQQWAEEQGLDK | 264 |
| | 2b | LLFETSEKSRYTELSTSNKIQQWAEKQGLDK | 265 |
| | 2c | LLFETSEKSRYTELSATNKIQQWAEEQGLDK | 266 |
| | 2d | LLFETSEKSRYTELSSTNKIQQWAEEQGLDK | 267 |
| | 3a | LYNDDYSVAVLDFLVNKIEQE | 268 |
| OlpA | 1a | THHGKVDGTKIQ | 269 |
| | 2a | NQFKYTNRAEQKFKSSSDIKLGY | 270 |
| | 2b | NQFKYTNRAEQNFKSSSEIKLGY | 271 |
| | 2c | NQFKYTNRAEQKFKSSSDIELGY | 272 |
| | 2d | NQFKYTNRTEQKFKSSSDIKLGY | 273 |
| | 3a | FDSTKVNNY | 274 |
| OmpU | 1a | SWDYQKSTSNHAFYRYDKNR | 275 |
| | 2a | FNGNGKYYWDNKKYNE | 276 |
| | 3a | FQEKRWYAGGSSGTNTMKQYADK | 277 |
| | 3b | FKEKRWYAGGSSGTNTMKQYADK | 278 |
| | 4a | GKSRYKIRKHLDG | 279 |
| | 4b | GKSRYKTRKHLDG | 280 |
| | 4c | GESRYKIRKHLDG | 281 |
| | 5a | RENTQALDNAYQQK | 282 |
| | 6a | ANRAYREKDLIGIQQKNRE | 283 |
| | 6b | ANRVYREKDLIGIQQKNRE | 284 |
| | 6c | ANRVYREKDLIGIQQRNRE | 285 |
| | 7a | LNDDNLNNAPKSGTKI | 286 |
| Tbp2 | 1a | IPSLGGGMKLVA | 287 |
| | 1b | IPSLGGGMKLVV | 288 |
| | 2a | QKYVYSGLYYI | 289 |
| | 2b | QRYVYSGLYYI | 290 |
| | 2c | QQYVYSGLYYI | 291 |
| | 3a | EGTLEGGFYGP | 292 |
| | 3b | DGTLEGGFYGP | 293 |
| | 4a | SFGEADYLLI | 294 |
| | 5a | ACCSNLSYVKFG | 295 |
| | 5b | ACCKNLSYVKFG | 296 |
| | 5c | ACCNNLSYVKFG | 297 |
| | 6a | AILLGGYFTYNS | 298 |
| | 6b | ASELGGYFTYNS | 299 |

TABLE 4-continued

Epitopes of Nontypeable Haemophilus influenzae (NTHi)

| Protein | Peptide No. | Peptide Sequence | SEQ ID NO |
|---|---|---|---|
| IgA1 | 1a | NYSSEQYRRF | 300 |
|  | 1b | NYSSSQYRRF | 301 |
|  | 1c | NYSSSQYRHF | 302 |
|  | 2a | GKINVNGYDFAYNVEN | 303 |
|  | 2b | GKINVTRYDFAYNVEN | 304 |
|  | 2c | GKINVNQYDFAYNVEN | 305 |
|  | 2d | GKINVNQYDFAYNMEN | 306 |
|  | 2e | GKINVDRYDFAYNVEN | 307 |
| NTHI1140 | 1a | EQCVYPNLTRILQQHFSKEDSYIHSQYVFFYPLEKIIGEQYVKIIQ | 308 |
|  | 2a | VKGQYKNGMVEVQKNEDGTPKNSDGIATNQNKFF | 309 |
|  | 2b | VKGQYKNGMVEMQKNEDGTPKNSDGIATNQNKFF | 310 |
|  | 2c | VKGQYKNGMLEVQKNEDGTPKNSDGIATNQNKFF | 311 |
|  | 3a | DEKSMNYASYQFKKFRT | 312 |
| YcfL | 1a | NLTYSTKPILNITS | 313 |
|  | 2a | QKSAVIKNKS | 314 |
|  | 3a | LYWYDHLGVTQ | 315 |
|  | 4a | WENQQESYSAQF | 316 |
|  | 5a | LKPQEQKSIDLTKPTVESKNYRLYLK | 317 |
|  | 5b | LKPQEEKSIDLIKPTVESKNYRLYLK | 318 |
|  | 5c | LKPQEEKSIDLIKPTAESKNYRLYLK | 319 |
| LptE | 1a | QQSVTMPNEWRTLALESDDSYNDFTVIMRRKLQENQVN | 320 |
|  | 2a | PILRINKQITSDQVASIFKHGREAEK | 321 |
|  | 3a | RLANGESYPINAKVNRTFFDNARAA | 322 |
|  | 3b | RLTNGESYPINAKVNRTFFDNARAA | 323 |
|  | 3c | RLTNGESYPVNAKVNRTFFDNARAA | 324 |
|  | 4a | EVIWNDMREQVARQLIVKIIALQNQIK | 325 |
| BamA | 1a | ENYDNSKSDTSS | 326 |
|  | 2a | FALEYNRNLYIQSMKFKGNGIKTN | 327 |
|  | 3a | GFGNKRLPFYQTYTAGGIGSLRGFAYGSIGPNAIY | 328 |
|  | 4a | IKKYENDDVEQF | 329 |
|  | 5a | KLPDYGKSSR | 330 |
|  | 5b | SLPDYGKSSR | 331 |
|  | 5c | DLPDYGKSSR | 332 |
|  | 6a | SSDVIGGNAI | 333 |
|  | 6b | SSDVVGGNAI | 334 |
| Skp | 1a | AGYIFQHHPDRQAVADKL | 335 |
|  | 2a | ALEKDAPRLRQADIQKRQQEINKLGAAED | 336 |
|  | 2b | ALEKDAPRLRQADIQKRQEEINKLGATED | 337 |
|  | 3a | LMQEQDKKVQEFQAQNEKRQAEERGKLL | 338 |
|  | 4a | ATNNLAKAKGYTYVLDA | 339 |
|  | 5a | KDIIEEVLKSIPASEK | 340 |
| SmpA | 1a | DVPQGNYLEATTVAQVKEGM | 341 |
|  | 2a | LVDPYNSQTWYYVFLQQRAYETPVQHT | 342 |
|  | 2b | LIDPYNNYTWYYVFLQQRAYETPVQHT | 343 |
|  | 2c | LIDPYNNYTWYYVFLQQHAYETPVQHT | 344 |
|  | 2d | LIDPYNNYTWYYVFLQQRAYETPAQHT | 345 |
|  | 3a | TETHLDKPLPQVSQQGENNTIIETGEKPKSSWWK | 346 |
|  | 3b | TETHLDKPLPEVSQQGENNTIIETGEKPKSSWWK | 347 |
|  | 3c | TETHLDKPLPQVSQQDENNTIIETGEKPKSSWWK | 348 |
| MltC | 1a | DTQGLDILTGQFSHNID | 349 |
|  | 2a | LVASRKDYVKYTDSFYTRSHVS | 350 |
|  | 3a | VHTLLMGADAKGIDL | 351 |
|  | 4a | ANHVEVRARKYLPLIRKAAQR | 352 |
|  | 5a | GIDESLILGIMQTESSFNP | 353 |
|  | 6a | VFTMKGKGGQPSTRYLYDPANNIDAGVSYLW | 354 |
|  | 6b | VFTMKGKGGQPSTRYLYDPTNNIDAGVSYLW | 355 |
|  | 6c | VFAMKGKGGQPSTRYLYDPTNNIDAGVSYLW | 356 |
|  | 7a | NPTSKRFAMISAYNS | 357 |
|  | 8a | AGAVLRVFDNDK | 358 |
|  | 9a | DTAIYKINQMYPEQVYRILTT | 359 |
|  | 10a | SSQARNYLLKVDKAQK | 360 |
| EnvC | 1a | DLNQIQKQIKQQESKIEKQKREQAKLQANLKKHESK | 361 |
|  | 1b | DLNQIQKQIKQQESKIEKQKLQQAKLQANLKKHESK | 362 |
|  | 1c | DLNQIQKQIKQQESKIEKQKLQQTKLQANLKKHESK | 363 |
|  | 2a | KAERMKVYYQHLNQVRIEMI | 364 |
|  | 3a | SQQKNHRNQLSTQKKQQQALQKAQ | 365 |

TABLE 4-continued

Eptiopes of Nontypeable Haemophilus influenzae (NTHi)

| Protein[a] | Peptide No. | Peptide Sequence | SEQ ID NO |
|---|---|---|---|
| | 4a | QSTLNELNKNLA | 366 |
| | 5a | LKANEQALRQEIQRA | 367 |
| | 6a | LAQRQKAEEKRTSKPYQPTVQERQL | 368 |
| | 7a | QAGEVRWKGMVI | 369 |
| | 8a | AGYLNGYGYMVIVK | 370 |
| | 9a | TDLSLYGFNQ | 371 |
| | 10a | QVGNTGEISRSALYFGIS | 372 |
| LptD | 1a | DRRRSGLLIPSAGTSN | 373 |
| | 1b | DRRRSGLLIPSAGTSS | 374 |
| | 1c | DRRRSGLLIPNAGTSN | 375 |
| | 2a | GKVAGEYLGKDRYSEYASDNRKR | 376 |
| | 2b | GKVAGEYLGKVRYSEYASDNRKR | 377 |
| | 2c | GKVAGEYLGGDRYSEYASNNRKR | 378 |
| | 3a | TRVSDKRYFNDFDSIYGRSTD | 379 |
| | 3b | TRVSDKRYFDDFDSIYGRSTD | 380 |
| | 3c | TRVSDKRYFNDFDSVYGRSTD | 381 |
| | 4a | HQFQIFDDIVNIGP | 382 |
| | 4b | RQFQIFDDIVNIGP | 383 |
| | 5a | QAVRFDNDSELMPTA | 384 |
| | 5b | QAVRFDNDSKLMPTA | 385 |
| | 6a | TRYEQKKGSGKNAEDVQKTVNRVIPQ | 386 |
| | 6b | TRYEQKKGSGKNAKDVQKTVNRVIPQ | 387 |
| | 7a | PYRNQSNIGSTLNNDYLGFGYDSALVQQDYYSLFRDRRYSGLDRISSA | 388 |
| | 7b | PYRNQSNIGSTLNNDYLGFGYDSALVQQDYYSLFRDHRYSGLDRISSA | 389 |
| | 7c | PYRNQSNIGSTLNNEYLGFGYDSALVQQDYYSLFRDHRYSGLDRISSA | 390 |
| | 8a | SNSRIDENPANKTPTSSA | 391 |
| | 9a | DTHTNSTSLANTSLEYNPEKNNLIQLNYRYVNQEYIDQNLGKSANAYQQDIQQ | 392 |
| | 9b | DTHTNSTSLANTSLEYNPEKNNLIQLNYRYSNQEYIDQNLGKSANAYQQDIQQ | 393 |
| | 10a | VGVKRNVTNHQNQTRNEI | 394 |
| LppB | 1a | NVGGAWQPEIQKNSLPT | 395 |
| | 2a | PAQPAFQPSPKTVVS | 396 |
| | 3a | QHINIPRNPNTNAPDYSKISKGSYKGNTYKVNKGDT | 397 |
| | 3b | QHINIPRNPNTNVPDYSKISKGSYKGNTYKVNKGDT | 398 |
| | 4a | DVKELAALNNLSEPYNLSLGQVLK | 399 |
| | 5a | KTVTTTVSVKQPAVT | 400 |
| | 6a | AVTYTPGANGTQIGSDGTIIGPIKS | 401 |
| | 7a | TSSTQVTSSVNN | 402 |
| | 8a | WQWPTSGNIIQGFSSADGGNKGIDISGSRGQAVKA | 403 |
| | 8b | WQWPTSGNIIQGFSSTDGGNKGIDISGSRGQAVKA | 404 |
| | 9a | GNALRGYGNLIIIKHNDD | 405 |
| | 10a | AYAHNDKILVADQ | 406 |
| | 10b | AYAHNDKILVVDQ | 407 |
| | 11a | KAGQDIAKMGSSGTN | 408 |
| | 12a | RYKGKSVDPVRYLP | 409 |
| TpsA | 1a | EGEKENDTNTR | 410 |
| | 2a | SFTQADITDKTLLLYPTVGFT | 411 |
| | 2b | SFIQADITDKTLLLYPTVGFT | 412 |
| | 2c | SESSFIKVQAS | 413 |
| | 3a | LHTKDIEKIPPT | 414 |
| | 3b | LHTKYIEKIPPT | 415 |
| | 3c | LHTKGIEKIPPT | 416 |
| | 4a | NKNGKLVGGSRLL | 417 |
| | 4b | NRNGKLVGGSRLL | 418 |
| | 5a | IRDKDNSKNI | 419 |
| TpsB | 1a | EPLKSAGKEILPASDVDL | 420 |
| | 1b | EPLKSDGKEILPASDVDL | 421 |
| | 1c | EPLKSDGKEILPESDVDL | 422 |
| | 1d | EPLKSAGKEILPESDVDL | 423 |
| | 1e | EPLKSSGKEILPESDVDL | 424 |
| | 2a | LKKSTALSLKTKGV | 425 |
| | 2b | LKKSTALSVKTKGV | 426 |
| | 3a | AKGQYTFVNTMTPLKINDVTLKLTGDLLNYHAE | 427 |
| | 3b | AKGQYTFVNTMAPLKINDVTLKLTGDLLNYHAE | 428 |
| | 3c | AKGQYTFVNTMMPLKINDVTLKLTGDLLNYHAE | 429 |
| | 3d | AKGQYAFVNTMTPLKINDVTLKLTGDLLNYHAE | 430 |
| | 3e | AKGQYAFVNTMAPLKINDVTLKLTGDLLNYHAE | 431 |
| | 3f | AKGQYSFVNTMAPLKINDMTLKLTGDLLNYHAE | 432 |

TABLE 4-continued

Epitopes of Nontypeable Haemophilus influenzae (NTHi)

| Protein[a] | Peptide No. | Peptide Sequence | SEQ ID NO |
|---|---|---|---|
| | 4a | SLDGKSEFVGTANWKEGANWDIQADLEKMN | 433 |
| | 4b | SLDGKSEFVGTVNWKEGANWDIQADLEKMN | 434 |
| | 4c | SLDGKSEFVGNANWKNSTDWDIQADLEKMN | 435 |
| | 4d | SLDGKSEFVGTVNWKEGANWDIQADLEKMN | 436 |
| | 4e | SLDGKSEFAGNANWKNGANWDIQADLEKMN | 437 |
| | 5a | FFVPVMPATLSGKL | 438 |
| | 5b | FFVPVMPAILSGKL | 439 |
| | 6a | SRGFAGSQGWQVEV | 440 |
| | 6b | SRGFADSQGWQVEV | 441 |
| | 7a | PNLRGLWSDLK | 442 |
| | 8a | LQGFQLAKASIKGHINN | 443 |
| | 9a | HLLDLDLSGDEQ | 444 |
| | 10a | QGNIPFQFKRVNLDL | 445 |
| | 11a | HLAFSQKLDYRTF | 446 |
| | 12a | IPKLTLNADIQNNNLVLKT | 447 |
| | 13a | INVHNQGRIVGDI | 448 |
| | 13b | INLHNQGRIVGDI | 449 |
| | 14a | IANQLLTQGESVNG | 450 |
| | 14b | IANQLLTSGESVNG | 451 |
| | 15a | GNLEKPLLNG | 452 |
| | 16a | IRTKLKSMPVNI | 453 |
| | 17a | NNFNVDIPSMAK | 454 |
| | 18a | RIKIDSLPDTAEPVSEDEVILNGPHKSKEE | 455 |
| | 18b | RIKIDSLPDTAEPVSEDEIILNGPHKSKEE | 456 |
| | 19a | TKGRYASFGQD | 457 |
| | 20a | KITAGVRVIGIADSPEVTIFSEPSKSQDQALSYLLTGRSLESSG | 458 |
| | 20b | KITAGVRVIGIADSPEVTIFSEPSKPQDQALSYLLTGRSLESSG | 459 |
| | 21a | GISKSGKLVGSIGEVFGIQDLNLGTSGVGDKSKVTVSGNIT | 460 |
| | 22a | FQSVSSTNQVF | 461 |
| Hel | 1a | DNSPYAGWQVQNNKPFDGKD | 462 |
| | 1b | TMLDNSPYAGWQVKNNKPFDGKDWTRW | 463 |
| | 2a | GDNLDDFGNTVYGKLNADRR | 464 |
| | 2b | GDNLDDFGNSVYGKLNADRR | 465 |
| | 2c | VGDNLDDFGNTVYGKLNADRRA | 466 |
| | 2d | VGDNLDDFGNSVYGKLNADRRA | 467 |
| | 3a | GEYRALAYQAYNAAKVAFD | 468 |
| | 3b | GEYKALAYQAYNAAKVAFD | 469 |
| | 4a | VEFNNYVNSHKGKVFY | 470 |
| | 4b | VEFNNYVNSHNGKVFY | 471 |
| | 5a | EKAGTIDDMKRLG | 472 |
| | 6a | SAKAARFAEIEKQGYEI | 473 |
| | 7a | ANMQLQQQAVLGLNWMQ | 474 |
| | 8a | MLPNANYGGWEGGLAEGYFKKD | 475 |
| | 9a | TQGQIKARLDAV | 476 |
| | 9b | TQGQIKARLDAI | 477 |
| HemR | 1a | NAGDYKRPDNSKILFSKNNQKTGLIK | 478 |
| | 1b | NAGDYKRPDNSRILFSKNNQKTGLIK | 479 |
| | 1c | NADDYKRPDNSRILFSKNNQKTGLIK | 480 |
| | 2a | GKNEIFKTRGVNCVGNA | 481 |
| | 2b | GKNEIFKTRGVYCVGNA | 482 |
| | 2c | GKNEIFKTRGVYCAGNA | 483 |
| | 2d | GKNEIFKTRGVYCVGNS | 484 |
| | 3a | KRDTSPRNPWGKTSTWIAEIP | 485 |
| | 3b | KRDTSPRNPWGKTLTWIAEIP | 486 |
| | 3c | KRDTSPRNPWSKTSTWIAEIP | 487 |
| | 4a | DNLFNRAYNPYLGELASGTGRN | 488 |
| | 4b | DNLFNRAYKPYLGELASGTGRN | 489 |
| Hup | 1a | FYSTALDSGQSGGSSQF | 490 |
| | 2a | YGYSQREVSQDYRIGG | 491 |
| | 3a | LPQRSVILQPSGK | 492 |
| | 3b | LPKRSVILQPSGK | 493 |
| | 4a | MPNIQEMFFSQVSVSNAGVNTALKP | 494 |
| | 4b | MPNIQEMFFSQVSVSDAGVNTALKP | 495 |
| | 4c | MPNIQEMFFSQVSVSDVGVNTALKP | 496 |
| | 5a | ILKQGYGLSRI | 497 |
| | 5b | ILKQGYGLSRV | 498 |
| | 5c | TLKQGYGLSRI | 499 |
| | 6a | QNLLDKRYVDPLDAGNDAASQRYYSSLN | 500 |
| | 6b | QNLLDKRYVDPLDSGNDAASQRYYSSLN | 501 |
| | 6c | QNLLDKRYVDPLDAGNDSASQRYYSSLN | 502 |

TABLE 4-continued

Eptiopes of Nontypeable Haemophilus influenzae (NTHi)

| Protein<sub>a</sub> | Peptide No. | Peptide Sequence | SEQ ID NO |
|---|---|---|---|
| | 7a | DKTRVLYNFARGRTY | 503 |
| | 7b | DKTRVLYNFARGRTY | 504 |
| | 7c | DKPRVLYNFARGRTY | 505 |
| NTHI1794m | 1a | NSDQNGFQRGEIKPENISINGADPNQTAYFV | 506 |
| | 1b | NSDQDGFQRGEIKPENISINGADPNQTAYFV | 507 |
| | 2a | NWTPQEKERIEFGLRYSNYKELKYF | 508 |
| | 2b | NWTPQEKERIELGLRYSNYKELKYF | 509 |
| | 3a | GRSFASLKLANRLIK | 510 |
| | 3b | GRSFASLKLANGILK | 511 |
| | 3c | GRSFASLKLAYRILK | 512 |
| | 3d | GRSFAPLKLANGILK | 513 |
| | 4a | ELQPKYNKQTFNILAEKRLNDNLGMVLGYSRRTSSIEQNRLIG | 514 |
| | 4b | ELQPKYDKQTFNILAEKRLNDNLGMVFGYSRRTSSIEQNRLIG | 515 |
| | 4c | ELQPKYNKQTFNILAEKRLNDNLGMVFGYSRRTSSIEQNRLIG | 516 |
| Tbp1 | 1a | HCSLYPNPSKNCRPTLDKPY | 517 |
| | 1b | HCSLYPNPSKNCRPTRDKPY | 518 |
| | 2a | ANESTISVGKFKN | 519 |
| | 3a | NPSFAEMYGWRYGG | 520 |
| | 3b | NPSFSEMYGWRYGG | 521 |
| | 4a | VKDQKINAGLASVSSYLFDAIQPS | 522 |
| | 4b | VKDQKINTGLASVSSYLFDAIQPS | 523 |
| | 5a | NLLNYRYVTWEAVRQTAQGAVNQHQNVGNYTRYAASG | 524 |
| | 5b | NLFNYRYVTWEAVRQTAQGAVNQHQNVGNYTRYAASG | 525 |
| | 5c | NLLNYRYVTWEALRQTAQGAVNQHQNVGNYTRYAASG | 526 |
| | 5d | NLLNYRYVTWEAVRQTAQGAVNQHQNIGNYTRYAASG | 527 |
| | 5e | NLFNYRYVTWEAVRQTAQGAVNQHQNIGNYTRYAASG | 528 |
| | 5f | NLLNYRYVTWEAVRQTAQGAVNQHQNVGSYTRYAASG | 529 |
| | 5g | NLFNYRYVTWEAVRQTAQGAVNQHQNVGSYTRYAASG | 530 |
| | 5h | NLFNYRYVTWEAVRQTAQGAVNQHQNIGSYTRYAASG | 531 |
| | 6a | ETQVHKDALKGVQSY | 532 |
| | 6b | ETQVHKDALRGVQSY | 533 |
| | 6c | ETQVHPDALKGVQSY | 534 |
| | 7a | ETVSVSDYTGANRIKPNPM | 535 |
| | 7b | EIVSVSDYTGANRIKPNPM | 536 |
| HgpC | 1a | DGLRQAETLSSQGFKELFEGYGNFNNTRNSIE | 537 |
| | 2a | HEIENYDYKIYPNKQADL | 538 |
| | 2b | HEIENYDYKIYPNKQTDF | 539 |
| | 2c | HEIENYDYKIYPNKQTDL | 540 |
| | 3a | FGERIINDQSKR | 541 |
| | 3b | HGERVINDQSKR | 542 |
| | 3c | HGERIINDQSKR | 543 |
| | 3d | YGERVINDQSKR | 544 |
| | 3e | YGERIINDQSKR | 545 |
| | 4a | TNKARSDEYCHQSTC | 546 |
| | 4b | TNKARSDEYCHQPTC | 547 |
| | 4c | TNKAHSDEYCHQSTC | 548 |
| | 5a | NLALLLRKTTYK | 549 |
| | 5b | NLALLLRKTDYK | 550 |
| | 6a | FRAPTSDEIYMTFKHPQFSIQPNTDLKAE | 551 |
| | 6b | FRAPTSDEIYMTFKHPDFSIGPNTDLKAE | 552 |
| | 6c | FRAPTSDEIYMTFKHPQFSILPNTDLKAE | 553 |
| | 7a | AAKKAKDSFNSQWTSMV | 554 |
| | 7b | AAKKAKDTFNSQWTSMV | 555 |
| | 8a | ANGKEVKDSRGLWRNNR | 556 |
| | 8b | ANGKDVKDSRGLWRNNR | 557 |
| | 8c | VNGKDVKDSRGLWRNNR | 558 |
| | 9a | NLTNKKYLTWDSARSVRHLGTINRV | 559 |
| | 9b | NLTNKKYLTWDSARSIRHLGTINRV | 560 |
| | 9c | NLTNKKYLTWDSARSIRHIGTINRV | 561 |
| HgpB | 1a | QRIKTRARTDDYCDAGVR | 562 |
| | 1b | QKIKTRARTDDYCDAGVR | 563 |
| | 1c | QRIKTRARTDEYCDAGVR | 564 |
| | 2a | QKGRMDGNIPMNAIQPK | 565 |
| | 2b | QKGRINGNIPMNAIQPK | 566 |
| | 2c | QKGRMNGNIPMNAIQPK | 567 |
| | 2d | QKGRMNGNIPMNAIQPR | 568 |
| | 3a | GYVQPIKNLTIRAGVYNLTNRKYITWDSARSIRSFGTSNVIEQTTGLGINRFYA | 569 |
| | 3b | GYVQPIKNLTIRAGVYNLTNRKYITWDSVRSIRSFGTSNVIEQTTGQGINRFYA | 570 |

TABLE 4-continued

Epitopes of Nontypeable Haemophilus influenzae (NTHi)

| Protein[a] | Peptide No. | Peptide Sequence | SEQ ID NO |
|---|---|---|---|
| | 3c | GYVQPIKNLTIRAGVYNLTNRKYITWDSARSIRSFGTSNVIEQTTGQGINRFYA | 571 |
| | 3d | GYVQPIKNLTIRAGVYNLTNRKYITWDSARSIRSFGTSNVIEQKTGQGINRFYA | 572 |
| | 3e | GYVQPIKNLTIRAGVYNLTNRKYITWDSARSIRSFGTSNVIEQSTGLGINRFYA | 573 |
| | 3f | GYVQPIKNLTIRAGVYNLTNRKYITWDSARSIRSFGTSNVIEQSTGQGINRFYA | 574 |
| | 4a | HELENYDYKNADSLTQGKRREKADPY | 575 |
| | 4b | HELENYGYKNYDDKIQGKRREKADPY | 576 |
| | 5a | DSRHTNDKTKRRNISFSYENFSQTPFWDTLKITYS | 577 |
| | 5b | DSRHTNDKTKRRNISFSYENYSQTPFWDTLKITYS | 578 |
| | 5c | DSRHTNDKTKRRNISFSYENFSQTPFWDTLKLTYS | 579 |
| | 5d | DSRHTNDKTKRRNISFSYENFSQTPFWDTLKITFS | 580 |
| | 6a | WQERDLDTNTQQLNLDLTK | 581 |
| | 7a | LCPRVDPEFSFLLP | 582 |
| | 7b | LCHRVDPEFSFLLP | 583 |
| | 7c | LCTRVDPEFSFLLP | 584 |
| | 8a | QPKYKHGVTPKLPDDIVKGLFIPL | 585 |
| | 9a | APTSDEMYFTFKHPDFTILPNTNLKPE | 586 |
| | 9b | TPTSDEMYFTFKHPDFTILPNTDLKPE | 587 |
| | 9c | APTSDEMYFTFKHPDFTIFPNTNLKPE | 588 |
| ComE-1 | 1a/b | TLNKDDGXaaYYLNGSQSGKGQ | 589 |
| Hel-2 | 2a/b | GDNLDDFGNXaaVYGKLNADRR | 590 |
| TdeA-1 | 1a/b | QRRVDISTNSAXaaSHK | 591 |

[a]Name of the protein target, hypothetical proteins denoted by locus designation in the 86-028NP genome annotation

DISCUSSION

There have been no vaccines licensed for prevention of infection caused by NTHi strains, or vaccines against both typeable Hi strains and NTHi strains. Since the NTHi strains lack capsular material, the principal moieties interacting with the external milieu are the lipooligosaccharides and the OMPs. In past years, several potential vaccine candidates against NTHi have been evaluated. In general, challenge with the homologous isolate has demonstrated protection, yet robust cross protection against other NTHi strains has not been observed. This may be a result of heterogeneity of the target region among NTHi strains. The H. influenzae protein D component of the pneumococcal vaccine has demonstrated a 35% protection rate in a clinical trial. From our studies, protein D (encoded by glpQ) exhibits multiple variant residues among NTHi strains. This may account for the low protection rate. Alternatively, expression of protein D may vary among different NTHi strains. Thus, failure of previous vaccine candidates may arise in part from problems of target protein conservation and/or biological accessibility. The present disclosure sought to obviate the problem of lack of conservation. An initial step in the present disclosure was to identify the conserved core OMPs shared by all the NTHi strains. Initially, 96 OMPs were identified in the genome sequence of strain 86-028NP. The presence of each of these genes was then determined in each of the other sequenced NTHi strains. These analyses indicated that most NTHi strains possess approximately 90 genes encoding OMPs. Of these, several are either distinct to a particular isolate or restricted to a few isolates, and are thus unsuited as vaccine candidates. For example, the Hmw1A, Hmw1B, Hmw2A, Hmw2B, HgpA, HgpD, and HgpE proteins are common among the NTHi, but not conserved in all [22,23]. Clearly, a large set of genomic sequences is required to exclude common, yet non-conserved OMPs. From the 21 genomically sequenced, diverse NTHi isolates, the core set of OMPs has been narrowed down to 62 proteins. Without wishing to be bound by theory, it is proposed that 62 genes encode the core OMPs of the NTHi.

The membrane embedded OMPs are structurally constrained to two main conformations: the β-barrel and the α-helix. Of the 62 core proteins, 29 map to these two structures. Twenty-five of these are of the β-barrel conformation, and four have α-helix conformations. The remaining OMPs are mostly localized outside of the outer membrane and anchored by a lipophilic tail or are secreted. These are less restrained by the membrane, and conformation is more problematic to predict. Using the programs PRED-TMBB, BOMP (β-barrel), and TMHMM (α-helix), 46 OMPs have been modelled. Of the amorphous proteins for which no homologous crystal structure was available, many have regions predicted to correspond to α-helices. These are generally external and have been considered as such for peptide selection. Some of the OMPs have very low homology across the entire sequence. For example, OmpP5 has been modeled and the internal/external regions defined; however, the externally exposed faces are extremely heterologous, and none of the peptide regions fulfilled the criteria for selection as potential vaccine candidates.

Initially, putative externally exposed loops were selected based on the length of the conserved region. Regions containing 10 or more amino acids were selected as possible linear epitopes. Surprisingly, as noted above, over 100 such regions in Table 4 showed complete identity with no variant residues in any of the sequences. Other selected loops showed variant residues at one or more positions. Some externally positioned loops appeared at first inspection to have little homology among the strains; however, further examination indicated that several distinct peptide sequences would cover all of the known sequence permutations for that loop. These regions were also selected as conserved, potentially protective epitopes. The presence of conserved external loops suggests that these regions play a critical role in protein function. Alternatively, variations in these regions may be unnecessary if the regions are not available to the human immune system.

Based on the 46 modeled proteins, and the other OMPs whose structures have been partially evaluated (identification of α-helices and β-barrels), more than 200 peptides satisfied the initial screening criteria. An animal model was utilized to empirically determine in vivo antibody accessibility. Table 1 shows peptides that were analyzed to determine their biological accessibility. Each was synthesized, and a subset thereof was conjugated to KLH and used to raise antisera.

Initially, the 5 peptides targeting regions of HxuC were analyzed. Peptides HxuC1 and HxuC2 generated antisera that were protective against challenge with NTHi R2866. Since these experiments were performed, new sequencing data have revealed that HxuC5 has a variant residue in the middle of the loop of other strains. In two of the newer sequences, an isoleucine residue is substituted for a methionine residue. The protein in strain R2866 has the methionine residue. Thus, sequence heterogeneity cannot explain the lack of protection observed by antisera raised to peptide HxuC5.

Based on the availability of genomic sequences at the time of these studies, many of the peptides (with the exception of ComE1, Hel2, and TdeA) were designed to loops that were absolutely conserved across the NTHi strains. Peptides ComE1, Hel2, and TdeA were both designed to match the inherent variability of the corresponding OM loop. The available sequence data showed that each had a single variant residue. To address this heterogeneity, two peptides were made for each sequence, and an equimolar mixture of each was used to inoculate the adult rats. The outer membrane loop from which the ComE1 peptide was designed was estimated at 33 amino acid residues. From this, a 20 amino acid region was selected based on maximal immunogenicity predicted by the AbDesigner algorithm [12]. Similarly the 20-mer peptide Hel1 was selected from an estimated exposed loop of 27 residues. Examination of the efficacy of protection of these peptides showed clearance of bacteremia at 48 hours following administration of the antisera raised to both of the Hel peptides and with the antisera raised to the ComE1 peptide.

At least forty externally exposed, conserved peptides were used to produce peptide-specific antisera. The antisera were tested for their in vivo passive protective capacity using the infant rat model of invasive H. influenzae. Twenty of the forty peptides described and analyzed herein induced sufficient antibody production to produce sera that provided passive protection in the infant rat model of disease. Antisera raised against 20 appeared to be non-protective, though if purified further could potentially have been protective. These data demonstrate that many conserved outer membrane peptides are antibody available and are useful as components of a vaccine.

Certain embodiments of the present disclosure are therefore directed to a peptide composition comprising at least one peptide that is able to induce an antibody response against a Nontypeable *Haemophilus influenzae* (NTHi). The peptide composition may include one, two, three, four, five, six, seven, eight, nine, ten, or more different peptides. Each of the one or more peptides may be from 10 to 60 amino acids in length and be either: (i) an amino acid sequence having from 80% to 100% identity (such as, but not limited to, at least 80% or at least 90% identity) to at least one amino acid sequence as set forth in the group of peptides shown in Tables 1, 3, and 4; or (ii) an antigenic fragment of at least one of the peptides as set forth in Tables 1, 3, and 4.

More particularly, in at least certain embodiments, the peptide composition comprises one, two, or more peptides, wherein each peptide is selected from the group consisting of: (a) an amino acid sequence of one of SEQ ID NOs: 1-591, inclusive; (b) an antigenic fragment of at least one amino acid sequence of (a); and (c) an amino acid sequence having at least 80% identity (such as, but not limited to, at least 90% identity) to at least one amino acid sequence of (a). In at least one embodiment, the peptide composition comprises five, six, seven, eight, nine, ten, or eleven peptides, wherein each peptide is selected from the amino acid sequences of (a)-(c) above.

More particularly, in at least certain embodiments, the peptide composition comprises one, two, or more peptides, wherein each peptide is selected from the group consisting of: (d) an amino acid sequence of one of SEQ ID NOs: 97, 101, 123, 139, 145, 153, 245, 268, 308, 321, 325, 328, 329, 341, 350, 460, 462, 518, 589, and 590; (e) an antigenic fragment of at least one amino acid sequence of (d); and (f) an amino acid sequence having at least 80% identity (such as, but not limited to, at least 90% identity) to at least one amino acid sequence of (d). In at least one embodiment, the peptide composition comprises five, six, seven, eight, nine, ten, or eleven peptides, wherein each peptide is selected from the amino acid sequences of (d)-(f) above.

In at least one embodiment, the peptide composition comprises one, two, or more peptides, wherein each peptide is selected from the group consisting of: (g) an amino acid sequence of one of SEQ ID NOs: 97, 145, 153, 308, 325, 328, 341, 350, 460, 462, and 517; (h) an antigenic fragment of at least one amino acid sequence of (g); and (i) an amino acid sequence having at least 80% identity (such as, but not limited to, at least 90% identity) to at least one amino acid sequence of (g). In at least one embodiment, the peptide composition comprises five, six, seven, eight, nine, ten, or eleven peptides, wherein each peptide is selected from the amino acid sequences of (g)-(i) above.

In a particular embodiment, the peptide composition comprises all the peptides of SEQ ID NOs: 308, 460, 153, 350, 268, 341, 329, 517, 123, and 245; in an alternative embodiment of this peptide composition, one or more antigenic fragment(s) of SEQ ID NOs: 308, 460, 153, 350, 268, 341, 329, 517, 123, and 245 replaces the corresponding peptide.

Any of the peptide compositions described above or otherwise contemplated herein may further comprise a pharmaceutically acceptable carrier, vehicle, diluent, and/or adjuvant. In addition, any of the peptide compositions described or otherwise contemplated herein may induce an antibody response against at least one or more Nontypeable *Haemophilus influenzae* strains selected from the group including 3655, 6P18H1, 7P49H1, PittAA, PittEE, PittGG, PittHH, PittII, R3021, R2846, R2866, 22.1-21, 22.4-21, 86-028NP, NT127, HI1373, HI1374, HI1388, HI1394, HI1408, HI1417, HI1426, HI1722, HI1974, HI2114 HI2116, and HI2343. In certain embodiments, the peptide composition is multivalent. Further, in addition to inducing an antibody response against at least one or more NTHi strains, the peptide composition may induce an antibody response against one or more Hi type b strains, including but not limited to, type b strains E1a, 10810, HI689, DL42 and HI701.

Certain embodiments of the present disclosure are directed to a peptide composition comprising at least one fusion polypeptide (fusion protein) able to induce an antibody response against a Nontypeable *Haemophilus influenzae*. The fusion polypeptide may include one, two, three, four, five, six, seven, eight, nine, ten, or more different peptides linked in series, wherein each of the one or more peptides is from 10 to 60 amino acids in length. Each of the peptides is: (i) an amino acid sequence having from 80% to 100% identity (such as, but not limited to, at least 80% or at least 90% identity) to at least one amino acid sequence as set forth in the group of peptides shown in Tables 1, 3, and 4; or (ii) an antigenic fragment of at least one of the peptides shown in Tables 1, 3, and 4.

More particularly, in at least certain embodiments, the fusion polypeptide comprises one, two, or more peptides, wherein each peptide is selected from the group of amino acid sequences of (a)-(i) above. The one, two, or more peptides may be linked together in any order, and the one, two, or more peptides may be linked directly together or indirectly via one or more amino acid linker sequences. In at least one embodiment, the fusion polypeptide comprises five, six, seven, eight, nine, ten, or eleven peptides, wherein each peptide is selected from the group of amino acid sequences of (a)-(i) above. The five or more peptides may be linked together in any order, and the five or more peptides may be linked directly together or indirectly via one or more amino acid linker sequences.

In a particular embodiment, the fusion polypeptide comprises all the peptides having SEQ ID NOs: 308, 460, 153, 350, 268, 341, 329, 517, 123, and 245, linked directly together in that order in series in the N-terminal to the C-terminal direction. Alternatively, the peptides may be linked indirectly via one or more amino acid linker sequences. In an alternative embodiment of this fusion polypeptide, one or more antigenic fragment(s) of SEQ ID NOs: 308, 460, 153, 350, 268, 341, 329, 517, 123, and 245 replaces the corresponding peptide.

Any of the fusion polypeptides described above or otherwise contemplated herein may be present in a composition that also includes a pharmaceutically acceptable carrier, vehicle, diluent, and/or adjuvant. In addition, any of the fusion polypeptides described or otherwise contemplated herein may induce an antibody response against at least one or more Nontypeable *Haemophilus influenzae* strains selected from the group including 3655, 6P18H1, 7P49H1, PittAA, PittEE, PittGG, PittHH, PittII, R3021, R2846, R2866, 22.1-21, 22.4-21, 86-028NP, NT127, HI1373, HI1374, HI1388, HI1394, HI1408, HI1417, HI1426, HI1722, HI1974, HI2114 HI2116, and HI2343. In certain embodiments, the fusion polypeptide is multivalent. Further, in addition to inducing an antibody response against at least one or more NTHi strains, the fusion polypeptide may induce an antibody response against one or more Hi type b strains, including but not limited to, type b strains E1a, 10810, HI689, DL42, and HI701.

In certain other embodiments, the present disclosure is directed to a peptide composition able to induce an antibody response against a Nontypeable *Haemophilus influenzae*, wherein the peptide composition is a carrier molecule composition comprising at least one peptide coupled to a carrier molecule. Each peptide may be from 10 to 60 amino acids in length and be either: (i) an amino acid sequence having from 80% to 100% identity (such as, but not limited to, at least 80% or at least 90% identity) to at least one amino acid sequence as set forth in the group of peptides shown in Tables 1, 3, and 4; or (ii) an antigenic fragment of at least one of the peptides as set forth in Tables 1, 3, and 4.

Further, the carrier molecule composition may include one, two, three, four, five, six, seven, eight, nine, ten, or more different peptides coupled to the same or different carrier molecules. Each peptide may be from 10 to 60 amino acids in length and be either: (i) an amino acid sequence having from 80% to 100% identity (such as, but not limited to, at least 80% or at least 90% identity) to at least one amino acid sequence as set forth in the group of peptides shown in Tables 1, 3, and 4; or (ii) an antigenic fragment of at least one of the peptides as set forth in Tables 1, 3, and 4.

More particularly, in at least certain embodiments, the carrier molecule composition comprises one, two, or more peptides, wherein each peptide is selected from the group of amino acid sequences of (a)-(i) above. The one, two, or more peptides may be linked to the carrier molecule directly or indirectly via one or more amino acid linker sequences. In at least one embodiment, the carrier molecule composition comprises five, six, seven, eight, nine, ten, or eleven peptides, wherein each peptide is selected from the group of amino acid sequences of (a)-(i) above. The five or more peptides may be linked to the carrier molecule directly or indirectly via one or more amino acid linker sequences.

In a particular embodiment, the carrier molecule composition comprises all the peptides having SEQ ID NOs: 308, 460, 153, 350, 268, 341, 329, 517, 123, and 245; in an alternative embodiment of this carrier molecule composition, one or more antigenic fragment(s) of SEQ ID NOs: 308, 460, 153, 350, 268, 341, 329, 517, 123, and 245 replaces the corresponding peptide. The peptides may be linked to the carrier molecule directly or indirectly via one or more amino acid linker sequences.

Any of the carrier molecule compositions described above or otherwise contemplated herein may be present in a composition that also includes a pharmaceutically acceptable carrier, vehicle, diluent, and/or adjuvant. In addition, any of the carrier molecule compositions described or otherwise contemplated herein may induce an antibody response against at least one or more Nontypeable *Haemophilus influenzae* strains selected from the group including 3655, 6P18H1, 7P49H1, PittAA, PittEE, PittGG, PittHH, PittII, R3021, R2846, R2866, 22.1-21, 22.4-21, 86-028NP, NT127, HI1373, HI1374, HI1388, HI1394, HI1408, HI1417, HI1426, HI1722, HI1974, HI2114 HI2116, and HI2343. In addition to inducing an antibody response against at least one or more NTHi strains, the carrier molecule composition may induce an antibody response against one or more Hi type b strains, including but not limited to, type b strains E1a, 10810, HI689, DL42, and HI701.

In certain embodiments, the present disclosure is directed to a method of inducing in a subject an active immunogenic response against Nontypeable *Haemophilus influenzae*. The method includes the step of administering to a subject an immunogenically-effective amount of any of the peptide compositions, fusion polypeptides, and/or carrier molecule compositions as described above or otherwise contemplated herein, where the method is effective against at least one or more Nontypeable *Haemophilus influenzae* strains selected from the group including 3655, 6P18H1, 7P49H1, PittAA, PittEE, PittGG, PittHH, PittII, R3021, R2846, R2866, 22.1-21, 22.4-21, 86-028NP, NT127, HI1373, HI1374, HI1388, HI1394, HI1408, HI1417, HI1426, HI1722, HI1974, HI2114 HI2116, and HI2343, and in another embodiment additionally against at least one strain of a type b Hi, including but not limited to, type b strains E1a, 10810, HI689, DL42 and HI701.

In certain embodiments, the present disclosure is directed to a method of providing a passive immune protection in a subject against Nontypeable *Haemophilus influenzae*. The method includes the step of administering to a subject an effective amount of an antibody composition raised against any of the immunogenic peptide compositions, fusion polypeptides, and/or carrier molecule compositions as described above or otherwise contemplated herein, where the method is at least partially protective against at least one or more Nontypeable *Haemophilus influenzae* strain selected from the group including 3655, 6P18H1, 7P49H1, PittAA, PittEE, PittGG, PittHH, PittII, R3021, R2846, R2866, 22.1-21, 22.4-21, 86-028NP, NT127, HI1373, HI1374, HI1388, HI1394, HI1408, HI1417, HI1426, HI1722, HI1974, HI2114 HI2116, and HI2343. In another embodiment, the method is additionally at least partially protective against at least one strain of a type b Hi, including but not limited to, type b strains E1a, 10810, HI689, DL42 and HI701.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims. Applicants reserve the right to amend, add to, or replace the claims indicated herein below in subsequent patent applications.

REFERENCES

The following references, to the extent that they provide exemplary procedural or other details supplementary to those set forth herein, are specifically incorporated herein by reference.

1. Nizet V, Colina K F, Almquist J R, *Rubens* C E, Smith A L (1996) A virulent nonencapsulated *Haemophilus influenzae*. J Infect Dis 173: 180-186.
2. Hempel R J, Morton D J, Seale T W, Whitby P W, Stull T L (2013) The role of the RNA chaperone Hfq in *Haemophilus influenzae* pathogenesis. BMC Microbiol 13: 134.
3. Musser J M, Barenkamp S J, Granoff D M, Selander R K (1986) Genetic relationships of serologically nontypable and serotype b strains of *Haemophilus influenzae*. Infect Immun 52: 183-191.
4. Fleischmann R D, Adams M D, White O, Clayton R A, Kirkness E F, et al. (1995) Whole-genome random sequencing and assembly of *Haemophilus influenzae* Rd. Science 269: 496-512.
5. Harrison A, Dyer D W, Gillaspy A, Ray W C, Mungur R, et al. (2005) Genomic sequence of an otitis media isolate of nontypeable *Haemophilus influenzae*: comparative study with *H. influenzae* serotype d, strain KW20. J Bacteriol 187: 4627-4636.
6. Salzberg S L, Delcher A L, Kasif S, White O (1998) Microbial gene identification using interpolated Markov models. Nucleic Acids Res 26: 544-548.
7. Sali A, Blundell T L (1993) Comparative protein modelling by satisfaction of spatial restraints. J Mol Biol 234: 779-815.
8. Fiser A, Do R K, Sali A (2000) Modeling of loops in protein structures. Protein Sci 9: 1753-1773.
9. Bagos P G, Liakopoulos T D, Spyropoulos I C, Hamodrakas S J (2004) PRED-TMBB: a web server for predicting the topology of beta-barrel outer membrane proteins. Nucleic Acids Res 32: W400-W404.
10. Berven F S, Flikka K, Jensen H B, Eidhammer I (2004) BOMP: a program to predict integral beta-barrel outer membrane proteins encoded within genomes of Gram-negative bacteria. Nucleic Acids Res 32: W394-W399.
11. Krogh A, Larsson B, von H G, Sonnhammer E L (2001) Predicting transmembrane protein topology with a hidden Markov model: application to complete genomes. J Mol Biol 305: 567-580. 10.1006/jmbi.2000.4315 [doi]; 50022-2836(00)94315-8 [pii].
12. Pisitkun T, Hoffert J D, Saeed F, Knepper M A (2012) NHLBI-AbDesigner: an online tool for design of peptide-directed antibodies. Am J Physiol Cell Physiol 302: C154-C164.
13. Smith A L, Smith D H, Averill D R, Marino J, Moxon E R (1973) Production of *Haemophilus influenzae* b meningitis in infant rats by intraperitoneal inoculation. Infect Immun 8: 278-290.
14. Seale T W, Morton D J, Whitby P W, Wolf R, Kosanke S D, et al. (2006) Complex role of hemoglobin and hemoglobin-haptoglobin binding proteins in *Haemophilus influenzae* virulence in the infant rat model of invasive infection. Infect Immun 74: 6213-6225.
15. Morton D J, Smith A, Ren Z, Madore L L, VanWagoner T M, et al. (2004) Identification of a haem-utilization protein (Hup) in *Haemophilus influenzae*. Microbiology 150: 3923-3933.
16. Hanson M S, Pelzel S E, Latimer J, Muller-Eberhard U, Hansen E J (1992) Identification of a genetic locus of *Haemophilus influenzae* type b necessary for the binding and utilization of heme bound to human hemopexin. Proc Natl Acad Sci USA 89: 1973-1977.
17. Morton D J, Seale T W, Madore L L, VanWagoner T M, Whitby P W, et al. (2007) The haem-haemopexin utilization gene cluster (hxuCBA) as a virulence factor of *Haemophilus influenzae*. Microbiology 153: 215-224.
18. McCrea K W, Xie J, LaCross N, Patel M, Mukundan D, et al. (2008) Relationships of nontypeable *Haemophilus influenzae* strains to hemolytic and nonhemolytic *Haemophilus haemolyticus* strains. J Clin Microbiol 46: 406-416.
19. Yu N Y, Wagner J R, Laird M R, Melli G, Rey S, et al. (2010) PSORTb 3.0: improved protein subcellular localization prediction with refined localization subcategories and predictive capabilities for all prokaryotes. Bioinformatics 26: 1608-1615.

20. Postle K, Kadner R J (2003) Touch and go: tying TonB to transport. Mol Microbiol 49: 869-882.
21. Wiener M C (2005) TonB-dependent outer membrane transport: going for Baroque? Curr Opin Struct Biol 15: 394-400.
22. St Geme J W, Yeo H J (2009) A prototype two-partner secretion pathway: the *Haemophilus influenzae* HMW1 and HMW2 adhesin systems. Trends Microbiol 17: 355-360.
23. Morton D J, Stull T L (1999) Distribution of a family of *Haemophilus influenzae* genes containing CCAA nucleotide repeating units. FEMS Microbiol Lett 174: 303-309.
24. Hogg J S, Hu F Z, Janto B, Boissy R, Hayes J, et al. (2007) Characterization and modeling of the *Haemophilus influenzae* core- and supra-genomes based on the complete genomic sequences of Rd and 12 clinical non-typeable strains. Genome Biol 8: R103.

What is claimed is:

1. A peptide composition, comprising a plurality of peptides comprising at least two different amino acid sequences, wherein each of the at least two different amino acid sequences is from an externally exposed loop of an outer membrane protein (OMP) selected from the group consisting of:

SEQ ID NO: 97, SEQ ID NO: 101, SEQ ID NO: 589, SEQ ID NO: 462, SEQ ID NO: 590, SEQ ID NO: 308, SEQ ID NO: 123, SEQ ID NO: 139, SEQ ID NO: 245, SEQ ID NO: 460, SEQ ID NO: 328, SEQ ID NO: 329, SEQ ID NO: 153, SEQ ID NO: 321, SEQ ID NO: 325, SEQ ID NO: 145, SEQ ID NO: 350, SEQ ID NO: 268, SEQ ID NO: 341, and SEQ ID NO: 517, wherein each of the peptides induces an antibody response against a Nontypeable *Haemophilus influenzae* (NTHi), each of the peptides is linked together to form a fusion polypeptide, and a peptide at the amino-terminal end of the fusion polypeptide is duplicated at the carboxy terminal end of the fusion polypeptide.

2. The peptide composition of claim 1, wherein the at least two different amino acid sequences are linked to a carrier molecule to form a carrier molecule composition.

3. The peptide composition of claim 1, further defined as being able to induce an antibody response against at least one type b strain of *Haemophilus influenzae*.

4. The peptide composition of claim 1, further comprising a pharmaceutically acceptable carrier, vehicle, diluent, and/or adjuvant.

5. The peptide composition of claim 1, further defined as comprising at least five of said amino acid sequences.

6. The peptide composition of claim 5, wherein the at least five amino acid sequences are linked to a carrier molecule to form a carrier molecule composition.

7. The peptide composition of claim 1, wherein the at least two different amino acid sequences comprise:
SEQ ID NO: 328 from an outer membrane (OM) protein assembly factor BamA; and
SEQ ID NO: 462 and/or SEQ ID NO: 590 from an outer membrane protein P4 designated Hel.

8. The peptide composition of claim 1, wherein the at least two different amino acid sequences comprise:

SEQ ID NO: 328 from an OM protein assembly factor designated BamA; and

SEQ ID NO: 145 from a 5'-nucleotidase designated NucA.

9. The peptide composition of claim 1, wherein the at least two different amino acid sequences comprise:

SEQ ID NO: 328 from an OM protein assembly factor designated BamA; and

SEQ ID NO: 321 and/or SEQ ID NO: 325 from a lipopolysaccharide (LPS) assembly outer membrane (OM) complex LptDE component protein designated 1ptE.

10. The peptide composition of claim 1, wherein the at least two different amino acid sequences comprise:

SEQ ID NO: 328 from an OM protein assembly factor designated BamA; and

SEQ ID NO: 139 from a lipoprotein designated N1pI.

11. A peptide composition, comprising a plurality of peptides comprising at least two different amino acid sequences, wherein each of the at least two different amino acid sequences is from an externally exposed loop of an outer membrane protein (OMP) and at least one of the amino acid sequences is SEQ ID NO: 328, and wherein each of the peptides induces an antibody response against a Nontypeable *Haemophilus influenzae* (NTHi), each of the peptides is linked together to form a fusion polypeptide, and a peptide at the amino-terminal end of the fusion polypeptide is duplicated at the carboxy terminal end of the fusion polypeptide.

12. The peptide composition of claim 11, wherein the peptide composition further comprises peptides having amino acid sequences SEQ ID NO: 462, SEQ ID NO: 590, and SEQ ID NO: 145.

13. The peptide composition of claim 11, wherein the peptide composition further comprises peptides having amino acid sequences SEQ ID NO: 321 and SEQ ID NO: 139.

14. The peptide composition of claim 11, wherein the peptide composition further comprises peptides having amino acid sequences SEQ ID NO: 462, SEQ ID NO: 590, SEQ ID NO: 145, SEQ ID NO: 321, and SEQ ID NO: 139.

15. A method of inducing an immunogenic response in a subject, comprising the step of:

administering to the subject an amount of a peptide composition which is effective in stimulating an immunogenic response against Nontypeable *Haemophilus influenza* (NTHi) in the subject, wherein the peptide composition comprises at least two different amino acid sequences, wherein each the at least two different amino acid sequences is from an externally exposed loop of an outer membrane protein (OMP) selected from the group consisting of:

SEQ ID NO: 97, SEQ ID NO: 101, SEQ ID NO: 589, SEQ ID NO: 462, SEQ ID NO: 590, SEQ ID NO: 308, SEQ ID NO: 123, SEQ ID NO: 139, SEQ ID NO: 245, SEQ ID NO: 460, SEQ ID NO: 328, SEQ ID NO: 329, SEQ ID NO: 153, SEQ ID NO: 321, SEQ ID NO: 325, SEQ ID NO: 145, SEQ ID NO: 350, SEQ ID NO: 268, SEQ ID NO: 341, and SEQ ID NO: 517, and wherein each of the at least two different amino acid sequences is able to induce an antibody response against NTHi, each of the peptides is linked together to form a fusion polypeptide, and a peptide at the amino-terminal end of the fusion polypeptide is duplicated at the carboxy terminal end of the fusion polypeptide.

16. The method of claim 15, wherein the peptide composition is also effective in inducing an antibody response against at least one type b strain of *Haemophilus influenzae*.

17. The method of claim 15, wherein the peptide composition comprises at least five of said amino acid sequences.

18. The method of claim 17, wherein the at least five amino acid sequences of the peptide composition are linked to a carrier molecule to form a carrier molecule composition.

* * * * *

SEQUENCE LISTING

```
<160> NUMBER OF SEQ ID NOS: 591

<210> SEQ ID NO 1
<211> LENGTH: 20
<212> TYPE: PRT
<213> ORGANISM: Haemophilus influenzae

<400> SEQUENCE: 1

Thr Leu Asn Lys Asp Asp Gly Val Tyr Tyr Leu Asn Gly Ser Gln Ser
1               5                   10                  15

Gly Lys Gly Gln
            20

<210> SEQ ID NO 2
<211> LENGTH: 20
<212> TYPE: PRT
<213> ORGANISM: Haemophilus influenzae

<400> SEQUENCE: 2

Thr Leu Asn Lys Asp Asp Gly Ile Tyr Tyr Leu Asn Gly Ser Gln Ser
1               5                   10                  15

Gly Lys Gly Gln
            20

<210> SEQ ID NO 3
<211> LENGTH: 33
<212> TYPE: PRT
<213> ORGANISM: Haemophilus influenzae

<400> SEQUENCE: 3

Leu Thr Leu Asn Lys Asp Asp Gly Val Tyr Tyr Leu Asn Gly Ser Gln
1               5                   10                  15

Ser Gly Lys Gly Gln Val Ala Gly Asn Leu Thr Thr Asn Glu Pro His
            20                  25                  30

Leu

<210> SEQ ID NO 4
<211> LENGTH: 33
<212> TYPE: PRT
<213> ORGANISM: Haemophilus influenzae

<400> SEQUENCE: 4

Leu Thr Leu Asn Lys Asp Glu Gly Ile Tyr Tyr Leu Asn Gly Gly Gln
1               5                   10                  15

Ser Gly Lys Gly Gln Val Ala Gly Asn Leu Ala Thr Asn Glu Pro His
            20                  25                  30

Leu

<210> SEQ ID NO 5
<211> LENGTH: 33
<212> TYPE: PRT
<213> ORGANISM: Haemophilus influenzae
```

-continued

<400> SEQUENCE: 5

Leu Thr Leu Asn Lys Asp Glu Gly Ile Tyr Tyr Leu Asn Gly Gly Gln
1               5                   10                  15

Ser Gly Lys Gly Gln Val Ala Gly Asn Leu Thr Thr Asn Glu Pro His
            20                  25                  30

Leu

<210> SEQ ID NO 6
<211> LENGTH: 33
<212> TYPE: PRT
<213> ORGANISM: Haemophilus influenzae

<400> SEQUENCE: 6

Leu Thr Leu Asn Lys Asp Glu Gly Ile Tyr Tyr Leu Asn Gly Gly Leu
1               5                   10                  15

Ser Gly Lys Gly Gln Val Ala Gly Asn Leu Thr Thr Asn Glu Pro His
            20                  25                  30

Leu

<210> SEQ ID NO 7
<211> LENGTH: 33
<212> TYPE: PRT
<213> ORGANISM: Haemophilus influenzae

<400> SEQUENCE: 7

Leu Thr Leu Asn Lys Asp Glu Gly Ile Tyr Tyr Leu Asn Gly Gly Leu
1               5                   10                  15

Ser Gly Lys Glu Gln Val Ala Gly Asn Leu Thr Thr Asn Glu Pro His
            20                  25                  30

Leu

<210> SEQ ID NO 8
<211> LENGTH: 33
<212> TYPE: PRT
<213> ORGANISM: Haemophilus influenzae

<400> SEQUENCE: 8

Leu Thr Leu Asn Lys Asp Glu Gly Ile Tyr Tyr Leu Asn Cys Ser Gln
1               5                   10                  15

Ser Gly Lys Gly Gln Val Ala Gly Asn Leu Thr Thr Asn Glu Pro His
            20                  25                  30

Leu

<210> SEQ ID NO 9
<211> LENGTH: 19
<212> TYPE: PRT
<213> ORGANISM: Haemophilus influenzae

<400> SEQUENCE: 9

Asn Pro Lys Thr Asp Asn Glu Cys Phe Phe Ile Arg Leu Ser Gln Ala
1               5                   10                  15

Pro Leu Ala

<210> SEQ ID NO 10
<211> LENGTH: 19
<212> TYPE: PRT
<213> ORGANISM: Haemophilus influenzae

<400> SEQUENCE: 10

Asn Pro Lys Thr Asp Asn Glu Arg Phe Phe Ile Arg Leu Ser Gln Ala
1               5                   10                  15

Pro Leu Ala

<210> SEQ ID NO 11
<211> LENGTH: 30
<212> TYPE: PRT
<213> ORGANISM: Haemophilus influenzae

<400> SEQUENCE: 11

Thr Thr Gly Ser Gly Ser Leu Leu Ser Pro Asp Gly Ser Ile Thr Phe
1               5                   10                  15

Asp Asp Arg Ser Asn Leu Leu Val Ile Gln Asp Glu Pro Arg
            20                  25                  30

<210> SEQ ID NO 12
<211> LENGTH: 30
<212> TYPE: PRT
<213> ORGANISM: Haemophilus influenzae

<400> SEQUENCE: 12

Thr Thr Gly Ser Gly Ser Leu Leu Ser Pro Ala Gly Ser Ile Thr Phe
1               5                   10                  15

Asp Asp Arg Ser Asn Leu Leu Val Ile Gln Asp Glu Pro Arg
            20                  25                  30

<210> SEQ ID NO 13
<211> LENGTH: 30
<212> TYPE: PRT
<213> ORGANISM: Haemophilus influenzae

<400> SEQUENCE: 13

Thr Thr Gly Ser Gly Ser Leu Leu Ser Pro Val Gly Ser Ile Thr Phe
1               5                   10                  15

Asp Asp Arg Ser Asn Leu Leu Val Ile Gln Asp Glu Pro Arg
            20                  25                  30

<210> SEQ ID NO 14
<211> LENGTH: 30
<212> TYPE: PRT
<213> ORGANISM: Haemophilus influenzae

<400> SEQUENCE: 14

Thr Thr Gly Ser Gly Ser Leu Leu Ser Ser Ala Gly Ser Ile Thr Phe
1               5                   10                  15

Asp Asp Arg Ser Asn Leu Leu Val Ile Gln Asp Glu Pro Arg
            20                  25                  30

<210> SEQ ID NO 15
<211> LENGTH: 11
<212> TYPE: PRT
<213> ORGANISM: Haemophilus influenzae

<400> SEQUENCE: 15

Gly Ser Ala Ser Gln Arg Asn Val Val Pro Gly
1               5                   10

<210> SEQ ID NO 16
<211> LENGTH: 11
<212> TYPE: PRT
<213> ORGANISM: Haemophilus influenzae

```
<400> SEQUENCE: 16

Gly Ser Ala Ser Glu Arg Asn Val Val Pro Gly
1               5                   10

<210> SEQ ID NO 17
<211> LENGTH: 11
<212> TYPE: PRT
<213> ORGANISM: Haemophilus influenzae

<400> SEQUENCE: 17

Gly Ser Ala Ser Ala Arg Asn Val Val Pro Gly
1               5                   10

<210> SEQ ID NO 18
<211> LENGTH: 11
<212> TYPE: PRT
<213> ORGANISM: Haemophilus influenzae

<400> SEQUENCE: 18

Gly Ser Ala Ser Gln Arg Asn Val Ile Pro Gly
1               5                   10

<210> SEQ ID NO 19
<211> LENGTH: 14
<212> TYPE: PRT
<213> ORGANISM: Haemophilus influenzae

<400> SEQUENCE: 19

Glu Tyr Asp Asp Ser Tyr Asp Ala Gly Ile Phe Gly Gly Lys
1               5                   10

<210> SEQ ID NO 20
<211> LENGTH: 14
<212> TYPE: PRT
<213> ORGANISM: Haemophilus influenzae

<400> SEQUENCE: 20

Lys Tyr Asp Asp Ser Tyr Asp Ala Gly Ile Phe Gly Gly Lys
1               5                   10

<210> SEQ ID NO 21
<211> LENGTH: 14
<212> TYPE: PRT
<213> ORGANISM: Haemophilus influenzae

<400> SEQUENCE: 21

Lys Tyr Asp Asp Ser Tyr Asp Ala Gly Val Phe Gly Gly Lys
1               5                   10

<210> SEQ ID NO 22
<211> LENGTH: 14
<212> TYPE: PRT
<213> ORGANISM: Haemophilus influenzae

<400> SEQUENCE: 22

Glu Tyr Gly Asp Ser Tyr Asn Ala Gly Ile Phe Gly Gly Lys
1               5                   10

<210> SEQ ID NO 23
<211> LENGTH: 14
<212> TYPE: PRT
<213> ORGANISM: Haemophilus influenzae

<400> SEQUENCE: 23
```

Glu Tyr Gly Asp Ser Tyr Asn Ala Gly Val Phe Gly Gly Lys
1               5                   10

<210> SEQ ID NO 24
<211> LENGTH: 13
<212> TYPE: PRT
<213> ORGANISM: Haemophilus influenzae

<400> SEQUENCE: 24

Ser Lys Asp Lys Ser Val Val Ser Leu Gln Asp Arg Ala
1               5                   10

<210> SEQ ID NO 25
<211> LENGTH: 13
<212> TYPE: PRT
<213> ORGANISM: Haemophilus influenzae

<400> SEQUENCE: 25

Ser Gln Asp Lys Ser Val Val Ser Leu Gln Asp Arg Ala
1               5                   10

<210> SEQ ID NO 26
<211> LENGTH: 13
<212> TYPE: PRT
<213> ORGANISM: Haemophilus influenzae

<400> SEQUENCE: 26

Ser Lys Asp Thr Ser Val Val Ser Leu Gln Asp Arg Ala
1               5                   10

<210> SEQ ID NO 27
<211> LENGTH: 13
<212> TYPE: PRT
<213> ORGANISM: Haemophilus influenzae

<400> SEQUENCE: 27

Ser Lys Asp Lys Ser Val Val Ser Leu Gln Asp Lys Ala
1               5                   10

<210> SEQ ID NO 28
<211> LENGTH: 13
<212> TYPE: PRT
<213> ORGANISM: Haemophilus influenzae

<400> SEQUENCE: 28

Ser Lys Asp Thr Ser Val Val Ser Leu Gln Asp Ser Ala
1               5                   10

<210> SEQ ID NO 29
<211> LENGTH: 13
<212> TYPE: PRT
<213> ORGANISM: Haemophilus influenzae

<400> SEQUENCE: 29

Lys Val Asp Ile Asp Phe Thr Asp Arg Thr Ala Thr Ser
1               5                   10

<210> SEQ ID NO 30
<211> LENGTH: 13
<212> TYPE: PRT
<213> ORGANISM: Haemophilus influenzae

<400> SEQUENCE: 30

Lys Val Asp Ile Asp Phe Thr Asp Arg Thr Ala Ser Ser
1               5                   10

<210> SEQ ID NO 31
<211> LENGTH: 13
<212> TYPE: PRT
<213> ORGANISM: Haemophilus influenzae

<400> SEQUENCE: 31

Lys Val Asp Ile Asp Phe Ala Asp Arg Thr Ala Thr Ser
1               5                   10

<210> SEQ ID NO 32
<211> LENGTH: 25
<212> TYPE: PRT
<213> ORGANISM: Haemophilus influenzae

<400> SEQUENCE: 32

Trp Ser Arg Leu Thr Lys Leu His Ala Ser Phe Glu Asp Gly Lys Lys
1               5                   10                  15

Ala Phe Asp Lys Glu Leu Gln Tyr Ser
            20                  25

<210> SEQ ID NO 33
<211> LENGTH: 25
<212> TYPE: PRT
<213> ORGANISM: Haemophilus influenzae

<400> SEQUENCE: 33

Trp Ser Arg Leu Thr Lys Leu Asn Ala Ser Phe Glu Asp Gly Lys Lys
1               5                   10                  15

Ala Phe Asp Lys Glu Leu Gln Tyr Ser
            20                  25

<210> SEQ ID NO 34
<211> LENGTH: 25
<212> TYPE: PRT
<213> ORGANISM: Haemophilus influenzae

<400> SEQUENCE: 34

Trp Ser Arg Leu Thr Lys Leu His Ala Ser Phe Glu Asn Gly Lys Lys
1               5                   10                  15

Ala Phe Asp Lys Glu Leu Gln Tyr Ser
            20                  25

<210> SEQ ID NO 35
<211> LENGTH: 25
<212> TYPE: PRT
<213> ORGANISM: Haemophilus influenzae

<400> SEQUENCE: 35

Trp Ser Arg Leu Thr Arg Leu Tyr Ala Ser Ser Glu Asn Gly Lys Lys
1               5                   10                  15

Ala Phe Asp Lys Glu Leu Gln Tyr Ser
            20                  25

<210> SEQ ID NO 36
<211> LENGTH: 25
<212> TYPE: PRT
<213> ORGANISM: Haemophilus influenzae

<400> SEQUENCE: 36

Trp Ser Arg Leu Thr Lys Leu Asn Ala Asn Phe Glu Asp Gly Lys Lys
1               5                   10                  15

Ala Phe Asp Lys Glu Leu Gln Tyr Ser
            20                  25

<210> SEQ ID NO 37
<211> LENGTH: 25
<212> TYPE: PRT
<213> ORGANISM: Haemophilus influenzae

<400> SEQUENCE: 37

Trp Ser Arg Leu Thr Lys Leu His Ala Ser Tyr Glu Asn Gly Glu Lys
1               5                   10                  15

Ala Phe Asp Lys Glu Leu Gln Tyr Ser
            20                  25

<210> SEQ ID NO 38
<211> LENGTH: 25
<212> TYPE: PRT
<213> ORGANISM: Haemophilus influenzae

<400> SEQUENCE: 38

Trp Ser Arg Leu Thr Lys Leu His Ala Ser Phe Glu Asp Gly Lys Lys
1               5                   10                  15

Ala Phe Glu Lys Glu Leu Gln Tyr Ser
            20                  25

<210> SEQ ID NO 39
<211> LENGTH: 19
<212> TYPE: PRT
<213> ORGANISM: Haemophilus influenzae

<400> SEQUENCE: 39

Asp Gln Ala Ala Ser Arg His His Arg Ser Ala Ala Ile Pro Asp Thr
1               5                   10                  15

Asp Arg Thr

<210> SEQ ID NO 40
<211> LENGTH: 19
<212> TYPE: PRT
<213> ORGANISM: Haemophilus influenzae

<400> SEQUENCE: 40

Asp Gln Ala Ala Ser Arg His Gln Arg Ser Ala Ala Ile Pro Asp Thr
1               5                   10                  15

Asp Arg Thr

<210> SEQ ID NO 41
<211> LENGTH: 19
<212> TYPE: PRT
<213> ORGANISM: Haemophilus influenzae

<400> SEQUENCE: 41

Asp Gln Ala Ala Ser Arg His Gln Arg Ser Ala Ala Ile Pro Asp Thr
1               5                   10                  15

Asn Arg Thr

<210> SEQ ID NO 42
<211> LENGTH: 11
<212> TYPE: PRT
<213> ORGANISM: Haemophilus influenzae

<400> SEQUENCE: 42

Thr Thr Ala Asn Tyr Thr Ser Gln Ala His Ala

```
<210> SEQ ID NO 43
<211> LENGTH: 11
<212> TYPE: PRT
<213> ORGANISM: Haemophilus influenzae

<400> SEQUENCE: 43

Ser Thr Ala Asn Tyr Thr Ser Gln Ala His Ala
1               5                   10

<210> SEQ ID NO 44
<211> LENGTH: 11
<212> TYPE: PRT
<213> ORGANISM: Haemophilus influenzae

<400> SEQUENCE: 44

Ala Thr Ala Asn Tyr Thr Ser Gln Ala His Ala
1               5                   10

<210> SEQ ID NO 45
<211> LENGTH: 11
<212> TYPE: PRT
<213> ORGANISM: Haemophilus influenzae

<400> SEQUENCE: 45

Thr Asn Ala Asn Tyr Thr Ser Gln Ala His Ala
1               5                   10

<210> SEQ ID NO 46
<211> LENGTH: 32
<212> TYPE: PRT
<213> ORGANISM: Haemophilus influenzae

<400> SEQUENCE: 46

Lys Val Leu Val Glu Gly Asn Thr Asp Glu Arg Gly Thr Pro Glu Tyr
1               5                   10                  15

Asn Ile Ala Leu Gly Gln Arg Arg Ala Asp Ala Val Lys Gly Tyr Leu
            20                  25                  30

<210> SEQ ID NO 47
<211> LENGTH: 39
<212> TYPE: PRT
<213> ORGANISM: Haemophilus influenzae

<400> SEQUENCE: 47

Gly Lys Gly Val Asp Ala Gly Lys Leu Gly Thr Val Ser Tyr Gly Glu
1               5                   10                  15

Glu Lys Pro Ala Val Leu Gly His Asp Glu Ala Ala Tyr Ser Lys Asn
            20                  25                  30

Arg Arg Ala Val Leu Ala Tyr
        35

<210> SEQ ID NO 48
<211> LENGTH: 22
<212> TYPE: PRT
<213> ORGANISM: Haemophilus influenzae

<400> SEQUENCE: 48

Thr Ile Ser Lys Gln Leu Ser Ala Val Ile Phe Pro Phe Ile Phe Ser
1               5                   10                  15

Ala Cys Val Ser Gln Ser
            20
```

<210> SEQ ID NO 49
<211> LENGTH: 31
<212> TYPE: PRT
<213> ORGANISM: Haemophilus influenzae

<400> SEQUENCE: 49

Leu Ser Tyr Leu Gln Gln Asn Asn Pro Gln Leu Ala Lys Ile Asn Leu
1               5                   10                  15

Asp Lys Ala Leu Gln His Asp Lys Asn Tyr Tyr Leu Val His Ser
            20                  25                  30

<210> SEQ ID NO 50
<211> LENGTH: 31
<212> TYPE: PRT
<213> ORGANISM: Haemophilus influenzae

<400> SEQUENCE: 50

Leu Ser Tyr Leu Gln Gln Asn Asn Pro Gln Leu Ala Lys Ile Asn Leu
1               5                   10                  15

Asp Lys Ala Leu Leu His Asp Lys Asn Tyr Tyr Leu Val His Ser
            20                  25                  30

<210> SEQ ID NO 51
<211> LENGTH: 31
<212> TYPE: PRT
<213> ORGANISM: Haemophilus influenzae

<400> SEQUENCE: 51

Leu Ser Tyr Leu Gln Gln Asn Asn Pro Gln Leu Ala Lys Ile Asn Leu
1               5                   10                  15

Asp Asn Ala Leu Gln His Asp Lys Asn Tyr Tyr Leu Val His Ser
            20                  25                  30

<210> SEQ ID NO 52
<211> LENGTH: 36
<212> TYPE: PRT
<213> ORGANISM: Haemophilus influenzae

<400> SEQUENCE: 52

Arg Glu Tyr Glu Ile Ala Val Lys Leu Asn His Lys Gln Gly Asp Val
1               5                   10                  15

His Asn Asn Phe Gly Thr Phe Leu Cys Ser Gln Lys Lys Phe Glu Gln
            20                  25                  30

Ala Gln Gln Gln
        35

<210> SEQ ID NO 53
<211> LENGTH: 36
<212> TYPE: PRT
<213> ORGANISM: Haemophilus influenzae

<400> SEQUENCE: 53

Arg Glu Tyr Glu Ile Ala Val Asn Leu Asn His Lys Gln Gly Asp Val
1               5                   10                  15

His Asn Asn Phe Gly Thr Phe Leu Cys Ser Gln Lys Lys Phe Glu Gln
            20                  25                  30

Ala Gln Gln Gln
        35

<210> SEQ ID NO 54

```
<211> LENGTH: 36
<212> TYPE: PRT
<213> ORGANISM: Haemophilus influenzae

<400> SEQUENCE: 54

Arg Glu Tyr Glu Ile Ala Val Asn Leu Asn Tyr Lys Gln Gly Asp Val
1               5                   10                  15

His Asn Asn Phe Gly Thr Phe Leu Cys Ser Gln Lys Lys Phe Glu Gln
            20                  25                  30

Ala Gln Gln Gln
        35

<210> SEQ ID NO 55
<211> LENGTH: 26
<212> TYPE: PRT
<213> ORGANISM: Haemophilus influenzae

<400> SEQUENCE: 55

Met Asp Ile Tyr Gln Gln Thr Leu Glu Lys Leu Arg Gln Ile Asp Gly
1               5                   10                  15

Lys Arg Ala Glu Lys Phe Asn Ser Leu Lys
            20                  25

<210> SEQ ID NO 56
<211> LENGTH: 26
<212> TYPE: PRT
<213> ORGANISM: Haemophilus influenzae

<400> SEQUENCE: 56

Met Asp Ile Tyr Gln Gln Thr Leu Glu Lys Leu Arg Gln Ile Asn Gly
1               5                   10                  15

Lys Arg Ala Glu Lys Phe Asn Ser Leu Lys
            20                  25

<210> SEQ ID NO 57
<211> LENGTH: 25
<212> TYPE: PRT
<213> ORGANISM: Haemophilus influenzae

<400> SEQUENCE: 57

Gln Lys Met Gln Val Glu Lys Val Asp Lys Ala Leu Gln Lys Gly Glu
1               5                   10                  15

Ala Asp Arg Tyr Leu Cys Gln Asp Asp
            20                  25

<210> SEQ ID NO 58
<211> LENGTH: 37
<212> TYPE: PRT
<213> ORGANISM: Haemophilus influenzae

<400> SEQUENCE: 58

Ser Glu Lys Leu Thr Leu Met Ile Ser Glu Arg Gly Lys Asn Tyr Ala
1               5                   10                  15

Asn Ile Arg Trp Met Trp Gln Glu Arg Asp Asp Phe Ser Thr Leu Lys
            20                  25                  30

Thr Asn Leu Gly Glu
        35

<210> SEQ ID NO 59
<211> LENGTH: 37
<212> TYPE: PRT
<213> ORGANISM: Haemophilus influenzae
```

<400> SEQUENCE: 59

Ser Glu Lys Leu Thr Leu Met Ile Ser Glu Arg Gly Lys Asn Tyr Ala
1               5                   10                  15

Asn Ile Arg Trp Met Trp Gln Glu Arg Asp Asp Phe Ser Met Leu Lys
            20                  25                  30

Thr Asn Leu Gly Glu
            35

<210> SEQ ID NO 60
<211> LENGTH: 13
<212> TYPE: PRT
<213> ORGANISM: Haemophilus influenzae

<400> SEQUENCE: 60

Gln Thr Asn Phe Gln Gln Arg Lys Glu Pro Thr Phe Gly
1               5                   10

<210> SEQ ID NO 61
<211> LENGTH: 12
<212> TYPE: PRT
<213> ORGANISM: Haemophilus influenzae

<400> SEQUENCE: 61

Thr Glu Glu Asn Ile Ser Ala Val Asp Glu Glu Ile
1               5                   10

<210> SEQ ID NO 62
<211> LENGTH: 16
<212> TYPE: PRT
<213> ORGANISM: Haemophilus influenzae

<400> SEQUENCE: 62

Val Glu Lys Ala Glu Lys Pro Ile Leu Ala Gln Pro Glu Lys Trp Lys
1               5                   10                  15

<210> SEQ ID NO 63
<211> LENGTH: 10
<212> TYPE: PRT
<213> ORGANISM: Haemophilus influenzae

<400> SEQUENCE: 63

Leu Pro Ala Lys His Arg Arg Leu Phe Met
1               5                   10

<210> SEQ ID NO 64
<211> LENGTH: 29
<212> TYPE: PRT
<213> ORGANISM: Haemophilus influenzae

<400> SEQUENCE: 64

Val Leu Val Ile Leu Leu Ile Ile Phe Phe Ala Leu Lys Pro Ser Ser
1               5                   10                  15

Asp Thr Val Glu Ser Phe Thr Gln Ser Asn Ser Asn Glu
            20                  25

<210> SEQ ID NO 65
<211> LENGTH: 17
<212> TYPE: PRT
<213> ORGANISM: Haemophilus influenzae

<400> SEQUENCE: 65

Phe Arg Asp Asn Gln Leu Asn Ile Ser Asp Val Asn Ala Met Ser Lys

<210> SEQ ID NO 66
<211> LENGTH: 32
<212> TYPE: PRT
<213> ORGANISM: Haemophilus influenzae

<400> SEQUENCE: 66

Gly Ala Gly Asn Val Leu Ser Ser Phe Lys Ser Gly Asp Lys Val Thr
1               5                   10                  15
Val Ser Val Asn Asn Gln Gly Arg Val Asn Glu Met Arg Leu Ser Asn
            20                  25                  30

<210> SEQ ID NO 67
<211> LENGTH: 32
<212> TYPE: PRT
<213> ORGANISM: Haemophilus influenzae

<400> SEQUENCE: 67

Gly Ala Gly Asn Val Leu Ser Asn Phe Lys Ser Gly Asp Lys Val Thr
1               5                   10                  15
Val Ser Val Asn Asn Gln Gly Arg Val Asn Glu Met Arg Leu Ser Asn
            20                  25                  30

<210> SEQ ID NO 68
<211> LENGTH: 22
<212> TYPE: PRT
<213> ORGANISM: Haemophilus influenzae

<400> SEQUENCE: 68

Val Ser Glu Leu Leu Gln Ala Ser Ala Pro Tyr Lys Ala Asp Val Glu
1               5                   10                  15
Leu Cys Val Tyr Ser Thr
            20

<210> SEQ ID NO 69
<211> LENGTH: 22
<212> TYPE: PRT
<213> ORGANISM: Haemophilus influenzae

<400> SEQUENCE: 69

Val Ser Glu Leu Leu Gln Ala Ser Ala Pro Tyr Lys Ser Asp Val Glu
1               5                   10                  15
Leu Cys Val Tyr Ser Thr
            20

<210> SEQ ID NO 70
<211> LENGTH: 10
<212> TYPE: PRT
<213> ORGANISM: Haemophilus influenzae

<400> SEQUENCE: 70

Asn Gln Gly Asn Lys Tyr Thr Gly Arg Tyr
1               5                   10

<210> SEQ ID NO 71
<211> LENGTH: 19
<212> TYPE: PRT
<213> ORGANISM: Haemophilus influenzae

<400> SEQUENCE: 71

Thr Ala Asn Tyr Leu Asp Tyr Lys Leu Gly Gly Asn Phe Lys Ser Leu
1               5                   10                  15

Gln Ser Gln

<210> SEQ ID NO 72
<211> LENGTH: 19
<212> TYPE: PRT
<213> ORGANISM: Haemophilus influenzae

<400> SEQUENCE: 72

Thr Ala Asn Tyr Leu His Tyr Lys Leu Gly Gly Asn Phe Lys Ser Leu
1               5                   10                  15

Gln Ser Gln

<210> SEQ ID NO 73
<211> LENGTH: 11
<212> TYPE: PRT
<213> ORGANISM: Haemophilus influenzae

<400> SEQUENCE: 73

Gln Gln Ala Val Tyr Ala Lys Gln Lys Arg Lys
1               5                   10

<210> SEQ ID NO 74
<211> LENGTH: 11
<212> TYPE: PRT
<213> ORGANISM: Haemophilus influenzae

<400> SEQUENCE: 74

Gln Gln Ala Val Asn Val Lys Gln Lys Arg Lys
1               5                   10

<210> SEQ ID NO 75
<211> LENGTH: 11
<212> TYPE: PRT
<213> ORGANISM: Haemophilus influenzae

<400> SEQUENCE: 75

Gln Gln Ala Val Tyr Val Lys Gln Lys Arg Lys
1               5                   10

<210> SEQ ID NO 76
<211> LENGTH: 11
<212> TYPE: PRT
<213> ORGANISM: Haemophilus influenzae

<400> SEQUENCE: 76

Gln Gln Ala Val Thr Val Lys Gln Lys Arg Lys
1               5                   10

<210> SEQ ID NO 77
<211> LENGTH: 11
<212> TYPE: PRT
<213> ORGANISM: Haemophilus influenzae

<400> SEQUENCE: 77

Gln Gln Ala Val Ser Val Lys Gln Lys Arg Lys
1               5                   10

<210> SEQ ID NO 78
<211> LENGTH: 11
<212> TYPE: PRT
<213> ORGANISM: Haemophilus influenzae

```
<400> SEQUENCE: 78

Gln Gln Ala Ala Thr Ala Lys Gln Lys Arg Lys
1               5                   10

<210> SEQ ID NO 79
<211> LENGTH: 11
<212> TYPE: PRT
<213> ORGANISM: Haemophilus influenzae

<400> SEQUENCE: 79

Gln Gln Ala Val Asp Ala Lys Gln Lys Arg Lys
1               5                   10

<210> SEQ ID NO 80
<211> LENGTH: 10
<212> TYPE: PRT
<213> ORGANISM: Haemophilus influenzae

<400> SEQUENCE: 80

Gly Asn Leu Ala Asn Gln Thr Ser Glu Lys
1               5                   10

<210> SEQ ID NO 81
<211> LENGTH: 10
<212> TYPE: PRT
<213> ORGANISM: Haemophilus influenzae

<400> SEQUENCE: 81

Gly Asn Leu Ala Asn Gln Thr Asn Glu Lys
1               5                   10

<210> SEQ ID NO 82
<211> LENGTH: 10
<212> TYPE: PRT
<213> ORGANISM: Haemophilus influenzae

<400> SEQUENCE: 82

Gly Asn Leu Ala Asn Gln Thr Ser Glu Gln
1               5                   10

<210> SEQ ID NO 83
<211> LENGTH: 10
<212> TYPE: PRT
<213> ORGANISM: Haemophilus influenzae

<400> SEQUENCE: 83

Gly Asn Leu Ala Asn Gln Thr Asn Glu Gln
1               5                   10

<210> SEQ ID NO 84
<211> LENGTH: 10
<212> TYPE: PRT
<213> ORGANISM: Haemophilus influenzae

<400> SEQUENCE: 84

Gly Asn Leu Ala Asn Gln Thr Asn Glu Thr
1               5                   10

<210> SEQ ID NO 85
<211> LENGTH: 10
<212> TYPE: PRT
<213> ORGANISM: Haemophilus influenzae

<400> SEQUENCE: 85
```

-continued

Gly Asn Leu Ala Asn Gln Thr Asn Glu Arg
1               5                   10

<210> SEQ ID NO 86
<211> LENGTH: 19
<212> TYPE: PRT
<213> ORGANISM: Haemophilus influenzae

<400> SEQUENCE: 86

Gln Phe Ala Asp Lys Thr Leu Glu Ser Ser Gln Lys Met Leu Leu Gly
1               5                   10                  15

Gly Leu Ser

<210> SEQ ID NO 87
<211> LENGTH: 19
<212> TYPE: PRT
<213> ORGANISM: Haemophilus influenzae

<400> SEQUENCE: 87

Gln Phe Ala Asp Lys Asn Leu Glu Ser Ser Gln Lys Thr Leu Leu Gly
1               5                   10                  15

Gly Leu Ser

<210> SEQ ID NO 88
<211> LENGTH: 19
<212> TYPE: PRT
<213> ORGANISM: Haemophilus influenzae

<400> SEQUENCE: 88

Gln Phe Ala Asp Lys Asn Leu Glu Ser Ser Gln Lys Met Leu Leu Gly
1               5                   10                  15

Gly Leu Ser

<210> SEQ ID NO 89
<211> LENGTH: 14
<212> TYPE: PRT
<213> ORGANISM: Haemophilus influenzae

<400> SEQUENCE: 89

Lys Pro Leu Asp Asn Asn Ile Asn Asn Ala Asp Lys His Gln
1               5                   10

<210> SEQ ID NO 90
<211> LENGTH: 14
<212> TYPE: PRT
<213> ORGANISM: Haemophilus influenzae

<400> SEQUENCE: 90

Lys Pro Leu Asp Asn Asn Ile Asp Asn Ala Asp Lys His Gln
1               5                   10

<210> SEQ ID NO 91
<211> LENGTH: 14
<212> TYPE: PRT
<213> ORGANISM: Haemophilus influenzae

<400> SEQUENCE: 91

Lys Pro Leu Asp Asn Asn Ile Asp Asn Thr Asp Lys His Gln
1               5                   10

<210> SEQ ID NO 92
<211> LENGTH: 10
<212> TYPE: PRT

<213> ORGANISM: Haemophilus influenzae

<400> SEQUENCE: 92

Asp Asn Leu Arg Thr Gly Lys Gly Asn Lys
1               5                   10

<210> SEQ ID NO 93
<211> LENGTH: 10
<212> TYPE: PRT
<213> ORGANISM: Haemophilus influenzae

<400> SEQUENCE: 93

Asp Asn Leu Arg Ile Gly Lys Gly Asn Lys
1               5                   10

<210> SEQ ID NO 94
<211> LENGTH: 19
<212> TYPE: PRT
<213> ORGANISM: Haemophilus influenzae

<400> SEQUENCE: 94

Lys Gln Thr Ala Pro Ser Asn Asn Glu Val Glu Val Glu Leu Thr Trp
1               5                   10                  15

Glu Gln Ile

<210> SEQ ID NO 95
<211> LENGTH: 19
<212> TYPE: PRT
<213> ORGANISM: Haemophilus influenzae

<400> SEQUENCE: 95

Lys Gln Thr Ala Pro Ser Asn Asn Glu Val Glu Val Glu Leu Thr Trp
1               5                   10                  15

Glu Lys Ile

<210> SEQ ID NO 96
<211> LENGTH: 19
<212> TYPE: PRT
<213> ORGANISM: Haemophilus influenzae

<400> SEQUENCE: 96

Lys Gln Thr Ala Pro Gly Asn Asn Glu Ala Lys Val Glu Leu Thr Trp
1               5                   10                  15

Glu Gln Ile

<210> SEQ ID NO 97
<211> LENGTH: 14
<212> TYPE: PRT
<213> ORGANISM: Haemophilus influenzae

<400> SEQUENCE: 97

Leu Tyr Asn Asn Lys Thr Ile Glu Lys Glu Gln Arg Lys Val
1               5                   10

<210> SEQ ID NO 98
<211> LENGTH: 13
<212> TYPE: PRT
<213> ORGANISM: Haemophilus influenzae

<400> SEQUENCE: 98

Asp Ala Lys Phe Arg Ala Asp Pro Tyr Asn Ala Asn Ser
1               5                   10

<210> SEQ ID NO 99
<211> LENGTH: 13
<212> TYPE: PRT
<213> ORGANISM: Haemophilus influenzae

<400> SEQUENCE: 99

Asp Ala Lys Phe Arg Ala Glu Pro Tyr Asn Ala Asn Ser
1               5                   10

<210> SEQ ID NO 100
<211> LENGTH: 11
<212> TYPE: PRT
<213> ORGANISM: Haemophilus influenzae

<400> SEQUENCE: 100

Asp Thr Ser Ser Lys Thr Val Lys Tyr Lys Asp
1               5                   10

<210> SEQ ID NO 101
<211> LENGTH: 14
<212> TYPE: PRT
<213> ORGANISM: Haemophilus influenzae

<400> SEQUENCE: 101

Asp His Tyr Asp Thr Ser Ser Lys Thr Val Lys Tyr Lys Asp
1               5                   10

<210> SEQ ID NO 102
<211> LENGTH: 15
<212> TYPE: PRT
<213> ORGANISM: Haemophilus influenzae

<400> SEQUENCE: 102

Ala Pro Ser Met Gln Glu Arg Phe Val Ser Gly Ala His Phe Gly
1               5                   10                  15

<210> SEQ ID NO 103
<211> LENGTH: 14
<212> TYPE: PRT
<213> ORGANISM: Haemophilus influenzae

<400> SEQUENCE: 103

Asp Lys Asp Ser Gly Glu Ala Leu Ser Asn Ile Ala Ala Ser
1               5                   10

<210> SEQ ID NO 104
<211> LENGTH: 18
<212> TYPE: PRT
<213> ORGANISM: Haemophilus influenzae

<400> SEQUENCE: 104

Lys Gly Lys Asp Lys Asp Ser Gly Glu Ala Leu Ser Asn Ile Ala Ala
1               5                   10                  15

Ser Lys

<210> SEQ ID NO 105
<211> LENGTH: 18
<212> TYPE: PRT
<213> ORGANISM: Haemophilus influenzae

<400> SEQUENCE: 105

Lys Gly Arg Asp Lys Asp Ser Gly Glu Ala Leu Ser Asn Ile Ala Ala
1               5                   10                  15

Ser Lys

<210> SEQ ID NO 106
<211> LENGTH: 13
<212> TYPE: PRT
<213> ORGANISM: Haemophilus influenzae

<400> SEQUENCE: 106

Arg Val Pro Lys Asp His Ser Val Thr Tyr Pro Ser Tyr
1               5                   10

<210> SEQ ID NO 107
<211> LENGTH: 13
<212> TYPE: PRT
<213> ORGANISM: Haemophilus influenzae

<400> SEQUENCE: 107

Arg Val Pro Lys Asp His Ala Val Thr Tyr Pro Ser Tyr
1               5                   10

<210> SEQ ID NO 108
<211> LENGTH: 13
<212> TYPE: PRT
<213> ORGANISM: Haemophilus influenzae

<400> SEQUENCE: 108

Arg Val Pro Lys Asp His Gly Val Thr Tyr Pro Ser Tyr
1               5                   10

<210> SEQ ID NO 109
<211> LENGTH: 21
<212> TYPE: PRT
<213> ORGANISM: Haemophilus influenzae

<400> SEQUENCE: 109

Glu Asn Leu Phe Asp Arg Lys Tyr Gln Pro Ala Phe Ser Leu Met Glu
1               5                   10                  15

Gly Thr Gly Arg Asn
            20

<210> SEQ ID NO 110
<211> LENGTH: 21
<212> TYPE: PRT
<213> ORGANISM: Haemophilus influenzae

<400> SEQUENCE: 110

Glu Asn Leu Phe Asp Arg Lys Tyr Gln Pro Ala Phe Ser Leu Ile Glu
1               5                   10                  15

Gly Thr Gly Arg Asn
            20

<210> SEQ ID NO 111
<211> LENGTH: 27
<212> TYPE: PRT
<213> ORGANISM: Haemophilus influenzae

<400> SEQUENCE: 111

Met Arg Arg Asp Gly Ile Ile Phe Thr Pro Asn Val Ser Asp Lys Gln
1               5                   10                  15

Tyr Tyr Thr Ser Glu Arg Leu Asn Arg Ile Val
            20                  25

<210> SEQ ID NO 112

```
<211> LENGTH: 27
<212> TYPE: PRT
<213> ORGANISM: Haemophilus influenzae

<400> SEQUENCE: 112

Met Arg Arg Asp Gly Ile Ile Phe Thr Pro Asn Ile Ser Asp Lys Gln
1               5                   10                  15

Tyr Tyr Thr Ser Glu Arg Leu Asn Arg Ile Val
            20                  25

<210> SEQ ID NO 113
<211> LENGTH: 35
<212> TYPE: PRT
<213> ORGANISM: Haemophilus influenzae

<400> SEQUENCE: 113

Gly Cys Ser Ser Asn Pro Glu Thr Leu Lys Ala Ser Asn Asp Ser Phe
1               5                   10                  15

Gln Lys Ser Glu Ala Ser Ile Pro His Phe Ser Pro Leu Ala Thr Gly
            20                  25                  30

Gly Val Gln
        35

<210> SEQ ID NO 114
<211> LENGTH: 35
<212> TYPE: PRT
<213> ORGANISM: Haemophilus influenzae

<400> SEQUENCE: 114

Gly Cys Ser Ser Asn Pro Glu Thr Leu Lys Ala Thr Asn Asp Ser Phe
1               5                   10                  15

Gln Lys Ser Glu Ala Ser Ile Pro His Phe Ser Pro Leu Ala Thr Gly
            20                  25                  30

Gly Val Gln
        35

<210> SEQ ID NO 115
<211> LENGTH: 35
<212> TYPE: PRT
<213> ORGANISM: Haemophilus influenzae

<400> SEQUENCE: 115

Gly Cys Ser Ser Asn Pro Glu Thr Leu Lys Ala Thr Asn Asp Ser Phe
1               5                   10                  15

Gln Lys Ser Glu Thr Ser Ile Pro His Phe Ser Pro Leu Ala Thr Gly
            20                  25                  30

Gly Val Gln
        35

<210> SEQ ID NO 116
<211> LENGTH: 35
<212> TYPE: PRT
<213> ORGANISM: Haemophilus influenzae

<400> SEQUENCE: 116

Gly Cys Ser Ser Asn Pro Glu Thr Leu Lys Ala Thr Asn Asp Ser Phe
1               5                   10                  15

Gln Lys Ser Glu Thr Asn Ile Pro His Phe Ser Pro Leu Ala Thr Gly
            20                  25                  30

Gly Val Gln
        35
```

<210> SEQ ID NO 117
<211> LENGTH: 35
<212> TYPE: PRT
<213> ORGANISM: Haemophilus influenzae

<400> SEQUENCE: 117

Gly Cys Ser Ser Asn Pro Glu Thr Leu Lys Ala Thr Asn Asp Ser Phe
1               5                   10                  15

Gln Lys Ser Glu Thr Ser Ile Pro His Phe Ser Pro Leu Ala Thr Gly
            20                  25                  30

Gly Val Gln
        35

<210> SEQ ID NO 118
<211> LENGTH: 24
<212> TYPE: PRT
<213> ORGANISM: Haemophilus influenzae

<400> SEQUENCE: 118

Leu Pro Lys Ala Asp Asp Ala Tyr Ser Leu Pro Asn Ile Glu Val Lys
1               5                   10                  15

Lys Arg Gly Asp Ile Asp Ile Arg
            20

<210> SEQ ID NO 119
<211> LENGTH: 24
<212> TYPE: PRT
<213> ORGANISM: Haemophilus influenzae

<400> SEQUENCE: 119

Leu Ser Lys Ala Asp Asp Ala Tyr Ser Leu Pro Asn Ile Glu Val Lys
1               5                   10                  15

Lys Arg Gly Asp Ile Asp Ile Arg
            20

<210> SEQ ID NO 120
<211> LENGTH: 24
<212> TYPE: PRT
<213> ORGANISM: Haemophilus influenzae

<400> SEQUENCE: 120

Leu Pro Lys Ala Asp Asn Ala Tyr Ser Leu Pro Asn Ile Glu Val Lys
1               5                   10                  15

Lys Arg Gly Asp Ile Asp Ile Arg
            20

<210> SEQ ID NO 121
<211> LENGTH: 24
<212> TYPE: PRT
<213> ORGANISM: Haemophilus influenzae

<400> SEQUENCE: 121

Leu Pro Lys Ala Asp Asp Ser Tyr Ser Leu Pro Asn Ile Glu Val Lys
1               5                   10                  15

Lys Arg Gly Asp Ile Asp Ile Arg
            20

<210> SEQ ID NO 122
<211> LENGTH: 24
<212> TYPE: PRT
<213> ORGANISM: Haemophilus influenzae -continued

```
<400> SEQUENCE: 122

Pro Leu Ala Ile Ile Gln Asn Ser Ile Thr Lys Phe Asp Gly Glu Arg
1               5                   10                  15

Ser Leu Ile Val Tyr Pro Lys Gln
            20

<210> SEQ ID NO 123
<211> LENGTH: 21
<212> TYPE: PRT
<213> ORGANISM: Haemophilus influenzae

<400> SEQUENCE: 123

Gln Asp Lys Arg Arg Tyr Asp Ser Asp Ala Phe Arg Ala Tyr Gln Gln
1               5                   10                  15

Lys Thr Asn Leu Arg
            20

<210> SEQ ID NO 124
<211> LENGTH: 21
<212> TYPE: PRT
<213> ORGANISM: Haemophilus influenzae

<400> SEQUENCE: 124

Gln Asp Lys Arg Arg Tyr Asp Ser Asp Ala Phe Arg Ala Tyr Gln Gln
1               5                   10                  15

Lys Ala Asn Leu Arg
            20

<210> SEQ ID NO 125
<211> LENGTH: 13
<212> TYPE: PRT
<213> ORGANISM: Haemophilus influenzae

<400> SEQUENCE: 125

Val Asp Val Ser Asn Ala Asn Val Gln Thr Thr Val Asn
1               5                   10

<210> SEQ ID NO 126
<211> LENGTH: 9
<212> TYPE: PRT
<213> ORGANISM: Haemophilus influenzae

<400> SEQUENCE: 126

Leu Gln Gln Ser Phe Gly Arg Tyr Trp
1               5

<210> SEQ ID NO 127
<211> LENGTH: 9
<212> TYPE: PRT
<213> ORGANISM: Haemophilus influenzae

<400> SEQUENCE: 127

Leu Gln Gln Pro Phe Gly Arg Tyr Trp
1               5

<210> SEQ ID NO 128
<211> LENGTH: 36
<212> TYPE: PRT
<213> ORGANISM: Haemophilus influenzae

<400> SEQUENCE: 128

Ser Val Gly Asp Gly Ile Ile Ala Lys Asp Phe Thr Arg Asp Lys Ser
```

```
1               5                   10                  15
Gln Asn Asp Phe Thr Ser Phe Val Ser Gly Asp Tyr Val Trp Asn Val
            20                  25                  30

Asp Ser Gly Leu
        35

<210> SEQ ID NO 129
<211> LENGTH: 36
<212> TYPE: PRT
<213> ORGANISM: Haemophilus influenzae

<400> SEQUENCE: 129

Ser Val Gly Asp Gly Ile Ile Ala Lys Asp Phe Ile Arg Asp Lys Ser
1               5                   10                  15

Gln Asn Asp Phe Thr Ser Phe Val Ser Gly Asp Tyr Val Trp Asn Val
            20                  25                  30

Asp Ser Gly Leu
        35

<210> SEQ ID NO 130
<211> LENGTH: 29
<212> TYPE: PRT
<213> ORGANISM: Haemophilus influenzae

<400> SEQUENCE: 130

Trp Gln Leu Ala Tyr Arg Lys Asn Glu Asn Arg Pro Lys Asn Leu Gly
1               5                   10                  15

Asn Val Lys Lys Asp Ile Tyr Ile Ser Asn Asn Leu Ala
            20                  25

<210> SEQ ID NO 131
<211> LENGTH: 29
<212> TYPE: PRT
<213> ORGANISM: Haemophilus influenzae

<400> SEQUENCE: 131

Ser Ile Val Asn Tyr His Arg Val Gln Glu Asn Gln Thr Thr Asn Asp
1               5                   10                  15

Asn Thr Asn Asn Glu Ser Ala Val Lys Asn Leu Glu Glu
            20                  25

<210> SEQ ID NO 132
<211> LENGTH: 29
<212> TYPE: PRT
<213> ORGANISM: Haemophilus influenzae

<400> SEQUENCE: 132

Ser Ile Val Asn Tyr His Arg Val Gln Glu Asn Gln Thr Thr Asn Asp
1               5                   10                  15

Asn Ala Asn Asn Glu Ser Ala Val Lys Asn Leu Glu Glu
            20                  25

<210> SEQ ID NO 133
<211> LENGTH: 29
<212> TYPE: PRT
<213> ORGANISM: Haemophilus influenzae

<400> SEQUENCE: 133

Ser Ile Val Asn Tyr His Arg Val Gln Glu Asn Gln Ile Ile Asn Asp
1               5                   10                  15

Asn Ala Ser Asn Glu Ser Ala Val Lys Asn Leu Glu Glu
```

```
              20                  25

<210> SEQ ID NO 134
<211> LENGTH: 29
<212> TYPE: PRT
<213> ORGANISM: Haemophilus influenzae

<400> SEQUENCE: 134

Ser Ile Val Asn Tyr His Arg Val Gln Glu Asn Gln Thr Ile Asn Asp
1               5                   10                  15

Asn Ala Ser Asn Glu Ser Ala Val Lys Asn Leu Glu Glu
            20                  25

<210> SEQ ID NO 135
<211> LENGTH: 26
<212> TYPE: PRT
<213> ORGANISM: Haemophilus influenzae

<400> SEQUENCE: 135

Glu Leu Asp Ser Gly Tyr Asp Tyr Thr His Leu Asn Arg Gly Leu Asn
1               5                   10                  15

Phe Tyr Tyr Val Gly Arg Tyr His Leu Ala
            20                  25

<210> SEQ ID NO 136
<211> LENGTH: 26
<212> TYPE: PRT
<213> ORGANISM: Haemophilus influenzae

<400> SEQUENCE: 136

Glu Leu Asp Ser Ser Tyr Asp Tyr Thr His Leu Asn Arg Gly Leu Asn
1               5                   10                  15

Phe Tyr Tyr Val Gly Arg Tyr His Leu Ala
            20                  25

<210> SEQ ID NO 137
<211> LENGTH: 26
<212> TYPE: PRT
<213> ORGANISM: Haemophilus influenzae

<400> SEQUENCE: 137

Glu Leu Asp Ser Gly Tyr Asp Tyr Thr His Leu Asn Arg Gly Leu Asn
1               5                   10                  15

Phe Tyr Tyr Val Gly His Tyr His Leu Ala
            20                  25

<210> SEQ ID NO 138
<211> LENGTH: 26
<212> TYPE: PRT
<213> ORGANISM: Haemophilus influenzae

<400> SEQUENCE: 138

Glu Leu Asp Ser Gly Tyr Asp Tyr Thr His Leu Asn Arg Gly Leu Asn
1               5                   10                  15

Phe Tyr Tyr Val Gly Arg Tyr Pro Leu Ala
            20                  25

<210> SEQ ID NO 139
<211> LENGTH: 25
<212> TYPE: PRT
<213> ORGANISM: Haemophilus influenzae

<400> SEQUENCE: 139
```

```
Leu Asn Glu Gln Lys Leu Lys Pro Gln Glu Ala Gln Thr Asn Leu Val
1               5                   10                  15

Glu Arg Ala Lys Gly Leu Ser Glu Asp
            20                  25

<210> SEQ ID NO 140
<211> LENGTH: 16
<212> TYPE: PRT
<213> ORGANISM: Haemophilus influenzae

<400> SEQUENCE: 140

Leu Gln Gln Arg Ala Ser Glu Phe Ala Glu Asn Ser Gln Gln Tyr Ala
1               5                   10                  15

<210> SEQ ID NO 141
<211> LENGTH: 16
<212> TYPE: PRT
<213> ORGANISM: Haemophilus influenzae

<400> SEQUENCE: 141

Leu Gln Gln Arg Ala Asn Gly Phe Ala Glu Asn Ser Gln Gln Tyr Ala
1               5                   10                  15

<210> SEQ ID NO 142
<211> LENGTH: 18
<212> TYPE: PRT
<213> ORGANISM: Haemophilus influenzae

<400> SEQUENCE: 142

Ile Leu Thr Glu Thr Tyr Phe Tyr Leu Ala Lys Gln Lys Leu Asn Val
1               5                   10                  15

Gly Leu

<210> SEQ ID NO 143
<211> LENGTH: 15
<212> TYPE: PRT
<213> ORGANISM: Haemophilus influenzae

<400> SEQUENCE: 143

Val Asp Glu Ala Ala Ala Leu Phe Lys Leu Ala Met Ala Asn Gln
1               5                   10                  15

<210> SEQ ID NO 144
<211> LENGTH: 14
<212> TYPE: PRT
<213> ORGANISM: Haemophilus influenzae

<400> SEQUENCE: 144

Val Glu Tyr Arg Phe Ala Ala Phe Glu Leu Met Lys Leu Lys
1               5                   10

<210> SEQ ID NO 145
<211> LENGTH: 26
<212> TYPE: PRT
<213> ORGANISM: Haemophilus influenzae

<400> SEQUENCE: 145

Thr Gly Ser Ala Met Pro Gly Gly Ser Ala Asn Arg Ile Pro Asn Lys
1               5                   10                  15

Ala Gly Ser Asn Pro Glu Gly Ser Ile Ala
            20                  25
```

```
<210> SEQ ID NO 146
<211> LENGTH: 25
<212> TYPE: PRT
<213> ORGANISM: Haemophilus influenzae

<400> SEQUENCE: 146

Tyr Val Ala Gly Gly Lys Asp Gly Tyr Lys Thr Phe Gly Lys Leu Phe
1               5                   10                  15

Asn Asp Pro Lys Tyr Glu Gly Val Asp
            20                  25

<210> SEQ ID NO 147
<211> LENGTH: 25
<212> TYPE: PRT
<213> ORGANISM: Haemophilus influenzae

<400> SEQUENCE: 147

Tyr Val Ala Gly Gly Lys Asp Gly Tyr Lys Thr Phe Gly Lys Leu Phe
1               5                   10                  15

Asn Asp Pro Lys Tyr Glu Gly Ile Asp
            20                  25

<210> SEQ ID NO 148
<211> LENGTH: 20
<212> TYPE: PRT
<213> ORGANISM: Haemophilus influenzae

<400> SEQUENCE: 148

Leu Pro Asp Ala Glu Ser Phe Ile Lys Phe Met Lys Lys His Pro His
1               5                   10                  15

Phe Glu Ala Tyr
            20

<210> SEQ ID NO 149
<211> LENGTH: 32
<212> TYPE: PRT
<213> ORGANISM: Haemophilus influenzae

<400> SEQUENCE: 149

Ser Gly Tyr Ile Arg Leu Val Lys Asn Val Asn Tyr Tyr Ile Asp Ser
1               5                   10                  15

Glu Ser Ile Trp Val Asp Asn Gln Glu Pro Gln Ile Val His Phe Asp
            20                  25                  30

<210> SEQ ID NO 150
<211> LENGTH: 32
<212> TYPE: PRT
<213> ORGANISM: Haemophilus influenzae

<400> SEQUENCE: 150

Ser Gly Tyr Val Arg Leu Val Lys Asn Val Asn Tyr Tyr Ile Asp Ser
1               5                   10                  15

Glu Ser Ile Trp Val Asp Asn Gln Glu Pro Gln Ile Val His Phe Asp
            20                  25                  30

<210> SEQ ID NO 151
<211> LENGTH: 31
<212> TYPE: PRT
<213> ORGANISM: Haemophilus influenzae

<400> SEQUENCE: 151

Ser Gly Tyr Ile Arg Leu Val Lys Asn Val Asn Tyr Tyr Ile Asp Ser
1               5                   10                  15
```

-continued

Glu Ser Ile Val Asp Asn Gln Glu Pro Gln Ile Val His Phe Asp
            20                  25                  30

<210> SEQ ID NO 152
<211> LENGTH: 32
<212> TYPE: PRT
<213> ORGANISM: Haemophilus influenzae

<400> SEQUENCE: 152

Ser Gly Tyr Ile Arg Leu Val Lys Asn Val Asn Tyr Tyr Ile Asp Ser
1               5                   10                  15

Glu Ser Ile Trp Val Asp Asn Gln Glu Ser Gln Ile Val His Phe Asp
            20                  25                  30

<210> SEQ ID NO 153
<211> LENGTH: 30
<212> TYPE: PRT
<213> ORGANISM: Haemophilus influenzae

<400> SEQUENCE: 153

Gly Leu Tyr Val Tyr Pro Glu Pro Lys Arg Tyr Ala Arg Ser Val Arg
1               5                   10                  15

Gln Tyr Lys Ile Leu Asn Cys Ala Asn Tyr His Leu Thr Gln
            20                  25                  30

<210> SEQ ID NO 154
<211> LENGTH: 42
<212> TYPE: PRT
<213> ORGANISM: Haemophilus influenzae

<400> SEQUENCE: 154

Asp Phe Tyr Asp Glu Phe Trp Gly Gln Gly Leu Arg Ala Ala Pro Lys
1               5                   10                  15

Lys Gln Lys His Thr Leu Ser Leu Thr Pro Asp Thr Thr Leu Tyr Asn
            20                  25                  30

Ala Ala Gln Ile Ile Cys Ala Asn Tyr Gly
            35                  40

<210> SEQ ID NO 155
<211> LENGTH: 41
<212> TYPE: PRT
<213> ORGANISM: Haemophilus influenzae

<400> SEQUENCE: 155

Asp Phe Tyr Asp Glu Phe Trp Gly Gln Gly Leu Arg Ala Ala Pro Lys
1               5                   10                  15

Lys Lys His Thr Leu Ser Leu Ile Pro Asp Thr Thr Leu Tyr Asn Ala
            20                  25                  30

Ala Gln Ile Ile Cys Ala Asn Tyr Gly
            35                  40

<210> SEQ ID NO 156
<211> LENGTH: 18
<212> TYPE: PRT
<213> ORGANISM: Haemophilus influenzae

<400> SEQUENCE: 156

Ala Ser Val Asn Glu Leu Tyr Thr Lys Gly Thr Thr Ser Leu Gln Glu
1               5                   10                  15

Gly Ser

<210> SEQ ID NO 157
<211> LENGTH: 18
<212> TYPE: PRT
<213> ORGANISM: Haemophilus influenzae

<400> SEQUENCE: 157

Tyr Ser Glu Ala Ile Arg Tyr Leu Lys Ala Thr Thr Glu Arg Phe Pro
1               5                   10                  15

Gly Ser

<210> SEQ ID NO 158
<211> LENGTH: 18
<212> TYPE: PRT
<213> ORGANISM: Haemophilus influenzae

<400> SEQUENCE: 158

Tyr Ser Glu Ala Ile Arg Tyr Leu Lys Ala Thr Thr Glu Arg Phe Pro
1               5                   10                  15

Ser Ser

<210> SEQ ID NO 159
<211> LENGTH: 17
<212> TYPE: PRT
<213> ORGANISM: Haemophilus influenzae

<400> SEQUENCE: 159

Gln Asp Tyr Thr Gln Val Leu Leu Met Val Asp Ser Phe Leu His Gln
1               5                   10                  15

Phe

<210> SEQ ID NO 160
<211> LENGTH: 17
<212> TYPE: PRT
<213> ORGANISM: Haemophilus influenzae

<400> SEQUENCE: 160

Gln Asp Tyr Thr Gln Val Leu Leu Thr Val Asp Ser Phe Leu His Gln
1               5                   10                  15

Phe

<210> SEQ ID NO 161
<211> LENGTH: 25
<212> TYPE: PRT
<213> ORGANISM: Haemophilus influenzae

<400> SEQUENCE: 161

Asn Gln Ala Tyr Ala Val Tyr Met Ala Gly Leu Thr Asn Ala Ala Thr
1               5                   10                  15

Gly Asp Asn Phe Ile Gln Asp Phe Phe
            20                  25

<210> SEQ ID NO 162
<211> LENGTH: 25
<212> TYPE: PRT
<213> ORGANISM: Haemophilus influenzae

<400> SEQUENCE: 162

Asn Gln Ala Tyr Ala Val Tyr Met Ala Gly Leu Thr Asn Ala Ala Thr
1               5                   10                  15

Gly Asp Asn Val Ile Gln Asp Phe Phe
            20                  25

<210> SEQ ID NO 163
<211> LENGTH: 17
<212> TYPE: PRT
<213> ORGANISM: Haemophilus influenzae

<400> SEQUENCE: 163

Glu Thr Thr Ser Met Arg Thr Ala Phe Ser Asn Phe Gln Asn Leu Val
1               5                   10                  15

Arg

<210> SEQ ID NO 164
<211> LENGTH: 25
<212> TYPE: PRT
<213> ORGANISM: Haemophilus influenzae

<400> SEQUENCE: 164

Gln Asp Ala Leu Ala Arg Met Ala Tyr Ile Lys Asp Ala Leu Ala Arg
1               5                   10                  15

His Glu Leu Glu Ile Ala Lys Phe Tyr
            20                  25

<210> SEQ ID NO 165
<211> LENGTH: 12
<212> TYPE: PRT
<213> ORGANISM: Haemophilus influenzae

<400> SEQUENCE: 165

Trp Val Ala Val Ala Asn Arg Val Val Gly Met Leu
1               5                   10

<210> SEQ ID NO 166
<211> LENGTH: 18
<212> TYPE: PRT
<213> ORGANISM: Haemophilus influenzae

<400> SEQUENCE: 166

Thr Lys Ala Thr Tyr Glu Gly Leu Phe Leu Met Gln Glu Ala Tyr Glu
1               5                   10                  15

Lys Met

<210> SEQ ID NO 167
<211> LENGTH: 32
<212> TYPE: PRT
<213> ORGANISM: Haemophilus influenzae

<400> SEQUENCE: 167

Ala Asn Asp Thr Gln Lys Ile Ile Asp Ala Asn Lys Asp Lys Thr Phe
1               5                   10                  15

Ala Pro Ile Glu Lys Pro Asn Glu Pro Asp Leu Lys Val Pro Ala Val
            20                  25                  30

<210> SEQ ID NO 168
<211> LENGTH: 32
<212> TYPE: PRT
<213> ORGANISM: Haemophilus influenzae

<400> SEQUENCE: 168

Ala Asn Asp Thr Gln Lys Ile Ile Asp Ala Asn Lys Asp Lys Thr Phe
1               5                   10                  15

Ser Pro Ile Glu Lys Pro Asn Glu Pro Asp Leu Lys Val Pro Ala Val
            20                  25                  30

```
<210> SEQ ID NO 169
<211> LENGTH: 30
<212> TYPE: PRT
<213> ORGANISM: Haemophilus influenzae

<400> SEQUENCE: 169

Ser Asn Ala Trp Val Thr Val Asp Val Arg Glu Phe Gly Thr Gln Val
1               5                   10                  15

Glu Gln Gly Asn Leu Arg Tyr Lys Leu Asn Thr Lys Ile Gln
            20                  25                  30

<210> SEQ ID NO 170
<211> LENGTH: 30
<212> TYPE: PRT
<213> ORGANISM: Haemophilus influenzae

<400> SEQUENCE: 170

Ser Asn Ala Trp Val Thr Val Asp Leu Arg Glu Phe Gly Thr Gln Val
1               5                   10                  15

Glu Gln Gly Asn Leu Arg Tyr Lys Leu Asn Thr Lys Ile Gln
            20                  25                  30

<210> SEQ ID NO 171
<211> LENGTH: 30
<212> TYPE: PRT
<213> ORGANISM: Haemophilus influenzae

<400> SEQUENCE: 171

Ser Asn Ala Trp Val Thr Val Asp Val His Glu Phe Gly Thr Gln Val
1               5                   10                  15

Glu Gln Gly Asn Leu Arg Tyr Lys Leu Asn Thr Lys Ile Gln
            20                  25                  30

<210> SEQ ID NO 172
<211> LENGTH: 30
<212> TYPE: PRT
<213> ORGANISM: Haemophilus influenzae

<400> SEQUENCE: 172

Ser Asn Ala Trp Val Thr Val Asp Val Arg Glu Phe Ser Thr Gln Val
1               5                   10                  15

Glu Gln Gly Asn Leu Arg Tyr Lys Leu Asn Thr Lys Ile Gln
            20                  25                  30

<210> SEQ ID NO 173
<211> LENGTH: 30
<212> TYPE: PRT
<213> ORGANISM: Haemophilus influenzae

<400> SEQUENCE: 173

Ser Asn Ala Trp Val Thr Val Asp Val Arg Glu Phe Ala Thr Gln Val
1               5                   10                  15

Glu Gln Gly Asn Leu Arg Tyr Lys Leu Asn Thr Lys Ile Gln
            20                  25                  30

<210> SEQ ID NO 174
<211> LENGTH: 31
<212> TYPE: PRT
<213> ORGANISM: Haemophilus influenzae

<400> SEQUENCE: 174
```

-continued

Val Tyr Val Gln Gly Ala Lys Gly Ser Tyr Asn Lys Ser Phe Asn Val
1               5                   10                  15

Thr His Ser Gln Glu Gly Val Phe Asn Ala Gly Asn Asp Glu Ile
            20                  25                  30

<210> SEQ ID NO 175
<211> LENGTH: 31
<212> TYPE: PRT
<213> ORGANISM: Haemophilus influenzae

<400> SEQUENCE: 175

Val Tyr Val Gln Gly Ala Lys Gly Ser Tyr Asn Lys Ser Phe Asn Val
1               5                   10                  15

Thr Arg Ser Gln Glu Gly Val Phe Asn Ala Asp Asn Asp Glu Ile
            20                  25                  30

<210> SEQ ID NO 176
<211> LENGTH: 31
<212> TYPE: PRT
<213> ORGANISM: Haemophilus influenzae

<400> SEQUENCE: 176

Val Tyr Val Gln Gly Ala Lys Gly Ser Tyr Asn Lys Ser Phe Asn Val
1               5                   10                  15

Thr His Ser Gln Glu Gly Val Phe Asn Ala Asp Asn Asp Glu Ile
            20                  25                  30

<210> SEQ ID NO 177
<211> LENGTH: 31
<212> TYPE: PRT
<213> ORGANISM: Haemophilus influenzae

<400> SEQUENCE: 177

Val Tyr Val Gln Gly Ala Lys Gly Ser Tyr Asn Lys Ser Phe Asn Val
1               5                   10                  15

Thr His Ser Gln Glu Gly Val Phe Asn Ala Glu Asn Asp Glu Ile
            20                  25                  30

<210> SEQ ID NO 178
<211> LENGTH: 24
<212> TYPE: PRT
<213> ORGANISM: Haemophilus influenzae

<400> SEQUENCE: 178

Thr Phe Asn Asp Ile Val Asn Asn Ile Tyr Gln Asp Gln Glu Val Ala
1               5                   10                  15

Ala Ala Ile Asn Gln Tyr Ser Asn
            20

<210> SEQ ID NO 179
<211> LENGTH: 24
<212> TYPE: PRT
<213> ORGANISM: Haemophilus influenzae

<400> SEQUENCE: 179

Thr Phe Asn Asp Ile Val Asn Asn Ile Tyr Gln Asp Gln Glu Val Ala
1               5                   10                  15

Val Ala Ile Asn Gln Tyr Ser Asn
            20

<210> SEQ ID NO 180
<211> LENGTH: 11

-continued

```
<212> TYPE: PRT
<213> ORGANISM: Haemophilus influenzae

<400> SEQUENCE: 180

Ile Thr Ser Ala Glu Asp Lys Glu Tyr Gly Val
1               5                   10

<210> SEQ ID NO 181
<211> LENGTH: 11
<212> TYPE: PRT
<213> ORGANISM: Haemophilus influenzae

<400> SEQUENCE: 181

Ile Thr Thr Ala Glu Asp Lys Glu Tyr Gly Leu
1               5                   10

<210> SEQ ID NO 182
<211> LENGTH: 11
<212> TYPE: PRT
<213> ORGANISM: Haemophilus influenzae

<400> SEQUENCE: 182

Ile Thr Thr Ala Glu Asp Lys Glu Tyr Gly Val
1               5                   10

<210> SEQ ID NO 183
<211> LENGTH: 35
<212> TYPE: PRT
<213> ORGANISM: Haemophilus influenzae

<400> SEQUENCE: 183

Cys Thr Ser Asn Thr Lys Asn Thr Gln Ile Pro Thr Thr Pro Asn Gly
1               5                   10                  15

Ser Asp Pro Gln Gln Phe Gly Ala Lys Tyr Thr Asn Arg Thr Tyr Gln
            20                  25                  30

Gln Thr Ala
        35

<210> SEQ ID NO 184
<211> LENGTH: 35
<212> TYPE: PRT
<213> ORGANISM: Haemophilus influenzae

<400> SEQUENCE: 184

Cys Thr Ser Asn Thr Lys Asn Thr Gln Ile Pro Thr Thr Ser Asn Gly
1               5                   10                  15

Ser Asp Pro Gln Gln Phe Gly Ala Lys Tyr Thr Asn Arg Thr Tyr Gln
            20                  25                  30

Gln Thr Ala
        35

<210> SEQ ID NO 185
<211> LENGTH: 35
<212> TYPE: PRT
<213> ORGANISM: Haemophilus influenzae

<400> SEQUENCE: 185

Cys Thr Ser Asn Thr Lys Asn Thr Gln Ile Pro Thr Thr Leu Asn Gly
1               5                   10                  15

Ser Asp Pro Gln Gln Phe Gly Ala Lys Tyr Thr Asn Arg Thr Tyr Gln
            20                  25                  30

Gln Thr Ala
```

<210> SEQ ID NO 186
<211> LENGTH: 35
<212> TYPE: PRT
<213> ORGANISM: Haemophilus influenzae

<400> SEQUENCE: 186

Cys Thr Ser Asn Ile Lys Asn Ile Gln Ile Pro Thr Thr Leu Asn Gly
1               5                   10                  15

Ser Asp Pro Gln Gln Phe Gly Ala Lys Tyr Thr Asn Arg Thr Tyr Gln
            20                  25                  30

Gln Ala Ala
        35

<210> SEQ ID NO 187
<211> LENGTH: 26
<212> TYPE: PRT
<213> ORGANISM: Haemophilus influenzae

<400> SEQUENCE: 187

Ser Asn Ile Lys Asn Tyr Ser Ser Lys Leu Ser Thr Asn Phe Tyr Asp
1               5                   10                  15

Asn Tyr Glu Lys Ile Thr Asn Trp Val Leu
            20                  25

<210> SEQ ID NO 188
<211> LENGTH: 26
<212> TYPE: PRT
<213> ORGANISM: Haemophilus influenzae

<400> SEQUENCE: 188

Ser Asn Ile Lys Ile Ile Gln Val Asn Phe Pro Pro Ile Phe Thr Tyr
1               5                   10                  15

Asn Tyr Glu Lys Ile Thr Asn Trp Val Leu
            20                  25

<210> SEQ ID NO 189
<211> LENGTH: 20
<212> TYPE: PRT
<213> ORGANISM: Haemophilus influenzae

<400> SEQUENCE: 189

Ser Asp Ser Met Leu Glu Asn Phe Leu Leu Gly Val Gln Gly Ser Gly
1               5                   10                  15

Tyr Val Asp Phe
            20

<210> SEQ ID NO 190
<211> LENGTH: 14
<212> TYPE: PRT
<213> ORGANISM: Haemophilus influenzae

<400> SEQUENCE: 190

Tyr Thr Ala Ile Gly Arg Leu Leu Val Glu Asp Gly Glu Ile
1               5                   10

<210> SEQ ID NO 191
<211> LENGTH: 12
<212> TYPE: PRT
<213> ORGANISM: Haemophilus influenzae

<400> SEQUENCE: 191

```
Ser Ile Gln Ala Ile Arg Glu Trp Gly Asn Arg Asn
1               5                   10

<210> SEQ ID NO 192
<211> LENGTH: 12
<212> TYPE: PRT
<213> ORGANISM: Haemophilus influenzae

<400> SEQUENCE: 192

Ser Ile Gln Ala Ile Arg Glu Trp Ser Asn Arg Asn
1               5                   10

<210> SEQ ID NO 193
<211> LENGTH: 18
<212> TYPE: PRT
<213> ORGANISM: Haemophilus influenzae

<400> SEQUENCE: 193

Arg Ala Gly His Ile Ala Gly Leu Ser Lys His Tyr Gly Arg Val Trp
1               5                   10                  15

Val Leu

<210> SEQ ID NO 194
<211> LENGTH: 32
<212> TYPE: PRT
<213> ORGANISM: Haemophilus influenzae

<400> SEQUENCE: 194

Leu Ala Ile Asp Gly Gln Lys Ala Ser Lys Ser Leu Gly Lys Ala Lys
1               5                   10                  15

Thr Phe Thr Val Asp Asp Thr Gln Asn His Gln Val Val Val Arg Leu
                20                  25                  30

<210> SEQ ID NO 195
<211> LENGTH: 32
<212> TYPE: PRT
<213> ORGANISM: Haemophilus influenzae

<400> SEQUENCE: 195

Leu Ala Ile Asp Gly Gln Lys Ala Ser Lys Ser Leu Gly Lys Ala Lys
1               5                   10                  15

Thr Phe Thr Ile Asp Asp Thr Gln Asn His Gln Val Val Val Arg Leu
                20                  25                  30

<210> SEQ ID NO 196
<211> LENGTH: 32
<212> TYPE: PRT
<213> ORGANISM: Haemophilus influenzae

<400> SEQUENCE: 196

Leu Ala Ile Asp Gly Gln Lys Ala Ser Lys Ser Leu Gly Lys Ala Lys
1               5                   10                  15

Thr Phe Thr Val Asp Asp Thr Gln Ser His Gln Val Val Val Arg Leu
                20                  25                  30

<210> SEQ ID NO 197
<211> LENGTH: 32
<212> TYPE: PRT
<213> ORGANISM: Haemophilus influenzae

<400> SEQUENCE: 197

Leu Val Ile Asp Gly Gln Lys Ala Ala Lys Ser Leu Leu Lys Asn Thr
```

```
                1               5                  10                  15
Lys Thr Phe Asn Val Ser Asp Thr Lys His Gln Val Val Arg Leu
                20                  25                  30

<210> SEQ ID NO 198
<211> LENGTH: 28
<212> TYPE: PRT
<213> ORGANISM: Haemophilus influenzae

<400> SEQUENCE: 198

Ile Arg Asn Leu Asp Ser Gly Asp Lys Phe Asn Gln Met Pro Asn Ile
1               5                   10                  15

Thr Val Lys Thr Lys Ser Gly Asn Ala Ile Ser Ala
                20                  25

<210> SEQ ID NO 199
<211> LENGTH: 28
<212> TYPE: PRT
<213> ORGANISM: Haemophilus influenzae

<400> SEQUENCE: 199

Ile Arg Asn Leu Asp Ser Gly Asp Lys Phe Asn Glu Met Pro Asn Ile
1               5                   10                  15

Thr Val Lys Thr Lys Ser Gly Asn Ala Ile Ser Ala
                20                  25

<210> SEQ ID NO 200
<211> LENGTH: 25
<212> TYPE: PRT
<213> ORGANISM: Haemophilus influenzae

<400> SEQUENCE: 200

Ala Arg Ile Glu Met Asp Lys Asn Leu Thr Asp Val Gln Arg Arg Gln
1               5                   10                  15

Asp Asn Ile Asp Lys Thr Trp Ala Leu
                20                  25

<210> SEQ ID NO 201
<211> LENGTH: 25
<212> TYPE: PRT
<213> ORGANISM: Haemophilus influenzae

<400> SEQUENCE: 201

Ala Arg Ile Glu Met Asp Lys Asn Leu Thr Asp Val Gln Arg His Gln
1               5                   10                  15

Asp Asn Ile Asp Lys Thr Trp Ala Leu
                20                  25

<210> SEQ ID NO 202
<211> LENGTH: 27
<212> TYPE: PRT
<213> ORGANISM: Haemophilus influenzae

<400> SEQUENCE: 202

Cys Tyr Tyr Gly Leu Ser Pro Glu Asp Glu Ala Glu Ser Ala Ala Asn
1               5                   10                  15

Lys Met Trp Asn Asp Gly Val Arg Asn Pro Leu
                20                  25

<210> SEQ ID NO 203
<211> LENGTH: 28
<212> TYPE: PRT
```

```
<213> ORGANISM: Haemophilus influenzae

<400> SEQUENCE: 203

Asp Ile Pro Phe Phe Lys Asp Thr Asn Ser Pro Gln Tyr His Lys Leu
1               5                   10                  15
Ala Lys Ser Thr Gly Gly Glu Tyr Gln Leu Met Arg
            20                  25

<210> SEQ ID NO 204
<211> LENGTH: 23
<212> TYPE: PRT
<213> ORGANISM: Haemophilus influenzae

<400> SEQUENCE: 204

Leu Ser Ala Asp Thr Asn Cys Asn Val Glu Arg Asp Met Thr Trp Tyr
1               5                   10                  15
Gln Tyr Gln Asp Gly Ala Ile
            20

<210> SEQ ID NO 205
<211> LENGTH: 31
<212> TYPE: PRT
<213> ORGANISM: Haemophilus influenzae

<400> SEQUENCE: 205

Gln Leu Thr Gly Leu Ile Asn Asn Leu Glu Lys Asp Asn Arg Thr Gly
1               5                   10                  15
Ile Phe His Lys Val Arg Thr Asn Arg Ser Ser Ala Leu Met Gly
            20                  25                  30

<210> SEQ ID NO 206
<211> LENGTH: 32
<212> TYPE: PRT
<213> ORGANISM: Haemophilus influenzae

<400> SEQUENCE: 206

Phe Gly Ile Glu Leu Pro Arg Ser Thr Ala Glu Gln Arg His Leu Gly
1               5                   10                  15
Arg Lys Ile Asn Lys Ser Glu Leu Lys Lys Gly Asp Leu Val Phe Phe
            20                  25                  30

<210> SEQ ID NO 207
<211> LENGTH: 32
<212> TYPE: PRT
<213> ORGANISM: Haemophilus influenzae

<400> SEQUENCE: 207

Phe Gly Ile Glu Leu Pro Arg Ser Thr Ala Glu Gln Arg His Leu Gly
1               5                   10                  15
Arg Lys Ile Asn Lys Ser Glu Leu Lys Arg Gly Asp Leu Val Phe Phe
            20                  25                  30

<210> SEQ ID NO 208
<211> LENGTH: 20
<212> TYPE: PRT
<213> ORGANISM: Haemophilus influenzae

<400> SEQUENCE: 208

Gly Gln Gly Val Thr Ile Ser Ser Leu Asp Glu Lys Tyr Trp Ala Arg
1               5                   10                  15
Thr Tyr Thr Gln
            20
```

<210> SEQ ID NO 209
<211> LENGTH: 23
<212> TYPE: PRT
<213> ORGANISM: Haemophilus influenzae

<400> SEQUENCE: 209

Val Pro Ala Ile Phe Ser Ser Gln Thr Leu Leu Gly Lys Asn Ala Thr
1               5                   10                  15

Thr Gln Ala Phe Phe Asp Ile
            20

<210> SEQ ID NO 210
<211> LENGTH: 23
<212> TYPE: PRT
<213> ORGANISM: Haemophilus influenzae

<400> SEQUENCE: 210

Val Pro Thr Ile Phe Ser Ser Gln Thr Leu Leu Gly Lys Asn Ala Thr
1               5                   10                  15

Thr Gln Ala Phe Phe Asp Ile
            20

<210> SEQ ID NO 211
<211> LENGTH: 23
<212> TYPE: PRT
<213> ORGANISM: Haemophilus influenzae

<400> SEQUENCE: 211

Val Pro Ala Ile Phe Ser Ser Gln Thr Leu Leu Glu Lys Asn Ala Thr
1               5                   10                  15

Thr Gln Ala Phe Phe Asp Ile
            20

<210> SEQ ID NO 212
<211> LENGTH: 23
<212> TYPE: PRT
<213> ORGANISM: Haemophilus influenzae

<400> SEQUENCE: 212

Val Pro Ala Ile Phe Ser Ser Gln Thr Leu Leu Gly Lys Asn Ala Ala
1               5                   10                  15

Thr Gln Ala Phe Phe Asp Ile
            20

<210> SEQ ID NO 213
<211> LENGTH: 29
<212> TYPE: PRT
<213> ORGANISM: Haemophilus influenzae

<400> SEQUENCE: 213

Gly Asn Ala Glu Leu Lys Leu Ala Ser Gly Gln Tyr His Asn Glu Gln
1               5                   10                  15

Ser Lys Thr Asp Phe Asp Trp Ser Asn Val Val Leu Asn
            20                  25

<210> SEQ ID NO 214
<211> LENGTH: 29
<212> TYPE: PRT
<213> ORGANISM: Haemophilus influenzae

<400> SEQUENCE: 214

```
Gly Asn Ala Glu Leu Lys Leu Ala Ser Gly Gln Tyr His Asn Glu Gln
1               5                   10                  15

Ser Lys Ala Asp Phe Asp Trp Ser Asn Val Val Leu Asn
            20                  25

<210> SEQ ID NO 215
<211> LENGTH: 29
<212> TYPE: PRT
<213> ORGANISM: Haemophilus influenzae

<400> SEQUENCE: 215

Gly Asn Ala Glu Leu Lys Leu Ala Ser Gly Gln Tyr His Asn Glu Gln
1               5                   10                  15

Ser Lys Ala Glu Leu Asp Trp Ser Asn Val Val Leu Asn
            20                  25

<210> SEQ ID NO 216
<211> LENGTH: 29
<212> TYPE: PRT
<213> ORGANISM: Haemophilus influenzae

<400> SEQUENCE: 216

Gly Asn Ala Glu Leu Lys Leu Ala Ser Gly Gln Tyr His Asn Glu Gln
1               5                   10                  15

Ser Lys Ala Asp Phe Asp Trp Ser Asn Ile Ile Leu Asn
            20                  25

<210> SEQ ID NO 217
<211> LENGTH: 29
<212> TYPE: PRT
<213> ORGANISM: Haemophilus influenzae

<400> SEQUENCE: 217

Gly Asn Ala Glu Leu Lys Leu Ala Ser Gly Gln Tyr His Asn Glu Gln
1               5                   10                  15

Ser Lys Ala Asp Phe Asp Trp Ser Asn Ile Val Leu Asn
            20                  25

<210> SEQ ID NO 218
<211> LENGTH: 30
<212> TYPE: PRT
<213> ORGANISM: Haemophilus influenzae

<400> SEQUENCE: 218

Lys Thr Asn Leu Asp Glu Leu His Ile Asn Gly Asn Asn Leu Gly Lys
1               5                   10                  15

Val Thr Asn Asn Val Glu Phe Asn His Ile Asp Gly Asn Ala
            20                  25                  30

<210> SEQ ID NO 219
<211> LENGTH: 30
<212> TYPE: PRT
<213> ORGANISM: Haemophilus influenzae

<400> SEQUENCE: 219

Lys Thr Asn Met Asp Glu Leu His Ile Asn Gly Lys Asn Leu Gly Lys
1               5                   10                  15

Phe Thr Asn Asn Leu Glu Leu Asn His Ile Asp Gly Asn Ala
            20                  25                  30

<210> SEQ ID NO 220
<211> LENGTH: 30
```

```
<212> TYPE: PRT
<213> ORGANISM: Haemophilus influenzae

<400> SEQUENCE: 220

Lys Thr Asn Leu Asp Glu Leu His Ile Asn Gly Asn Asn Leu Gly Lys
1               5                   10                  15
Val Ser Asn Asn Val Glu Phe Asn His Ile Asp Gly Asn Ala
            20                  25                  30

<210> SEQ ID NO 221
<211> LENGTH: 31
<212> TYPE: PRT
<213> ORGANISM: Haemophilus influenzae

<400> SEQUENCE: 221

Val Gln Lys Leu Gln Gln Ala Gly Met Ile Ile Ala Asn Asn Gln Pro
1               5                   10                  15
Gln Ile Lys Phe Thr Pro Leu Ser Ile Ser Asp Glu Lys Gly Lys
            20                  25                  30

<210> SEQ ID NO 222
<211> LENGTH: 31
<212> TYPE: PRT
<213> ORGANISM: Haemophilus influenzae

<400> SEQUENCE: 222

Val Gln Lys Leu Gln Gln Ala Gly Met Glu Ile Ala Asn Asn Gln Pro
1               5                   10                  15
Gln Ile Lys Phe Thr Pro Leu Ser Ile Ser Asp Glu Lys Gly Lys
            20                  25                  30

<210> SEQ ID NO 223
<211> LENGTH: 31
<212> TYPE: PRT
<213> ORGANISM: Haemophilus influenzae

<400> SEQUENCE: 223

Val Gln Lys Leu Gln Gln Ala Gly Met Glu Ile Ala Asn Asn Gln Ser
1               5                   10                  15
Gln Ile Lys Phe Thr Pro Leu Ser Ile Ser Asp Glu Lys Gly Lys
            20                  25                  30

<210> SEQ ID NO 224
<211> LENGTH: 31
<212> TYPE: PRT
<213> ORGANISM: Haemophilus influenzae

<400> SEQUENCE: 224

Val Gln Lys Leu Gln Gln Ala Gly Met Val Ile Ala Asn Asn Gln Ala
1               5                   10                  15
Gln Ile Lys Phe Thr Pro Leu Ser Ile Ser Asp Glu Lys Gly Lys
            20                  25                  30

<210> SEQ ID NO 225
<211> LENGTH: 31
<212> TYPE: PRT
<213> ORGANISM: Haemophilus influenzae

<400> SEQUENCE: 225

Val Gln Lys Leu Gln Gln Ala Gly Met Thr Ile Ala Asn Asn Gln Pro
1               5                   10                  15
Gln Ile Lys Phe Thr Pro Leu Ser Ile Ser Asp Glu Lys Gly Lys
```

<210> SEQ ID NO 226
<211> LENGTH: 31
<212> TYPE: PRT
<213> ORGANISM: Haemophilus influenzae

<400> SEQUENCE: 226

Val Gln Lys Leu Gln Gln Ala Gly Met Ala Ile Ala Asn Asn Gln Pro
1               5                   10                  15

Gln Ile Lys Phe Thr Pro Leu Ser Ile Ser Asp Glu Lys Gly Lys
            20                  25                  30

<210> SEQ ID NO 227
<211> LENGTH: 31
<212> TYPE: PRT
<213> ORGANISM: Haemophilus influenzae

<400> SEQUENCE: 227

Val Gln Lys Leu Gln Gln Ala Gly Met Leu Ile Ala Asn Asn Gln Pro
1               5                   10                  15

Gln Ile Lys Phe Thr Pro Leu Ser Ile Ser Asp Glu Lys Gly Lys
            20                  25                  30

<210> SEQ ID NO 228
<211> LENGTH: 31
<212> TYPE: PRT
<213> ORGANISM: Haemophilus influenzae

<400> SEQUENCE: 228

Val Gln Lys Leu Gln Gln Ala Gly Met Ile Ile Ala Asn Asn Gln Leu
1               5                   10                  15

Gln Ile Lys Phe Thr Pro Leu Ser Ile Ser Asp Glu Lys Gly Lys
            20                  25                  30

<210> SEQ ID NO 229
<211> LENGTH: 17
<212> TYPE: PRT
<213> ORGANISM: Haemophilus influenzae

<400> SEQUENCE: 229

Leu Glu Asn Asn Asp Leu Lys Leu Asn Gly Lys Pro Ile Pro Glu Glu
1               5                   10                  15

Gln

<210> SEQ ID NO 230
<211> LENGTH: 17
<212> TYPE: PRT
<213> ORGANISM: Haemophilus influenzae

<400> SEQUENCE: 230

Leu Glu Asn Asn Glu Leu Lys Leu Asn Gly Lys Pro Ile Pro Glu Glu
1               5                   10                  15

Gln

<210> SEQ ID NO 231
<211> LENGTH: 33
<212> TYPE: PRT
<213> ORGANISM: Haemophilus influenzae

<400> SEQUENCE: 231

Ala Ser Leu Phe Leu Phe Ala Cys Ser Ser Phe Gln Asn Asp Asp Tyr

```
1               5                   10                  15
Ala Met Asn Tyr Lys Gly Gln Ile Gly Asp Pro Ile Met Ala Ile Ala
                20                  25                  30
Met
```

<210> SEQ ID NO 232
<211> LENGTH: 32
<212> TYPE: PRT
<213> ORGANISM: Haemophilus influenzae

<400> SEQUENCE: 232

```
Asp Arg Phe Asn Leu Arg Leu Pro Arg Ser Thr Val Glu Gln Ala Asn
1               5                   10                  15
Tyr Gly Lys His Val Arg Lys Glu Asp Ile Gln Thr Gly Asp Leu Ile
                20                  25                  30
```

<210> SEQ ID NO 233
<211> LENGTH: 32
<212> TYPE: PRT
<213> ORGANISM: Haemophilus influenzae

<400> SEQUENCE: 233

```
Asp Arg Phe Asn Leu Arg Leu Pro Arg Ser Thr Thr Glu Gln Ala Asn
1               5                   10                  15
Tyr Gly Lys His Val Arg Lys Glu Asp Ile Gln Thr Gly Asp Leu Ile
                20                  25                  30
```

<210> SEQ ID NO 234
<211> LENGTH: 32
<212> TYPE: PRT
<213> ORGANISM: Haemophilus influenzae

<400> SEQUENCE: 234

```
Asp Arg Phe Asn Leu Arg Leu Pro Arg Ser Thr Val Glu Gln Ala Asn
1               5                   10                  15
Tyr Gly Lys His Val Arg Lys Glu His Ile Gln Thr Gly Asp Leu Ile
                20                  25                  30
```

<210> SEQ ID NO 235
<211> LENGTH: 26
<212> TYPE: PRT
<213> ORGANISM: Haemophilus influenzae

<400> SEQUENCE: 235

```
Phe Phe Lys Thr Gly Arg Gly Pro Asn Gly Tyr His Val Gly Ile Tyr
1               5                   10                  15
Val Lys Glu Asp Lys Phe Leu His Ala Ser
                20                  25
```

<210> SEQ ID NO 236
<211> LENGTH: 26
<212> TYPE: PRT
<213> ORGANISM: Haemophilus influenzae

<400> SEQUENCE: 236

```
Phe Phe Lys Thr Gly Leu Gly Pro Asn Gly Tyr His Val Gly Ile Tyr
1               5                   10                  15
Val Lys Glu Asp Lys Phe Leu His Ala Ser
                20                  25
```

<210> SEQ ID NO 237

```
<211> LENGTH: 26
<212> TYPE: PRT
<213> ORGANISM: Haemophilus influenzae

<400> SEQUENCE: 237

Phe Phe Lys Thr Gly Arg Gly Pro Asn Gly Tyr His Val Gly Ile Tyr
1               5                   10                  15

Val Lys Glu Gly Lys Phe Leu His Ala Ser
            20                  25

<210> SEQ ID NO 238
<211> LENGTH: 22
<212> TYPE: PRT
<213> ORGANISM: Haemophilus influenzae

<400> SEQUENCE: 238

Gly Val Val Tyr Ser Ser Met Asn Asn Pro Tyr Trp Ser Lys Ala Phe
1               5                   10                  15

Trp Gln Val Arg Arg Ile
            20

<210> SEQ ID NO 239
<211> LENGTH: 22
<212> TYPE: PRT
<213> ORGANISM: Haemophilus influenzae

<400> SEQUENCE: 239

Gly Val Val Tyr Ser Ser Met Asn Asn Leu Tyr Trp Ser Lys Ala Phe
1               5                   10                  15

Trp Gln Val Arg Arg Ile
            20

<210> SEQ ID NO 240
<211> LENGTH: 15
<212> TYPE: PRT
<213> ORGANISM: Haemophilus influenzae

<400> SEQUENCE: 240

Gln Arg Arg Val Asp Ile Ser Thr Asn Ser Ala Ile Ser His Lys
1               5                   10                  15

<210> SEQ ID NO 241
<211> LENGTH: 15
<212> TYPE: PRT
<213> ORGANISM: Haemophilus influenzae

<400> SEQUENCE: 241

Gln Arg Arg Val Asp Ile Ser Thr Asn Ser Ala Thr Ser His Lys
1               5                   10                  15

<210> SEQ ID NO 242
<211> LENGTH: 15
<212> TYPE: PRT
<213> ORGANISM: Haemophilus influenzae

<400> SEQUENCE: 242

Gln Arg Arg Val Asp Thr Ser Thr Asn Ser Ala Thr Ser His Lys
1               5                   10                  15

<210> SEQ ID NO 243
<211> LENGTH: 11
<212> TYPE: PRT
<213> ORGANISM: Haemophilus influenzae
```

<400> SEQUENCE: 243

Ala Ser Thr Val Gly Thr Ala Leu His Asn Pro
1               5                   10

<210> SEQ ID NO 244
<211> LENGTH: 11
<212> TYPE: PRT
<213> ORGANISM: Haemophilus influenzae

<400> SEQUENCE: 244

Ala Ser Thr Ile Gly Thr Ala Leu His Asn Pro
1               5                   10

<210> SEQ ID NO 245
<211> LENGTH: 32
<212> TYPE: PRT
<213> ORGANISM: Haemophilus influenzae

<400> SEQUENCE: 245

Val Thr Gly Cys Ala Asn Thr Asp Ile Phe Ser Gly Asp Val Tyr Ser
1               5                   10                  15

Ala Ser Gln Ala Lys Glu Ala Arg Ser Ile Thr Tyr Gly Thr Ile Val
            20                  25                  30

<210> SEQ ID NO 246
<211> LENGTH: 32
<212> TYPE: PRT
<213> ORGANISM: Haemophilus influenzae

<400> SEQUENCE: 246

Val Thr Gly Cys Ala Asn Thr Asp Val Phe Ser Gly Asp Val Tyr Ser
1               5                   10                  15

Ala Ser Gln Ala Lys Glu Ala Arg Ser Ile Thr Tyr Gly Thr Ile Val
            20                  25                  30

<210> SEQ ID NO 247
<211> LENGTH: 32
<212> TYPE: PRT
<213> ORGANISM: Haemophilus influenzae

<400> SEQUENCE: 247

Val Ala Gly Cys Thr Asn Thr Asp Ile Phe Ser Gly Asp Val Tyr Ser
1               5                   10                  15

Ala Ser Gln Ala Lys Glu Ala Arg Ser Ile Thr Tyr Gly Thr Ile Val
            20                  25                  30

<210> SEQ ID NO 248
<211> LENGTH: 25
<212> TYPE: PRT
<213> ORGANISM: Haemophilus influenzae

<400> SEQUENCE: 248

Ile Glu Glu Lys Met Ser Gln Val Asn Gly Ala Glu Leu Val Ile Lys
1               5                   10                  15

Lys Asp Asp Gly Gln Glu Ile Val Val
            20                  25

<210> SEQ ID NO 249
<211> LENGTH: 25
<212> TYPE: PRT
<213> ORGANISM: Haemophilus influenzae

<400> SEQUENCE: 249

```
Ile Glu Glu Lys Val Ser Gln Val Asn Gly Ala Glu Leu Val Ile Lys
1               5                   10                  15

Lys Asp Asp Gly Gln Glu Ile Val Val
            20                  25

<210> SEQ ID NO 250
<211> LENGTH: 25
<212> TYPE: PRT
<213> ORGANISM: Haemophilus influenzae

<400> SEQUENCE: 250

Ile Ser Pro Thr Glu Arg Phe Ser Ser Arg Phe Glu Trp Gln Tyr Gln
1               5                   10                  15

Asn Pro Lys Ser Tyr Thr Leu Lys Leu
            20                  25

<210> SEQ ID NO 251
<211> LENGTH: 25
<212> TYPE: PRT
<213> ORGANISM: Haemophilus influenzae

<400> SEQUENCE: 251

Ile Ser Pro Lys Glu Arg Phe Ser Ser Arg Phe Glu Trp Gln Tyr Gln
1               5                   10                  15

Asn Pro Lys Ser Tyr Thr Leu Lys Leu
            20                  25

<210> SEQ ID NO 252
<211> LENGTH: 25
<212> TYPE: PRT
<213> ORGANISM: Haemophilus influenzae

<400> SEQUENCE: 252

Ile Ser Pro Thr Glu Arg Phe Ser Ser His Phe Glu Trp Gln Tyr Gln
1               5                   10                  15

Asn Pro Lys Ser Tyr Thr Leu Lys Leu
            20                  25

<210> SEQ ID NO 253
<211> LENGTH: 29
<212> TYPE: PRT
<213> ORGANISM: Haemophilus influenzae

<400> SEQUENCE: 253

Ile Gln Met His Gln Ser Gly Met Thr Ile Ser Asp Asn Asn Gly Asn
1               5                   10                  15

Gln Gln Tyr Ala Ala Asn Ala Lys Gln Leu Leu Gln Glu
            20                  25

<210> SEQ ID NO 254
<211> LENGTH: 29
<212> TYPE: PRT
<213> ORGANISM: Haemophilus influenzae

<400> SEQUENCE: 254

Ile Gln Met His Gln Ser Gly Met Thr Ile Ser Asp Asn Asn Gly Asn
1               5                   10                  15

Gln Gln Ser Ala Asp Asn Ala Lys Leu Leu Leu Gln Glu
            20                  25

<210> SEQ ID NO 255
```

```
<211> LENGTH: 28
<212> TYPE: PRT
<213> ORGANISM: Haemophilus influenzae

<400> SEQUENCE: 255

Ile Gln Met Asn Gln Ser Gly Met Thr Ile Ser Asp Asn Asn Gly Asn
1               5                   10                  15

Gln Gln Ser Ala Asp Asn Ala Lys Leu Leu Gln Glu
            20                  25

<210> SEQ ID NO 256
<211> LENGTH: 29
<212> TYPE: PRT
<213> ORGANISM: Haemophilus influenzae

<400> SEQUENCE: 256

Ile Gln Met His Gln Ser Gly Met Thr Ile Ser Asp Asn Asn Gly Asn
1               5                   10                  15

Gln Gln Tyr Ala Ala Asn Ser Lys Gln Leu Leu Gln Glu
            20                  25

<210> SEQ ID NO 257
<211> LENGTH: 24
<212> TYPE: PRT
<213> ORGANISM: Haemophilus influenzae

<400> SEQUENCE: 257

Asp Gly Ser Gln Trp Thr Ala Asp Tyr Leu Thr Tyr His Ser Asn Asn
1               5                   10                  15

Ser Met Pro Glu Asn Ile Leu Leu
            20

<210> SEQ ID NO 258
<211> LENGTH: 36
<212> TYPE: PRT
<213> ORGANISM: Haemophilus influenzae

<400> SEQUENCE: 258

Glu Phe Ser Val Gln Asn Ser Pro His Leu Pro Ser Arg Asp Thr Ile
1               5                   10                  15

Tyr Phe Glu Asp Gly Arg Asp Tyr Phe Ser Tyr Lys Glu Pro Ile Glu
            20                  25                  30

Gln Ala Ser Arg
        35

<210> SEQ ID NO 259
<211> LENGTH: 36
<212> TYPE: PRT
<213> ORGANISM: Haemophilus influenzae

<400> SEQUENCE: 259

Glu Phe Ser Val Gln Lys Ser Pro His Leu Pro Ser Arg Asp Thr Ile
1               5                   10                  15

Tyr Phe Glu Asp Gly Arg Asp Tyr Phe Ser Tyr Lys Glu Pro Ile Glu
            20                  25                  30

Gln Ala Ser Arg
        35

<210> SEQ ID NO 260
<211> LENGTH: 36
<212> TYPE: PRT
<213> ORGANISM: Haemophilus influenzae
```

<400> SEQUENCE: 260

Glu Phe Ser Val Gln Asn Ser Pro Tyr Leu Pro Ser Arg Asp Thr Ile
1               5                   10                  15

Tyr Phe Glu Asp Gly Arg Asp Tyr Phe Ser Tyr Lys Glu Pro Ile Glu
            20                  25                  30

Gln Ala Ser Arg
        35

<210> SEQ ID NO 261
<211> LENGTH: 36
<212> TYPE: PRT
<213> ORGANISM: Haemophilus influenzae

<400> SEQUENCE: 261

Glu Phe Ser Val Gln Asn Ser Pro Tyr Leu Pro Ser Arg Asp Thr Ile
1               5                   10                  15

Tyr Phe Glu Asp Gly Arg Asp Tyr Phe Ser Tyr Gln Glu Pro Ile Glu
            20                  25                  30

Gln Ala Ser Arg
        35

<210> SEQ ID NO 262
<211> LENGTH: 36
<212> TYPE: PRT
<213> ORGANISM: Haemophilus influenzae

<400> SEQUENCE: 262

Glu Phe Ser Val Gln Asn Ser Pro Tyr Leu Pro Ser Arg Asp Thr Ile
1               5                   10                  15

Tyr Phe Glu Asp Gly Arg Asp Tyr Phe Ser Tyr Gln Glu Pro Ile Glu
            20                  25                  30

Gln Val Ser Arg
        35

<210> SEQ ID NO 263
<211> LENGTH: 36
<212> TYPE: PRT
<213> ORGANISM: Haemophilus influenzae

<400> SEQUENCE: 263

Glu Phe Ser Val Gln Asn Ser Pro Tyr Leu Pro Ser Arg Asp Thr Ile
1               5                   10                  15

Tyr Phe Glu Asp Gly Arg Asp Tyr Phe Ser Tyr Lys Glu Pro Ile Glu
            20                  25                  30

Gln Val Ser Arg
        35

<210> SEQ ID NO 264
<211> LENGTH: 31
<212> TYPE: PRT
<213> ORGANISM: Haemophilus influenzae

<400> SEQUENCE: 264

Leu Leu Phe Glu Thr Ser Glu Lys Ser Arg Tyr Thr Glu Leu Ser Thr
1               5                   10                  15

Ser Asn Lys Ile Gln Gln Trp Ala Glu Glu Gln Gly Leu Asp Lys
            20                  25                  30

<210> SEQ ID NO 265

```
<211> LENGTH: 31
<212> TYPE: PRT
<213> ORGANISM: Haemophilus influenzae

<400> SEQUENCE: 265

Leu Leu Phe Glu Thr Ser Glu Lys Ser Arg Tyr Thr Glu Leu Ser Thr
1               5                   10                  15

Ser Asn Lys Ile Gln Gln Trp Ala Glu Lys Gln Gly Leu Asp Lys
            20                  25                  30

<210> SEQ ID NO 266
<211> LENGTH: 31
<212> TYPE: PRT
<213> ORGANISM: Haemophilus influenzae

<400> SEQUENCE: 266

Leu Leu Phe Glu Thr Ser Glu Lys Ser Arg Tyr Thr Glu Leu Ser Ala
1               5                   10                  15

Thr Asn Lys Ile Gln Gln Trp Ala Glu Glu Gln Gly Leu Asp Lys
            20                  25                  30

<210> SEQ ID NO 267
<211> LENGTH: 31
<212> TYPE: PRT
<213> ORGANISM: Haemophilus influenzae

<400> SEQUENCE: 267

Leu Leu Phe Glu Thr Ser Glu Lys Ser Arg Tyr Thr Glu Leu Ser Ser
1               5                   10                  15

Thr Asn Lys Ile Gln Gln Trp Ala Glu Glu Gly Leu Asp Lys
            20                  25                  30

<210> SEQ ID NO 268
<211> LENGTH: 21
<212> TYPE: PRT
<213> ORGANISM: Haemophilus influenzae

<400> SEQUENCE: 268

Leu Tyr Asn Asp Asp Tyr Ser Val Ala Val Leu Asp Phe Leu Val Asn
1               5                   10                  15

Lys Ile Glu Gln Glu
            20

<210> SEQ ID NO 269
<211> LENGTH: 12
<212> TYPE: PRT
<213> ORGANISM: Haemophilus influenzae

<400> SEQUENCE: 269

Thr His His Gly Lys Val Asp Gly Thr Lys Ile Gln
1               5                   10

<210> SEQ ID NO 270
<211> LENGTH: 23
<212> TYPE: PRT
<213> ORGANISM: Haemophilus influenzae

<400> SEQUENCE: 270

Asn Gln Phe Lys Tyr Thr Asn Arg Ala Glu Gln Lys Phe Lys Ser Ser
1               5                   10                  15

Ser Asp Ile Lys Leu Gly Tyr
            20
```

<210> SEQ ID NO 271
<211> LENGTH: 23
<212> TYPE: PRT
<213> ORGANISM: Haemophilus influenzae

<400> SEQUENCE: 271

Asn Gln Phe Lys Tyr Thr Asn Arg Ala Glu Gln Asn Phe Lys Ser Ser
1               5                   10                  15

Ser Glu Ile Lys Leu Gly Tyr
            20

<210> SEQ ID NO 272
<211> LENGTH: 23
<212> TYPE: PRT
<213> ORGANISM: Haemophilus influenzae

<400> SEQUENCE: 272

Asn Gln Phe Lys Tyr Thr Asn Arg Ala Glu Gln Lys Phe Lys Ser Ser
1               5                   10                  15

Ser Asp Ile Glu Leu Gly Tyr
            20

<210> SEQ ID NO 273
<211> LENGTH: 23
<212> TYPE: PRT
<213> ORGANISM: Haemophilus influenzae

<400> SEQUENCE: 273

Asn Gln Phe Lys Tyr Thr Asn Arg Thr Glu Gln Lys Phe Lys Ser Ser
1               5                   10                  15

Ser Asp Ile Lys Leu Gly Tyr
            20

<210> SEQ ID NO 274
<211> LENGTH: 9
<212> TYPE: PRT
<213> ORGANISM: Haemophilus influenzae

<400> SEQUENCE: 274

Phe Asp Ser Thr Lys Val Asn Asn Tyr
1               5

<210> SEQ ID NO 275
<211> LENGTH: 20
<212> TYPE: PRT
<213> ORGANISM: Haemophilus influenzae

<400> SEQUENCE: 275

Ser Trp Asp Tyr Gln Lys Ser Thr Ser Asn His Ala Phe Tyr Arg Tyr
1               5                   10                  15

Asp Lys Asn Arg
            20

<210> SEQ ID NO 276
<211> LENGTH: 16
<212> TYPE: PRT
<213> ORGANISM: Haemophilus influenzae

<400> SEQUENCE: 276

Phe Asn Gly Asn Gly Lys Tyr Tyr Trp Asp Asn Lys Lys Tyr Asn Glu
1               5                   10                  15

-continued

```
<210> SEQ ID NO 277
<211> LENGTH: 23
<212> TYPE: PRT
<213> ORGANISM: Haemophilus influenzae

<400> SEQUENCE: 277

Phe Gln Glu Lys Arg Trp Tyr Ala Gly Gly Ser Ser Gly Thr Asn Thr
1               5                   10                  15

Met Lys Gln Tyr Ala Asp Lys
            20

<210> SEQ ID NO 278
<211> LENGTH: 23
<212> TYPE: PRT
<213> ORGANISM: Haemophilus influenzae

<400> SEQUENCE: 278

Phe Lys Glu Lys Arg Trp Tyr Ala Gly Gly Ser Ser Gly Thr Asn Thr
1               5                   10                  15

Met Lys Gln Tyr Ala Asp Lys
            20

<210> SEQ ID NO 279
<211> LENGTH: 13
<212> TYPE: PRT
<213> ORGANISM: Haemophilus influenzae

<400> SEQUENCE: 279

Gly Lys Ser Arg Tyr Lys Ile Arg Lys His Leu Asp Gly
1               5                   10

<210> SEQ ID NO 280
<211> LENGTH: 13
<212> TYPE: PRT
<213> ORGANISM: Haemophilus influenzae

<400> SEQUENCE: 280

Gly Lys Ser Arg Tyr Lys Thr Arg Lys His Leu Asp Gly
1               5                   10

<210> SEQ ID NO 281
<211> LENGTH: 13
<212> TYPE: PRT
<213> ORGANISM: Haemophilus influenzae

<400> SEQUENCE: 281

Gly Glu Ser Arg Tyr Lys Ile Arg Lys His Leu Asp Gly
1               5                   10

<210> SEQ ID NO 282
<211> LENGTH: 14
<212> TYPE: PRT
<213> ORGANISM: Haemophilus influenzae

<400> SEQUENCE: 282

Arg Glu Asn Thr Gln Ala Leu Asp Asn Ala Tyr Gln Gln Lys
1               5                   10

<210> SEQ ID NO 283
<211> LENGTH: 19
<212> TYPE: PRT
<213> ORGANISM: Haemophilus influenzae

<400> SEQUENCE: 283
```

Ala Asn Arg Ala Tyr Arg Glu Lys Asp Leu Ile Gly Ile Gln Gln Lys
1               5                   10                  15

Asn Arg Glu

<210> SEQ ID NO 284
<211> LENGTH: 19
<212> TYPE: PRT
<213> ORGANISM: Haemophilus influenzae

<400> SEQUENCE: 284

Ala Asn Arg Val Tyr Arg Glu Lys Asp Leu Ile Gly Ile Gln Gln Lys
1               5                   10                  15

Asn Arg Glu

<210> SEQ ID NO 285
<211> LENGTH: 19
<212> TYPE: PRT
<213> ORGANISM: Haemophilus influenzae

<400> SEQUENCE: 285

Ala Asn Arg Val Tyr Arg Glu Lys Asp Leu Ile Gly Ile Gln Gln Arg
1               5                   10                  15

Asn Arg Glu

<210> SEQ ID NO 286
<211> LENGTH: 16
<212> TYPE: PRT
<213> ORGANISM: Haemophilus influenzae

<400> SEQUENCE: 286

Leu Asn Asp Asp Asn Leu Asn Asn Ala Pro Lys Ser Gly Thr Lys Ile
1               5                   10                  15

<210> SEQ ID NO 287
<211> LENGTH: 12
<212> TYPE: PRT
<213> ORGANISM: Haemophilus influenzae

<400> SEQUENCE: 287

Ile Pro Ser Leu Gly Gly Gly Met Lys Leu Val Ala
1               5                   10

<210> SEQ ID NO 288
<211> LENGTH: 12
<212> TYPE: PRT
<213> ORGANISM: Haemophilus influenzae

<400> SEQUENCE: 288

Ile Pro Ser Leu Gly Gly Gly Met Lys Leu Val Val
1               5                   10

<210> SEQ ID NO 289
<211> LENGTH: 11
<212> TYPE: PRT
<213> ORGANISM: Haemophilus influenzae

<400> SEQUENCE: 289

Gln Lys Tyr Val Tyr Ser Gly Leu Tyr Tyr Ile
1               5                   10

<210> SEQ ID NO 290
<211> LENGTH: 11
<212> TYPE: PRT

-continued

<213> ORGANISM: Haemophilus influenzae

<400> SEQUENCE: 290

Gln Arg Tyr Val Tyr Ser Gly Leu Tyr Tyr Ile
1               5                   10

<210> SEQ ID NO 291
<211> LENGTH: 11
<212> TYPE: PRT
<213> ORGANISM: Haemophilus influenzae

<400> SEQUENCE: 291

Gln Gln Tyr Val Tyr Ser Gly Leu Tyr Tyr Ile
1               5                   10

<210> SEQ ID NO 292
<211> LENGTH: 11
<212> TYPE: PRT
<213> ORGANISM: Haemophilus influenzae

<400> SEQUENCE: 292

Glu Gly Thr Leu Glu Gly Gly Phe Tyr Gly Pro
1               5                   10

<210> SEQ ID NO 293
<211> LENGTH: 11
<212> TYPE: PRT
<213> ORGANISM: Haemophilus influenzae

<400> SEQUENCE: 293

Asp Gly Thr Leu Glu Gly Gly Phe Tyr Gly Pro
1               5                   10

<210> SEQ ID NO 294
<211> LENGTH: 10
<212> TYPE: PRT
<213> ORGANISM: Haemophilus influenzae

<400> SEQUENCE: 294

Ser Phe Gly Glu Ala Asp Tyr Leu Leu Ile
1               5                   10

<210> SEQ ID NO 295
<211> LENGTH: 12
<212> TYPE: PRT
<213> ORGANISM: Haemophilus influenzae

<400> SEQUENCE: 295

Ala Cys Cys Ser Asn Leu Ser Tyr Val Lys Phe Gly
1               5                   10

<210> SEQ ID NO 296
<211> LENGTH: 12
<212> TYPE: PRT
<213> ORGANISM: Haemophilus influenzae

<400> SEQUENCE: 296

Ala Cys Cys Lys Asn Leu Ser Tyr Val Lys Phe Gly
1               5                   10

<210> SEQ ID NO 297
<211> LENGTH: 12
<212> TYPE: PRT
<213> ORGANISM: Haemophilus influenzae

```
<400> SEQUENCE: 297

Ala Cys Cys Asn Asn Leu Ser Tyr Val Lys Phe Gly
1               5                   10

<210> SEQ ID NO 298
<211> LENGTH: 12
<212> TYPE: PRT
<213> ORGANISM: Haemophilus influenzae

<400> SEQUENCE: 298

Ala Thr Glu Leu Gly Gly Tyr Phe Thr Tyr Asn Ser
1               5                   10

<210> SEQ ID NO 299
<211> LENGTH: 12
<212> TYPE: PRT
<213> ORGANISM: Haemophilus influenzae

<400> SEQUENCE: 299

Ala Ser Glu Leu Gly Gly Tyr Phe Thr Tyr Asn Ser
1               5                   10

<210> SEQ ID NO 300
<211> LENGTH: 10
<212> TYPE: PRT
<213> ORGANISM: Haemophilus influenzae

<400> SEQUENCE: 300

Asn Tyr Ser Ser Glu Gln Tyr Arg Arg Phe
1               5                   10

<210> SEQ ID NO 301
<211> LENGTH: 10
<212> TYPE: PRT
<213> ORGANISM: Haemophilus influenzae

<400> SEQUENCE: 301

Asn Tyr Ser Ser Ser Gln Tyr Arg Arg Phe
1               5                   10

<210> SEQ ID NO 302
<211> LENGTH: 10
<212> TYPE: PRT
<213> ORGANISM: Haemophilus influenzae

<400> SEQUENCE: 302

Asn Tyr Ser Ser Ser Gln Tyr Arg His Phe
1               5                   10

<210> SEQ ID NO 303
<211> LENGTH: 16
<212> TYPE: PRT
<213> ORGANISM: Haemophilus influenzae

<400> SEQUENCE: 303

Gly Lys Ile Asn Val Asn Gly Tyr Asp Phe Ala Tyr Asn Val Glu Asn
1               5                   10                  15

<210> SEQ ID NO 304
<211> LENGTH: 16
<212> TYPE: PRT
<213> ORGANISM: Haemophilus influenzae

<400> SEQUENCE: 304
```

Gly Lys Ile Asn Val Thr Arg Tyr Asp Phe Ala Tyr Asn Val Glu Asn
1               5                   10                  15

<210> SEQ ID NO 305
<211> LENGTH: 16
<212> TYPE: PRT
<213> ORGANISM: Haemophilus influenzae

<400> SEQUENCE: 305

Gly Lys Ile Asn Val Asn Gln Tyr Asp Phe Ala Tyr Asn Val Glu Asn
1               5                   10                  15

<210> SEQ ID NO 306
<211> LENGTH: 16
<212> TYPE: PRT
<213> ORGANISM: Haemophilus influenzae

<400> SEQUENCE: 306

Gly Lys Ile Asn Val Asn Gln Tyr Asp Phe Ala Tyr Asn Met Glu Asn
1               5                   10                  15

<210> SEQ ID NO 307
<211> LENGTH: 16
<212> TYPE: PRT
<213> ORGANISM: Haemophilus influenzae

<400> SEQUENCE: 307

Gly Lys Ile Asn Val Asp Arg Tyr Asp Phe Ala Tyr Asn Val Glu Asn
1               5                   10                  15

<210> SEQ ID NO 308
<211> LENGTH: 46
<212> TYPE: PRT
<213> ORGANISM: Haemophilus influenzae

<400> SEQUENCE: 308

Glu Gln Cys Val Tyr Pro Asn Leu Thr Arg Ile Leu Gln Gln His Phe
1               5                   10                  15

Ser Lys Glu Asp Ser Tyr Ile His Ser Gln Tyr Val Phe Phe Tyr Pro
            20                  25                  30

Leu Glu Lys Ile Ile Gly Glu Gln Tyr Val Lys Ile Ile Gln
        35                  40                  45

<210> SEQ ID NO 309
<211> LENGTH: 34
<212> TYPE: PRT
<213> ORGANISM: Haemophilus influenzae

<400> SEQUENCE: 309

Val Lys Gly Gln Tyr Lys Asn Gly Met Val Glu Val Gln Lys Asn Glu
1               5                   10                  15

Asp Gly Thr Pro Lys Asn Ser Asp Gly Ile Ala Thr Asn Gln Asn Lys
            20                  25                  30

Phe Phe

<210> SEQ ID NO 310
<211> LENGTH: 34
<212> TYPE: PRT
<213> ORGANISM: Haemophilus influenzae

<400> SEQUENCE: 310

Val Lys Gly Gln Tyr Lys Asn Gly Met Val Glu Met Gln Lys Asn Glu
1               5                   10                  15

Asp Gly Thr Pro Lys Asn Ser Asp Gly Ile Ala Thr Asn Gln Asn Lys
            20                  25                  30

Phe Phe

<210> SEQ ID NO 311
<211> LENGTH: 34
<212> TYPE: PRT
<213> ORGANISM: Haemophilus influenzae

<400> SEQUENCE: 311

Val Lys Gly Gln Tyr Lys Asn Gly Met Leu Glu Val Gln Lys Asn Glu
1               5                   10                  15

Asp Gly Thr Pro Lys Asn Ser Asp Gly Ile Ala Thr Asn Gln Asn Lys
            20                  25                  30

Phe Phe

<210> SEQ ID NO 312
<211> LENGTH: 17
<212> TYPE: PRT
<213> ORGANISM: Haemophilus influenzae

<400> SEQUENCE: 312

Asp Glu Lys Ser Met Asn Tyr Ala Ser Tyr Gln Phe Lys Lys Phe Arg
1               5                   10                  15

Thr

<210> SEQ ID NO 313
<211> LENGTH: 14
<212> TYPE: PRT
<213> ORGANISM: Haemophilus influenzae

<400> SEQUENCE: 313

Asn Leu Thr Tyr Ser Thr Lys Pro Ile Leu Asn Ile Thr Ser
1               5                   10

<210> SEQ ID NO 314
<211> LENGTH: 10
<212> TYPE: PRT
<213> ORGANISM: Haemophilus influenzae

<400> SEQUENCE: 314

Gln Lys Ser Ala Val Ile Lys Asn Lys Ser
1               5                   10

<210> SEQ ID NO 315
<211> LENGTH: 11
<212> TYPE: PRT
<213> ORGANISM: Haemophilus influenzae

<400> SEQUENCE: 315

Leu Tyr Trp Tyr Asp His Leu Gly Val Thr Gln
1               5                   10

<210> SEQ ID NO 316
<211> LENGTH: 12
<212> TYPE: PRT
<213> ORGANISM: Haemophilus influenzae

<400> SEQUENCE: 316

Trp Glu Asn Gln Gln Glu Ser Tyr Ser Ala Gln Phe
1               5                   10

<210> SEQ ID NO 317
<211> LENGTH: 26
<212> TYPE: PRT
<213> ORGANISM: Haemophilus influenzae

<400> SEQUENCE: 317

Leu Lys Pro Gln Glu Gln Lys Ser Ile Asp Leu Thr Lys Pro Thr Val
1               5                   10                  15

Glu Ser Lys Asn Tyr Arg Leu Tyr Leu Lys
            20                  25

<210> SEQ ID NO 318
<211> LENGTH: 26
<212> TYPE: PRT
<213> ORGANISM: Haemophilus influenzae

<400> SEQUENCE: 318

Leu Lys Pro Gln Glu Glu Lys Ser Ile Asp Leu Ile Lys Pro Thr Val
1               5                   10                  15

Glu Ser Lys Asn Tyr Arg Leu Tyr Leu Lys
            20                  25

<210> SEQ ID NO 319
<211> LENGTH: 26
<212> TYPE: PRT
<213> ORGANISM: Haemophilus influenzae

<400> SEQUENCE: 319

Leu Lys Pro Gln Glu Glu Lys Ser Ile Asp Leu Ile Lys Pro Thr Ala
1               5                   10                  15

Glu Ser Lys Asn Tyr Arg Leu Tyr Leu Lys
            20                  25

<210> SEQ ID NO 320
<211> LENGTH: 38
<212> TYPE: PRT
<213> ORGANISM: Haemophilus influenzae

<400> SEQUENCE: 320

Gln Gln Ser Val Thr Met Pro Asn Glu Trp Arg Thr Leu Ala Leu Glu
1               5                   10                  15

Ser Asp Asp Ser Tyr Asn Asp Phe Thr Val Ile Met Arg Arg Lys Leu
            20                  25                  30

Gln Glu Asn Gln Val Asn
        35

<210> SEQ ID NO 321
<211> LENGTH: 26
<212> TYPE: PRT
<213> ORGANISM: Haemophilus influenzae

<400> SEQUENCE: 321

Pro Ile Leu Arg Ile Asn Lys Gln Ile Thr Ser Asp Gln Val Ala Ser
1               5                   10                  15

Ile Phe Lys His Gly Arg Glu Ala Glu Lys
            20                  25

<210> SEQ ID NO 322
<211> LENGTH: 25
<212> TYPE: PRT
<213> ORGANISM: Haemophilus influenzae

```
<400> SEQUENCE: 322

Arg Leu Ala Asn Gly Glu Ser Tyr Pro Ile Asn Ala Lys Val Asn Arg
1               5                   10                  15

Thr Phe Phe Asp Asn Ala Arg Ala Ala
            20                  25

<210> SEQ ID NO 323
<211> LENGTH: 25
<212> TYPE: PRT
<213> ORGANISM: Haemophilus influenzae

<400> SEQUENCE: 323

Arg Leu Thr Asn Gly Glu Ser Tyr Pro Ile Asn Ala Lys Val Asn Arg
1               5                   10                  15

Thr Phe Phe Asp Asn Ala Arg Ala Ala
            20                  25

<210> SEQ ID NO 324
<211> LENGTH: 25
<212> TYPE: PRT
<213> ORGANISM: Haemophilus influenzae

<400> SEQUENCE: 324

Arg Leu Thr Asn Gly Glu Ser Tyr Pro Val Asn Ala Lys Val Asn Arg
1               5                   10                  15

Thr Phe Phe Asp Asn Ala Arg Ala Ala
            20                  25

<210> SEQ ID NO 325
<211> LENGTH: 27
<212> TYPE: PRT
<213> ORGANISM: Haemophilus influenzae

<400> SEQUENCE: 325

Glu Val Ile Trp Asn Asp Met Arg Glu Gln Val Ala Arg Gln Leu Ile
1               5                   10                  15

Val Lys Ile Ile Ala Leu Gln Asn Gln Ile Lys
            20                  25

<210> SEQ ID NO 326
<211> LENGTH: 12
<212> TYPE: PRT
<213> ORGANISM: Haemophilus influenzae

<400> SEQUENCE: 326

Glu Asn Tyr Asp Asn Ser Lys Ser Asp Thr Ser Ser
1               5                   10

<210> SEQ ID NO 327
<211> LENGTH: 24
<212> TYPE: PRT
<213> ORGANISM: Haemophilus influenzae

<400> SEQUENCE: 327

Phe Ala Leu Glu Tyr Asn Arg Asn Leu Tyr Ile Gln Ser Met Lys Phe
1               5                   10                  15

Lys Gly Asn Gly Ile Lys Thr Asn
            20

<210> SEQ ID NO 328
<211> LENGTH: 35
<212> TYPE: PRT
```

<213> ORGANISM: Haemophilus influenzae

<400> SEQUENCE: 328

Gly Phe Gly Asn Lys Arg Leu Pro Phe Tyr Gln Thr Tyr Thr Ala Gly
1               5                   10                  15

Gly Ile Gly Ser Leu Arg Gly Phe Ala Tyr Gly Ser Ile Gly Pro Asn
            20                  25                  30

Ala Ile Tyr
        35

<210> SEQ ID NO 329
<211> LENGTH: 12
<212> TYPE: PRT
<213> ORGANISM: Haemophilus influenzae

<400> SEQUENCE: 329

Ile Lys Lys Tyr Glu Asn Asp Asp Val Glu Gln Phe
1               5                   10

<210> SEQ ID NO 330
<211> LENGTH: 10
<212> TYPE: PRT
<213> ORGANISM: Haemophilus influenzae

<400> SEQUENCE: 330

Lys Leu Pro Asp Tyr Gly Lys Ser Ser Arg
1               5                   10

<210> SEQ ID NO 331
<211> LENGTH: 10
<212> TYPE: PRT
<213> ORGANISM: Haemophilus influenzae

<400> SEQUENCE: 331

Ser Leu Pro Asp Tyr Gly Lys Ser Ser Arg
1               5                   10

<210> SEQ ID NO 332
<211> LENGTH: 10
<212> TYPE: PRT
<213> ORGANISM: Haemophilus influenzae

<400> SEQUENCE: 332

Asp Leu Pro Asp Tyr Gly Lys Ser Ser Arg
1               5                   10

<210> SEQ ID NO 333
<211> LENGTH: 10
<212> TYPE: PRT
<213> ORGANISM: Haemophilus influenzae

<400> SEQUENCE: 333

Ser Ser Asp Val Ile Gly Gly Asn Ala Ile
1               5                   10

<210> SEQ ID NO 334
<211> LENGTH: 10
<212> TYPE: PRT
<213> ORGANISM: Haemophilus influenzae

<400> SEQUENCE: 334

Ser Ser Asp Val Val Gly Gly Asn Ala Ile
1               5                   10

```
<210> SEQ ID NO 335
<211> LENGTH: 18
<212> TYPE: PRT
<213> ORGANISM: Haemophilus influenzae

<400> SEQUENCE: 335

Ala Gly Tyr Ile Phe Gln His His Pro Asp Arg Gln Ala Val Ala Asp
1               5                   10                  15

Lys Leu

<210> SEQ ID NO 336
<211> LENGTH: 29
<212> TYPE: PRT
<213> ORGANISM: Haemophilus influenzae

<400> SEQUENCE: 336

Ala Leu Glu Lys Asp Ala Pro Arg Leu Arg Gln Ala Asp Ile Gln Lys
1               5                   10                  15

Arg Gln Gln Glu Ile Asn Lys Leu Gly Ala Ala Glu Asp
            20                  25

<210> SEQ ID NO 337
<211> LENGTH: 29
<212> TYPE: PRT
<213> ORGANISM: Haemophilus influenzae

<400> SEQUENCE: 337

Ala Leu Glu Lys Asp Ala Pro Arg Leu Arg Gln Ala Asp Ile Gln Lys
1               5                   10                  15

Arg Gln Glu Glu Ile Asn Lys Leu Gly Ala Thr Glu Asp
            20                  25

<210> SEQ ID NO 338
<211> LENGTH: 28
<212> TYPE: PRT
<213> ORGANISM: Haemophilus influenzae

<400> SEQUENCE: 338

Leu Met Gln Glu Gln Asp Lys Lys Val Gln Glu Phe Gln Ala Gln Asn
1               5                   10                  15

Glu Lys Arg Gln Ala Glu Glu Arg Gly Lys Leu Leu
            20                  25

<210> SEQ ID NO 339
<211> LENGTH: 17
<212> TYPE: PRT
<213> ORGANISM: Haemophilus influenzae

<400> SEQUENCE: 339

Ala Thr Asn Asn Leu Ala Lys Ala Lys Gly Tyr Thr Tyr Val Leu Asp
1               5                   10                  15

Ala

<210> SEQ ID NO 340
<211> LENGTH: 16
<212> TYPE: PRT
<213> ORGANISM: Haemophilus influenzae

<400> SEQUENCE: 340

Lys Asp Ile Thr Glu Glu Val Leu Lys Ser Ile Pro Ala Ser Glu Lys
1               5                   10                  15
```

```
<210> SEQ ID NO 341
<211> LENGTH: 20
<212> TYPE: PRT
<213> ORGANISM: Haemophilus influenzae

<400> SEQUENCE: 341

Asp Val Pro Gln Gly Asn Tyr Leu Glu Ala Thr Thr Val Ala Gln Val
1               5                   10                  15

Lys Glu Gly Met
            20

<210> SEQ ID NO 342
<211> LENGTH: 27
<212> TYPE: PRT
<213> ORGANISM: Haemophilus influenzae

<400> SEQUENCE: 342

Leu Val Asp Pro Tyr Asn Ser Gln Thr Trp Tyr Tyr Val Phe Leu Gln
1               5                   10                  15

Gln Arg Ala Tyr Glu Thr Pro Val Gln His Thr
            20                  25

<210> SEQ ID NO 343
<211> LENGTH: 27
<212> TYPE: PRT
<213> ORGANISM: Haemophilus influenzae

<400> SEQUENCE: 343

Leu Ile Asp Pro Tyr Asn Asn Tyr Thr Trp Tyr Tyr Val Phe Leu Gln
1               5                   10                  15

Gln Arg Ala Tyr Glu Thr Pro Val Gln His Thr
            20                  25

<210> SEQ ID NO 344
<211> LENGTH: 27
<212> TYPE: PRT
<213> ORGANISM: Haemophilus influenzae

<400> SEQUENCE: 344

Leu Ile Asp Pro Tyr Asn Asn Tyr Thr Trp Tyr Tyr Val Phe Leu Gln
1               5                   10                  15

Gln His Ala Tyr Glu Thr Pro Val Gln His Thr
            20                  25

<210> SEQ ID NO 345
<211> LENGTH: 27
<212> TYPE: PRT
<213> ORGANISM: Haemophilus influenzae

<400> SEQUENCE: 345

Leu Ile Asp Pro Tyr Asn Asn Tyr Thr Trp Tyr Tyr Val Phe Leu Gln
1               5                   10                  15

Gln Arg Ala Tyr Glu Thr Pro Ala Gln His Thr
            20                  25

<210> SEQ ID NO 346
<211> LENGTH: 34
<212> TYPE: PRT
<213> ORGANISM: Haemophilus influenzae

<400> SEQUENCE: 346

Thr Glu Thr His Leu Asp Lys Pro Leu Pro Gln Val Ser Gln Gln Gly
```

```
1               5                  10                 15
Glu Asn Asn Thr Ile Ile Glu Thr Gly Glu Lys Pro Lys Ser Ser Trp
        20                  25                 30

Trp Lys

<210> SEQ ID NO 347
<211> LENGTH: 34
<212> TYPE: PRT
<213> ORGANISM: Haemophilus influenzae

<400> SEQUENCE: 347

Thr Glu Thr His Leu Asp Lys Pro Leu Pro Glu Val Ser Gln Gln Gly
1               5                  10                 15

Glu Asn Asn Thr Ile Ile Glu Thr Gly Glu Lys Pro Lys Ser Ser Trp
        20                  25                 30

Trp Lys

<210> SEQ ID NO 348
<211> LENGTH: 34
<212> TYPE: PRT
<213> ORGANISM: Haemophilus influenzae

<400> SEQUENCE: 348

Thr Glu Thr His Leu Asp Lys Pro Leu Pro Gln Val Ser Gln Gln Asp
1               5                  10                 15

Glu Asn Asn Thr Ile Ile Glu Thr Gly Glu Lys Pro Lys Ser Ser Trp
        20                  25                 30

Trp Lys

<210> SEQ ID NO 349
<211> LENGTH: 17
<212> TYPE: PRT
<213> ORGANISM: Haemophilus influenzae

<400> SEQUENCE: 349

Asp Thr Gln Gly Leu Asp Ile Leu Thr Gly Gln Phe Ser His Asn Ile
1               5                  10                 15

Asp

<210> SEQ ID NO 350
<211> LENGTH: 22
<212> TYPE: PRT
<213> ORGANISM: Haemophilus influenzae

<400> SEQUENCE: 350

Leu Val Ala Ser Arg Lys Asp Tyr Val Lys Tyr Thr Asp Ser Phe Tyr
1               5                  10                 15

Thr Arg Ser His Val Ser
        20

<210> SEQ ID NO 351
<211> LENGTH: 15
<212> TYPE: PRT
<213> ORGANISM: Haemophilus influenzae

<400> SEQUENCE: 351

Val His Thr Leu Leu Met Gly Ala Asp Ala Lys Gly Ile Asp Leu
1               5                  10                 15

<210> SEQ ID NO 352
```

```
<211> LENGTH: 21
<212> TYPE: PRT
<213> ORGANISM: Haemophilus influenzae

<400> SEQUENCE: 352

Ala Asn His Val Glu Val Arg Ala Arg Lys Tyr Leu Pro Leu Ile Arg
1               5                   10                  15

Lys Ala Ala Gln Arg
            20

<210> SEQ ID NO 353
<211> LENGTH: 19
<212> TYPE: PRT
<213> ORGANISM: Haemophilus influenzae

<400> SEQUENCE: 353

Gly Ile Asp Glu Ser Leu Ile Leu Gly Ile Met Gln Thr Glu Ser Ser
1               5                   10                  15

Phe Asn Pro

<210> SEQ ID NO 354
<211> LENGTH: 31
<212> TYPE: PRT
<213> ORGANISM: Haemophilus influenzae

<400> SEQUENCE: 354

Val Phe Thr Met Lys Gly Lys Gly Gly Gln Pro Ser Thr Arg Tyr Leu
1               5                   10                  15

Tyr Asp Pro Ala Asn Asn Ile Asp Ala Gly Val Ser Tyr Leu Trp
            20                  25                  30

<210> SEQ ID NO 355
<211> LENGTH: 31
<212> TYPE: PRT
<213> ORGANISM: Haemophilus influenzae

<400> SEQUENCE: 355

Val Phe Thr Met Lys Gly Lys Gly Gly Gln Pro Ser Thr Arg Tyr Leu
1               5                   10                  15

Tyr Asp Pro Thr Asn Asn Ile Asp Ala Gly Val Ser Tyr Leu Trp
            20                  25                  30

<210> SEQ ID NO 356
<211> LENGTH: 31
<212> TYPE: PRT
<213> ORGANISM: Haemophilus influenzae

<400> SEQUENCE: 356

Val Phe Ala Met Lys Gly Lys Gly Gly Gln Pro Ser Thr Arg Tyr Leu
1               5                   10                  15

Tyr Asp Pro Thr Asn Asn Ile Asp Ala Gly Val Ser Tyr Leu Trp
            20                  25                  30

<210> SEQ ID NO 357
<211> LENGTH: 15
<212> TYPE: PRT
<213> ORGANISM: Haemophilus influenzae

<400> SEQUENCE: 357

Asn Pro Thr Ser Lys Arg Phe Ala Met Ile Ser Ala Tyr Asn Ser
1               5                   10                  15
```

<210> SEQ ID NO 358
<211> LENGTH: 12
<212> TYPE: PRT
<213> ORGANISM: Haemophilus influenzae

<400> SEQUENCE: 358

Ala Gly Ala Val Leu Arg Val Phe Asp Asn Asp Lys
1               5                   10

<210> SEQ ID NO 359
<211> LENGTH: 21
<212> TYPE: PRT
<213> ORGANISM: Haemophilus influenzae

<400> SEQUENCE: 359

Asp Thr Ala Ile Tyr Lys Ile Asn Gln Met Tyr Pro Glu Gln Val Tyr
1               5                   10                  15

Arg Ile Leu Thr Thr
            20

<210> SEQ ID NO 360
<211> LENGTH: 16
<212> TYPE: PRT
<213> ORGANISM: Haemophilus influenzae

<400> SEQUENCE: 360

Ser Ser Gln Ala Arg Asn Tyr Leu Leu Lys Val Asp Lys Ala Gln Lys
1               5                   10                  15

<210> SEQ ID NO 361
<211> LENGTH: 36
<212> TYPE: PRT
<213> ORGANISM: Haemophilus influenzae

<400> SEQUENCE: 361

Asp Leu Asn Gln Ile Gln Lys Gln Ile Lys Gln Gln Glu Ser Lys Ile
1               5                   10                  15

Glu Lys Gln Lys Arg Glu Gln Ala Lys Leu Gln Ala Asn Leu Lys Lys
            20                  25                  30

His Glu Ser Lys
        35

<210> SEQ ID NO 362
<211> LENGTH: 36
<212> TYPE: PRT
<213> ORGANISM: Haemophilus influenzae

<400> SEQUENCE: 362

Asp Leu Asn Gln Ile Gln Lys Gln Ile Lys Gln Gln Glu Ser Lys Ile
1               5                   10                  15

Glu Lys Gln Lys Leu Gln Gln Ala Lys Leu Gln Ala Asn Leu Lys Lys
            20                  25                  30

His Glu Ser Lys
        35

<210> SEQ ID NO 363
<211> LENGTH: 36
<212> TYPE: PRT
<213> ORGANISM: Haemophilus influenzae

<400> SEQUENCE: 363

Asp Leu Asn Gln Ile Gln Lys Gln Ile Lys Gln Gln Glu Ser Lys Ile
1               5                   10                  15

Glu Lys Gln Lys Leu Gln Gln Thr Lys Leu Gln Ala Asn Leu Lys Lys
            20                  25                  30

His Glu Ser Lys
        35

<210> SEQ ID NO 364
<211> LENGTH: 20
<212> TYPE: PRT
<213> ORGANISM: Haemophilus influenzae

<400> SEQUENCE: 364

Lys Ala Glu Arg Met Lys Val Tyr Tyr Gln His Leu Asn Gln Val Arg
1               5                   10                  15

Ile Glu Met Ile
        20

<210> SEQ ID NO 365
<211> LENGTH: 24
<212> TYPE: PRT
<213> ORGANISM: Haemophilus influenzae

<400> SEQUENCE: 365

Ser Gln Gln Lys Asn His Arg Asn Gln Leu Ser Thr Gln Lys Lys Gln
1               5                   10                  15

Gln Gln Ala Leu Gln Lys Ala Gln
        20

<210> SEQ ID NO 366
<211> LENGTH: 12
<212> TYPE: PRT
<213> ORGANISM: Haemophilus influenzae

<400> SEQUENCE: 366

Gln Ser Thr Leu Asn Glu Leu Asn Lys Asn Leu Ala
1               5                   10

<210> SEQ ID NO 367
<211> LENGTH: 15
<212> TYPE: PRT
<213> ORGANISM: Haemophilus influenzae

<400> SEQUENCE: 367

Leu Lys Ala Asn Glu Gln Ala Leu Arg Gln Glu Ile Gln Arg Ala
1               5                   10                  15

<210> SEQ ID NO 368
<211> LENGTH: 25
<212> TYPE: PRT
<213> ORGANISM: Haemophilus influenzae

<400> SEQUENCE: 368

Leu Ala Gln Arg Gln Lys Ala Glu Glu Lys Arg Thr Ser Lys Pro Tyr
1               5                   10                  15

Gln Pro Thr Val Gln Glu Arg Gln Leu
        20                  25

<210> SEQ ID NO 369
<211> LENGTH: 12
<212> TYPE: PRT
<213> ORGANISM: Haemophilus influenzae

<400> SEQUENCE: 369

```
Gln Ala Gly Glu Val Arg Trp Lys Gly Met Val Ile
1               5                   10
```

<210> SEQ ID NO 370
<211> LENGTH: 14
<212> TYPE: PRT
<213> ORGANISM: Haemophilus influenzae

<400> SEQUENCE: 370

```
Ala Gly Tyr Leu Asn Gly Tyr Gly Tyr Met Val Ile Val Lys
1               5                   10
```

<210> SEQ ID NO 371
<211> LENGTH: 10
<212> TYPE: PRT
<213> ORGANISM: Haemophilus influenzae

<400> SEQUENCE: 371

```
Thr Asp Leu Ser Leu Tyr Gly Phe Asn Gln
1               5                   10
```

<210> SEQ ID NO 372
<211> LENGTH: 18
<212> TYPE: PRT
<213> ORGANISM: Haemophilus influenzae

<400> SEQUENCE: 372

```
Gln Val Gly Asn Thr Gly Glu Ile Ser Arg Ser Ala Leu Tyr Phe Gly
1               5                   10                  15

Ile Ser
```

<210> SEQ ID NO 373
<211> LENGTH: 16
<212> TYPE: PRT
<213> ORGANISM: Haemophilus influenzae

<400> SEQUENCE: 373

```
Asp Arg Arg Arg Ser Gly Leu Leu Ile Pro Ser Ala Gly Thr Ser Asn
1               5                   10                  15
```

<210> SEQ ID NO 374
<211> LENGTH: 16
<212> TYPE: PRT
<213> ORGANISM: Haemophilus influenzae

<400> SEQUENCE: 374

```
Asp Arg Arg Arg Ser Gly Leu Leu Ile Pro Ser Ala Gly Thr Ser Ser
1               5                   10                  15
```

<210> SEQ ID NO 375
<211> LENGTH: 16
<212> TYPE: PRT
<213> ORGANISM: Haemophilus influenzae

<400> SEQUENCE: 375

```
Asp Arg Arg Arg Ser Gly Leu Leu Ile Pro Asn Ala Gly Thr Ser Asn
1               5                   10                  15
```

<210> SEQ ID NO 376
<211> LENGTH: 23
<212> TYPE: PRT
<213> ORGANISM: Haemophilus influenzae

<400> SEQUENCE: 376

```
Gly Lys Val Ala Gly Glu Tyr Leu Gly Lys Asp Arg Tyr Ser Glu Tyr
1               5                   10                  15

Ala Ser Asp Asn Arg Lys Arg
            20

<210> SEQ ID NO 377
<211> LENGTH: 23
<212> TYPE: PRT
<213> ORGANISM: Haemophilus influenzae

<400> SEQUENCE: 377

Gly Lys Val Ala Gly Glu Tyr Leu Gly Lys Val Arg Tyr Ser Glu Tyr
1               5                   10                  15

Ala Ser Asp Asn Arg Lys Arg
            20

<210> SEQ ID NO 378
<211> LENGTH: 23
<212> TYPE: PRT
<213> ORGANISM: Haemophilus influenzae

<400> SEQUENCE: 378

Gly Lys Val Ala Gly Glu Tyr Leu Gly Gly Asp Arg Tyr Ser Glu Tyr
1               5                   10                  15

Ala Ser Asn Asn Arg Lys Arg
            20

<210> SEQ ID NO 379
<211> LENGTH: 21
<212> TYPE: PRT
<213> ORGANISM: Haemophilus influenzae

<400> SEQUENCE: 379

Thr Arg Val Ser Asp Lys Arg Tyr Phe Asn Asp Phe Asp Ser Ile Tyr
1               5                   10                  15

Gly Arg Ser Thr Asp
            20

<210> SEQ ID NO 380
<211> LENGTH: 21
<212> TYPE: PRT
<213> ORGANISM: Haemophilus influenzae

<400> SEQUENCE: 380

Thr Arg Val Ser Asp Lys Arg Tyr Phe Asp Asp Phe Asp Ser Ile Tyr
1               5                   10                  15

Gly Arg Ser Thr Asp
            20

<210> SEQ ID NO 381
<211> LENGTH: 21
<212> TYPE: PRT
<213> ORGANISM: Haemophilus influenzae

<400> SEQUENCE: 381

Thr Arg Val Ser Asp Lys Arg Tyr Phe Asn Asp Phe Asp Ser Val Tyr
1               5                   10                  15

Gly Arg Ser Thr Asp
            20

<210> SEQ ID NO 382
<211> LENGTH: 14
```

-continued

```
<212> TYPE: PRT
<213> ORGANISM: Haemophilus influenzae

<400> SEQUENCE: 382

His Gln Phe Gln Ile Phe Asp Asp Ile Val Asn Ile Gly Pro
1               5                   10

<210> SEQ ID NO 383
<211> LENGTH: 14
<212> TYPE: PRT
<213> ORGANISM: Haemophilus influenzae

<400> SEQUENCE: 383

Arg Gln Phe Gln Ile Phe Asp Asp Ile Val Asn Ile Gly Pro
1               5                   10

<210> SEQ ID NO 384
<211> LENGTH: 15
<212> TYPE: PRT
<213> ORGANISM: Haemophilus influenzae

<400> SEQUENCE: 384

Gln Ala Val Arg Phe Asp Asn Asp Ser Glu Leu Met Pro Thr Ala
1               5                   10                  15

<210> SEQ ID NO 385
<211> LENGTH: 15
<212> TYPE: PRT
<213> ORGANISM: Haemophilus influenzae

<400> SEQUENCE: 385

Gln Ala Val Arg Phe Asp Asn Asp Ser Lys Leu Met Pro Thr Ala
1               5                   10                  15

<210> SEQ ID NO 386
<211> LENGTH: 26
<212> TYPE: PRT
<213> ORGANISM: Haemophilus influenzae

<400> SEQUENCE: 386

Thr Arg Tyr Glu Gln Lys Lys Gly Ser Gly Lys Asn Ala Glu Asp Val
1               5                   10                  15

Gln Lys Thr Val Asn Arg Val Ile Pro Gln
            20                  25

<210> SEQ ID NO 387
<211> LENGTH: 26
<212> TYPE: PRT
<213> ORGANISM: Haemophilus influenzae

<400> SEQUENCE: 387

Thr Arg Tyr Glu Gln Lys Lys Gly Ser Gly Lys Asn Ala Lys Asp Val
1               5                   10                  15

Gln Lys Thr Val Asn Arg Val Ile Pro Gln
            20                  25

<210> SEQ ID NO 388
<211> LENGTH: 48
<212> TYPE: PRT
<213> ORGANISM: Haemophilus influenzae

<400> SEQUENCE: 388

Pro Tyr Arg Asn Gln Ser Asn Ile Gly Ser Thr Leu Asn Asn Asp Tyr
1               5                   10                  15
```

-continued

Leu Gly Phe Gly Tyr Asp Ser Ala Leu Val Gln Gln Asp Tyr Tyr Ser
            20                  25                  30

Leu Phe Arg Asp Arg Arg Tyr Ser Gly Leu Asp Arg Ile Ser Ser Ala
        35                  40                  45

<210> SEQ ID NO 389
<211> LENGTH: 48
<212> TYPE: PRT
<213> ORGANISM: Haemophilus influenzae

<400> SEQUENCE: 389

Pro Tyr Arg Asn Gln Ser Asn Ile Gly Ser Thr Leu Asn Asn Asp Tyr
1               5                   10                  15

Leu Gly Phe Gly Tyr Asp Ser Ala Leu Val Gln Gln Asp Tyr Tyr Ser
            20                  25                  30

Leu Phe Arg Asp His Arg Tyr Ser Gly Leu Asp Arg Ile Ser Ser Ala
        35                  40                  45

<210> SEQ ID NO 390
<211> LENGTH: 48
<212> TYPE: PRT
<213> ORGANISM: Haemophilus influenzae

<400> SEQUENCE: 390

Pro Tyr Arg Asn Gln Ser Asn Ile Gly Ser Thr Leu Asn Asn Glu Tyr
1               5                   10                  15

Leu Gly Phe Gly Tyr Asp Ser Ala Leu Val Gln Gln Asp Tyr Tyr Ser
            20                  25                  30

Leu Phe Arg Asp His Arg Tyr Ser Gly Leu Asp Arg Ile Ser Ser Ala
        35                  40                  45

<210> SEQ ID NO 391
<211> LENGTH: 18
<212> TYPE: PRT
<213> ORGANISM: Haemophilus influenzae

<400> SEQUENCE: 391

Ser Asn Ser Arg Ile Asp Glu Asn Pro Ala Asn Lys Thr Pro Thr Ser
1               5                   10                  15

Ser Ala

<210> SEQ ID NO 392
<211> LENGTH: 53
<212> TYPE: PRT
<213> ORGANISM: Haemophilus influenzae

<400> SEQUENCE: 392

Asp Thr His Thr Asn Ser Thr Ser Leu Ala Asn Thr Ser Leu Glu Tyr
1               5                   10                  15

Asn Pro Glu Lys Asn Asn Leu Ile Gln Leu Asn Tyr Arg Tyr Val Asn
            20                  25                  30

Gln Glu Tyr Ile Asp Gln Asn Leu Gly Lys Ser Ala Asn Ala Tyr Gln
        35                  40                  45

Gln Asp Ile Gln Gln
        50

<210> SEQ ID NO 393
<211> LENGTH: 53
<212> TYPE: PRT
<213> ORGANISM: Haemophilus influenzae

```
<400> SEQUENCE: 393

Asp Thr His Thr Asn Ser Thr Ser Leu Ala Asn Thr Ser Leu Glu Tyr
1               5                   10                  15

Asn Pro Glu Lys Asn Asn Leu Ile Gln Leu Asn Tyr Arg Tyr Ser Asn
            20                  25                  30

Gln Glu Tyr Ile Asp Gln Asn Leu Gly Lys Ser Ala Asn Ala Tyr Gln
        35                  40                  45

Gln Asp Ile Gln Gln
        50

<210> SEQ ID NO 394
<211> LENGTH: 18
<212> TYPE: PRT
<213> ORGANISM: Haemophilus influenzae

<400> SEQUENCE: 394

Val Gly Val Lys Arg Asn Val Thr Asn His Gln Asn Gln Thr Arg Asn
1               5                   10                  15

Glu Ile

<210> SEQ ID NO 395
<211> LENGTH: 17
<212> TYPE: PRT
<213> ORGANISM: Haemophilus influenzae

<400> SEQUENCE: 395

Asn Val Gly Gly Ala Trp Gln Pro Glu Ile Gln Lys Asn Ser Leu Pro
1               5                   10                  15

Thr

<210> SEQ ID NO 396
<211> LENGTH: 15
<212> TYPE: PRT
<213> ORGANISM: Haemophilus influenzae

<400> SEQUENCE: 396

Pro Ala Gln Pro Ala Phe Gln Pro Ser Pro Lys Thr Val Val Ser
1               5                   10                  15

<210> SEQ ID NO 397
<211> LENGTH: 36
<212> TYPE: PRT
<213> ORGANISM: Haemophilus influenzae

<400> SEQUENCE: 397

Gln His Ile Asn Ile Pro Arg Asn Pro Asn Thr Asn Ala Pro Asp Tyr
1               5                   10                  15

Ser Lys Ile Ser Lys Gly Ser Tyr Lys Gly Asn Thr Tyr Lys Val Asn
            20                  25                  30

Lys Gly Asp Thr
        35

<210> SEQ ID NO 398
<211> LENGTH: 36
<212> TYPE: PRT
<213> ORGANISM: Haemophilus influenzae

<400> SEQUENCE: 398

Gln His Ile Asn Ile Pro Arg Asn Pro Asn Thr Asn Val Pro Asp Tyr
1               5                   10                  15
```

```
Ser Lys Ile Ser Lys Gly Ser Tyr Lys Gly Asn Thr Tyr Lys Val Asn
            20                  25                  30

Lys Gly Asp Thr
        35

<210> SEQ ID NO 399
<211> LENGTH: 24
<212> TYPE: PRT
<213> ORGANISM: Haemophilus influenzae

<400> SEQUENCE: 399

Asp Val Lys Glu Leu Ala Ala Leu Asn Asn Leu Ser Glu Pro Tyr Asn
1               5                   10                  15

Leu Ser Leu Gly Gln Val Leu Lys
            20

<210> SEQ ID NO 400
<211> LENGTH: 15
<212> TYPE: PRT
<213> ORGANISM: Haemophilus influenzae

<400> SEQUENCE: 400

Lys Thr Val Thr Thr Thr Val Ser Val Lys Gln Pro Ala Val Thr
1               5                   10                  15

<210> SEQ ID NO 401
<211> LENGTH: 25
<212> TYPE: PRT
<213> ORGANISM: Haemophilus influenzae

<400> SEQUENCE: 401

Ala Val Thr Tyr Thr Pro Gly Ala Asn Gly Thr Gln Ile Gly Ser Asp
1               5                   10                  15

Gly Thr Ile Ile Gly Pro Ile Lys Ser
            20                  25

<210> SEQ ID NO 402
<211> LENGTH: 12
<212> TYPE: PRT
<213> ORGANISM: Haemophilus influenzae

<400> SEQUENCE: 402

Thr Ser Ser Thr Gln Val Thr Ser Ser Val Asn Asn
1               5                   10

<210> SEQ ID NO 403
<211> LENGTH: 35
<212> TYPE: PRT
<213> ORGANISM: Haemophilus influenzae

<400> SEQUENCE: 403

Trp Gln Trp Pro Thr Ser Gly Asn Ile Ile Gln Gly Phe Ser Ser Ala
1               5                   10                  15

Asp Gly Gly Asn Lys Gly Ile Asp Ile Ser Gly Ser Arg Gly Gln Ala
            20                  25                  30

Val Lys Ala
        35

<210> SEQ ID NO 404
<211> LENGTH: 35
<212> TYPE: PRT
<213> ORGANISM: Haemophilus influenzae
```

<400> SEQUENCE: 404

Trp Gln Trp Pro Thr Ser Gly Asn Ile Ile Gln Gly Phe Ser Ser Thr
1               5                   10                  15

Asp Gly Gly Asn Lys Gly Ile Asp Ile Ser Gly Ser Arg Gly Gln Ala
            20                  25                  30

Val Lys Ala
        35

<210> SEQ ID NO 405
<211> LENGTH: 18
<212> TYPE: PRT
<213> ORGANISM: Haemophilus influenzae

<400> SEQUENCE: 405

Gly Asn Ala Leu Arg Gly Tyr Gly Asn Leu Ile Ile Ile Lys His Asn
1               5                   10                  15

Asp Asp

<210> SEQ ID NO 406
<211> LENGTH: 13
<212> TYPE: PRT
<213> ORGANISM: Haemophilus influenzae

<400> SEQUENCE: 406

Ala Tyr Ala His Asn Asp Lys Ile Leu Val Ala Asp Gln
1               5                   10

<210> SEQ ID NO 407
<211> LENGTH: 13
<212> TYPE: PRT
<213> ORGANISM: Haemophilus influenzae

<400> SEQUENCE: 407

Ala Tyr Ala His Asn Asp Lys Ile Leu Val Val Asp Gln
1               5                   10

<210> SEQ ID NO 408
<211> LENGTH: 15
<212> TYPE: PRT
<213> ORGANISM: Haemophilus influenzae

<400> SEQUENCE: 408

Lys Ala Gly Gln Asp Ile Ala Lys Met Gly Ser Ser Gly Thr Asn
1               5                   10                  15

<210> SEQ ID NO 409
<211> LENGTH: 14
<212> TYPE: PRT
<213> ORGANISM: Haemophilus influenzae

<400> SEQUENCE: 409

Arg Tyr Lys Gly Lys Ser Val Asp Pro Val Arg Tyr Leu Pro
1               5                   10

<210> SEQ ID NO 410
<211> LENGTH: 11
<212> TYPE: PRT
<213> ORGANISM: Haemophilus influenzae

<400> SEQUENCE: 410

Glu Gly Glu Lys Glu Asn Asp Thr Asn Thr Arg
1               5                   10

<210> SEQ ID NO 411
<211> LENGTH: 21
<212> TYPE: PRT
<213> ORGANISM: Haemophilus influenzae

<400> SEQUENCE: 411

Ser Phe Thr Gln Ala Asp Ile Thr Asp Lys Thr Leu Leu Leu Tyr Pro
1               5                   10                  15

Thr Val Gly Phe Thr
            20

<210> SEQ ID NO 412
<211> LENGTH: 21
<212> TYPE: PRT
<213> ORGANISM: Haemophilus influenzae

<400> SEQUENCE: 412

Ser Phe Ile Gln Ala Asp Ile Thr Asp Lys Thr Leu Leu Leu Tyr Pro
1               5                   10                  15

Thr Val Gly Phe Thr
            20

<210> SEQ ID NO 413
<211> LENGTH: 11
<212> TYPE: PRT
<213> ORGANISM: Haemophilus influenzae

<400> SEQUENCE: 413

Ser Glu Ser Ser Phe Ile Lys Val Gln Ala Ser
1               5                   10

<210> SEQ ID NO 414
<211> LENGTH: 12
<212> TYPE: PRT
<213> ORGANISM: Haemophilus influenzae

<400> SEQUENCE: 414

Leu His Thr Lys Asp Ile Glu Lys Ile Pro Pro Thr
1               5                   10

<210> SEQ ID NO 415
<211> LENGTH: 12
<212> TYPE: PRT
<213> ORGANISM: Haemophilus influenzae

<400> SEQUENCE: 415

Leu His Thr Lys Tyr Ile Glu Lys Ile Pro Pro Thr
1               5                   10

<210> SEQ ID NO 416
<211> LENGTH: 12
<212> TYPE: PRT
<213> ORGANISM: Haemophilus influenzae

<400> SEQUENCE: 416

Leu His Thr Lys Gly Ile Glu Lys Ile Pro Pro Thr
1               5                   10

<210> SEQ ID NO 417
<211> LENGTH: 13
<212> TYPE: PRT
<213> ORGANISM: Haemophilus influenzae

<400> SEQUENCE: 417

Asn Lys Asn Gly Lys Leu Val Gly Gly Ser Arg Leu Leu
1               5                   10

<210> SEQ ID NO 418
<211> LENGTH: 13
<212> TYPE: PRT
<213> ORGANISM: Haemophilus influenzae

<400> SEQUENCE: 418

Asn Arg Asn Gly Lys Leu Val Gly Gly Ser Arg Leu Leu
1               5                   10

<210> SEQ ID NO 419
<211> LENGTH: 10
<212> TYPE: PRT
<213> ORGANISM: Haemophilus influenzae

<400> SEQUENCE: 419

Ile Arg Asp Lys Asp Asn Ser Lys Asn Ile
1               5                   10

<210> SEQ ID NO 420
<211> LENGTH: 18
<212> TYPE: PRT
<213> ORGANISM: Haemophilus influenzae

<400> SEQUENCE: 420

Glu Pro Leu Lys Ser Ala Gly Lys Glu Ile Leu Pro Ala Ser Asp Val
1               5                   10                  15

Asp Leu

<210> SEQ ID NO 421
<211> LENGTH: 18
<212> TYPE: PRT
<213> ORGANISM: Haemophilus influenzae

<400> SEQUENCE: 421

Glu Pro Leu Lys Ser Asp Gly Lys Glu Ile Leu Pro Ala Ser Asp Val
1               5                   10                  15

Asp Leu

<210> SEQ ID NO 422
<211> LENGTH: 18
<212> TYPE: PRT
<213> ORGANISM: Haemophilus influenzae

<400> SEQUENCE: 422

Glu Pro Leu Lys Ser Asp Gly Lys Glu Ile Leu Pro Glu Ser Asp Val
1               5                   10                  15

Asp Leu

<210> SEQ ID NO 423
<211> LENGTH: 18
<212> TYPE: PRT
<213> ORGANISM: Haemophilus influenzae

<400> SEQUENCE: 423

Glu Pro Leu Lys Ser Ala Gly Lys Glu Ile Leu Pro Glu Ser Asp Val
1               5                   10                  15

Asp Leu

<210> SEQ ID NO 424
<211> LENGTH: 18
<212> TYPE: PRT
<213> ORGANISM: Haemophilus influenzae

<400> SEQUENCE: 424

Glu Pro Leu Lys Ser Ser Gly Lys Glu Ile Leu Pro Glu Ser Asp Val
1               5                   10                  15

Asp Leu

<210> SEQ ID NO 425
<211> LENGTH: 14
<212> TYPE: PRT
<213> ORGANISM: Haemophilus influenzae

<400> SEQUENCE: 425

Leu Lys Lys Ser Thr Ala Leu Ser Leu Lys Thr Lys Gly Val
1               5                   10

<210> SEQ ID NO 426
<211> LENGTH: 14
<212> TYPE: PRT
<213> ORGANISM: Haemophilus influenzae

<400> SEQUENCE: 426

Leu Lys Lys Ser Thr Ala Leu Ser Val Lys Thr Lys Gly Val
1               5                   10

<210> SEQ ID NO 427
<211> LENGTH: 33
<212> TYPE: PRT
<213> ORGANISM: Haemophilus influenzae

<400> SEQUENCE: 427

Ala Lys Gly Gln Tyr Thr Phe Val Asn Thr Met Thr Pro Leu Lys Ile
1               5                   10                  15

Asn Asp Val Thr Leu Lys Leu Thr Gly Asp Leu Leu Asn Tyr His Ala
                20                  25                  30

Glu

<210> SEQ ID NO 428
<211> LENGTH: 33
<212> TYPE: PRT
<213> ORGANISM: Haemophilus influenzae

<400> SEQUENCE: 428

Ala Lys Gly Gln Tyr Thr Phe Val Asn Thr Met Ala Pro Leu Lys Ile
1               5                   10                  15

Asn Asp Val Thr Leu Lys Leu Thr Gly Asp Leu Leu Asn Tyr His Ala
                20                  25                  30

Glu

<210> SEQ ID NO 429
<211> LENGTH: 33
<212> TYPE: PRT
<213> ORGANISM: Haemophilus influenzae

<400> SEQUENCE: 429

Ala Lys Gly Gln Tyr Thr Phe Val Asn Thr Met Met Pro Leu Lys Ile
1               5                   10                  15

Asn Asp Val Thr Leu Lys Leu Thr Gly Asp Leu Leu Asn Tyr His Ala

-continued

```
                20                  25                  30
Glu

<210> SEQ ID NO 430
<211> LENGTH: 33
<212> TYPE: PRT
<213> ORGANISM: Haemophilus influenzae

<400> SEQUENCE: 430

Ala Lys Gly Gln Tyr Ala Phe Val Asn Thr Met Thr Pro Leu Lys Ile
1               5                   10                  15

Asn Asp Val Thr Leu Lys Leu Thr Gly Asp Leu Leu Asn Tyr His Ala
                20                  25                  30
Glu

<210> SEQ ID NO 431
<211> LENGTH: 33
<212> TYPE: PRT
<213> ORGANISM: Haemophilus influenzae

<400> SEQUENCE: 431

Ala Lys Gly Gln Tyr Ala Phe Val Asn Thr Met Ala Pro Leu Lys Ile
1               5                   10                  15

Asn Asp Val Thr Leu Lys Leu Thr Gly Asp Leu Leu Asn Tyr His Ala
                20                  25                  30
Glu

<210> SEQ ID NO 432
<211> LENGTH: 33
<212> TYPE: PRT
<213> ORGANISM: Haemophilus influenzae

<400> SEQUENCE: 432

Ala Lys Gly Gln Tyr Ser Phe Val Asn Thr Met Ala Pro Leu Lys Ile
1               5                   10                  15

Asn Asp Met Thr Leu Lys Leu Thr Gly Asp Leu Leu Asn Tyr His Ala
                20                  25                  30
Glu

<210> SEQ ID NO 433
<211> LENGTH: 30
<212> TYPE: PRT
<213> ORGANISM: Haemophilus influenzae

<400> SEQUENCE: 433

Ser Leu Asp Gly Lys Ser Glu Phe Val Gly Thr Ala Asn Trp Lys Glu
1               5                   10                  15

Gly Ala Asn Trp Asp Ile Gln Ala Asp Leu Glu Lys Met Asn
                20                  25                  30

<210> SEQ ID NO 434
<211> LENGTH: 30
<212> TYPE: PRT
<213> ORGANISM: Haemophilus influenzae

<400> SEQUENCE: 434

Ser Leu Asp Gly Lys Ser Glu Phe Val Gly Thr Val Asn Trp Lys Glu
1               5                   10                  15

Gly Ala Asn Trp Asp Ile Gln Ala Asp Leu Glu Lys Met Asn
                20                  25                  30
```

<210> SEQ ID NO 435
<211> LENGTH: 30
<212> TYPE: PRT
<213> ORGANISM: Haemophilus influenzae

<400> SEQUENCE: 435

Ser Leu Asp Gly Lys Ser Glu Phe Val Gly Asn Ala Asn Trp Lys Asn
1               5                   10                  15

Ser Thr Asp Trp Asp Ile Gln Ala Asp Leu Glu Lys Met Asn
            20                  25                  30

<210> SEQ ID NO 436
<211> LENGTH: 30
<212> TYPE: PRT
<213> ORGANISM: Haemophilus influenzae

<400> SEQUENCE: 436

Ser Leu Asp Gly Lys Ser Glu Phe Val Gly Thr Val Asn Trp Lys Glu
1               5                   10                  15

Gly Ala Asn Trp Asp Ile Gln Ala Asp Leu Glu Lys Met Asn
            20                  25                  30

<210> SEQ ID NO 437
<211> LENGTH: 30
<212> TYPE: PRT
<213> ORGANISM: Haemophilus influenzae

<400> SEQUENCE: 437

Ser Leu Asp Gly Lys Ser Glu Phe Ala Gly Asn Ala Asn Trp Lys Asn
1               5                   10                  15

Gly Ala Asn Trp Asp Ile Gln Ala Asp Leu Glu Lys Met Asn
            20                  25                  30

<210> SEQ ID NO 438
<211> LENGTH: 14
<212> TYPE: PRT
<213> ORGANISM: Haemophilus influenzae

<400> SEQUENCE: 438

Phe Phe Val Pro Val Met Pro Ala Thr Leu Ser Gly Lys Leu
1               5                   10

<210> SEQ ID NO 439
<211> LENGTH: 14
<212> TYPE: PRT
<213> ORGANISM: Haemophilus influenzae

<400> SEQUENCE: 439

Phe Phe Val Pro Val Met Pro Ala Ile Leu Ser Gly Lys Leu
1               5                   10

<210> SEQ ID NO 440
<211> LENGTH: 14
<212> TYPE: PRT
<213> ORGANISM: Haemophilus influenzae

<400> SEQUENCE: 440

Ser Arg Gly Phe Ala Gly Ser Gln Gly Trp Gln Val Glu Val
1               5                   10

<210> SEQ ID NO 441
<211> LENGTH: 14

```
<212> TYPE: PRT
<213> ORGANISM: Haemophilus influenzae

<400> SEQUENCE: 441

Ser Arg Gly Phe Ala Asp Ser Gln Gly Trp Gln Val Glu Val
1               5                   10

<210> SEQ ID NO 442
<211> LENGTH: 11
<212> TYPE: PRT
<213> ORGANISM: Haemophilus influenzae

<400> SEQUENCE: 442

Pro Asn Leu Arg Gly Leu Trp Ser Asp Leu Lys
1               5                   10

<210> SEQ ID NO 443
<211> LENGTH: 17
<212> TYPE: PRT
<213> ORGANISM: Haemophilus influenzae

<400> SEQUENCE: 443

Leu Gln Gly Phe Gln Leu Ala Lys Ala Ser Ile Lys Gly His Ile Asn
1               5                   10                  15

Asn

<210> SEQ ID NO 444
<211> LENGTH: 12
<212> TYPE: PRT
<213> ORGANISM: Haemophilus influenzae

<400> SEQUENCE: 444

His Leu Leu Asp Leu Asp Leu Ser Gly Asp Glu Gln
1               5                   10

<210> SEQ ID NO 445
<211> LENGTH: 15
<212> TYPE: PRT
<213> ORGANISM: Haemophilus influenzae

<400> SEQUENCE: 445

Gln Gly Asn Ile Pro Phe Gln Phe Lys Arg Val Asn Leu Asp Leu
1               5                   10                  15

<210> SEQ ID NO 446
<211> LENGTH: 13
<212> TYPE: PRT
<213> ORGANISM: Haemophilus influenzae

<400> SEQUENCE: 446

His Leu Ala Phe Ser Gln Lys Leu Asp Tyr Arg Thr Phe
1               5                   10

<210> SEQ ID NO 447
<211> LENGTH: 19
<212> TYPE: PRT
<213> ORGANISM: Haemophilus influenzae

<400> SEQUENCE: 447

Ile Pro Lys Leu Thr Leu Asn Ala Asp Ile Gln Asn Asn Asn Leu Val
1               5                   10                  15

Leu Lys Thr
```

<210> SEQ ID NO 448
<211> LENGTH: 13
<212> TYPE: PRT
<213> ORGANISM: Haemophilus influenzae

<400> SEQUENCE: 448

Ile Asn Val His Asn Gln Gly Arg Ile Val Gly Asp Ile
1               5                   10

<210> SEQ ID NO 449
<211> LENGTH: 13
<212> TYPE: PRT
<213> ORGANISM: Haemophilus influenzae

<400> SEQUENCE: 449

Ile Asn Leu His Asn Gln Gly Arg Ile Val Gly Asp Ile
1               5                   10

<210> SEQ ID NO 450
<211> LENGTH: 14
<212> TYPE: PRT
<213> ORGANISM: Haemophilus influenzae

<400> SEQUENCE: 450

Ile Ala Asn Gln Leu Leu Thr Gln Gly Glu Ser Val Asn Gly
1               5                   10

<210> SEQ ID NO 451
<211> LENGTH: 14
<212> TYPE: PRT
<213> ORGANISM: Haemophilus influenzae

<400> SEQUENCE: 451

Ile Ala Asn Gln Leu Leu Thr Ser Gly Glu Ser Val Asn Gly
1               5                   10

<210> SEQ ID NO 452
<211> LENGTH: 10
<212> TYPE: PRT
<213> ORGANISM: Haemophilus influenzae

<400> SEQUENCE: 452

Gly Asn Leu Glu Lys Pro Leu Leu Asn Gly
1               5                   10

<210> SEQ ID NO 453
<211> LENGTH: 12
<212> TYPE: PRT
<213> ORGANISM: Haemophilus influenzae

<400> SEQUENCE: 453

Ile Arg Thr Lys Leu Lys Ser Met Pro Val Asn Ile
1               5                   10

<210> SEQ ID NO 454
<211> LENGTH: 12
<212> TYPE: PRT
<213> ORGANISM: Haemophilus influenzae

<400> SEQUENCE: 454

Asn Asn Phe Asn Val Asp Ile Pro Ser Met Ala Lys
1               5                   10

<210> SEQ ID NO 455
<211> LENGTH: 30

```
<212> TYPE: PRT
<213> ORGANISM: Haemophilus influenzae

<400> SEQUENCE: 455

Arg Ile Lys Ile Asp Ser Leu Pro Asp Thr Ala Glu Pro Val Ser Glu
1               5                   10                  15

Asp Glu Val Ile Leu Asn Gly Pro His Lys Ser Lys Glu Glu
            20                  25                  30

<210> SEQ ID NO 456
<211> LENGTH: 30
<212> TYPE: PRT
<213> ORGANISM: Haemophilus influenzae

<400> SEQUENCE: 456

Arg Ile Lys Ile Asp Ser Leu Pro Asp Thr Ala Glu Pro Val Ser Glu
1               5                   10                  15

Asp Glu Ile Ile Leu Asn Gly Pro His Lys Ser Lys Glu Glu
            20                  25                  30

<210> SEQ ID NO 457
<211> LENGTH: 11
<212> TYPE: PRT
<213> ORGANISM: Haemophilus influenzae

<400> SEQUENCE: 457

Thr Lys Gly Arg Tyr Ala Ser Phe Gly Gln Asp
1               5                   10

<210> SEQ ID NO 458
<211> LENGTH: 44
<212> TYPE: PRT
<213> ORGANISM: Haemophilus influenzae

<400> SEQUENCE: 458

Lys Ile Thr Ala Gly Val Arg Val Ile Gly Ile Ala Asp Ser Pro Glu
1               5                   10                  15

Val Thr Ile Phe Ser Glu Pro Ser Lys Ser Gln Asp Gln Ala Leu Ser
            20                  25                  30

Tyr Leu Leu Thr Gly Arg Ser Leu Glu Ser Ser Gly
        35                  40

<210> SEQ ID NO 459
<211> LENGTH: 44
<212> TYPE: PRT
<213> ORGANISM: Haemophilus influenzae

<400> SEQUENCE: 459

Lys Ile Thr Ala Gly Val Arg Val Ile Gly Ile Ala Asp Ser Pro Glu
1               5                   10                  15

Val Thr Ile Phe Ser Glu Pro Ser Lys Pro Gln Asp Gln Ala Leu Ser
            20                  25                  30

Tyr Leu Leu Thr Gly Arg Ser Leu Glu Ser Ser Gly
        35                  40

<210> SEQ ID NO 460
<211> LENGTH: 41
<212> TYPE: PRT
<213> ORGANISM: Haemophilus influenzae

<400> SEQUENCE: 460

Gly Ile Ser Lys Ser Gly Lys Leu Val Gly Ser Ile Gly Glu Val Phe
```

```
1               5                   10                  15
Gly Ile Gln Asp Leu Asn Leu Gly Thr Ser Gly Val Gly Asp Lys Ser
            20                  25                  30

Lys Val Thr Val Ser Gly Asn Ile Thr
            35                  40

<210> SEQ ID NO 461
<211> LENGTH: 11
<212> TYPE: PRT
<213> ORGANISM: Haemophilus influenzae

<400> SEQUENCE: 461

Phe Gln Ser Val Ser Ser Thr Asn Gln Val Phe
1               5                   10

<210> SEQ ID NO 462
<211> LENGTH: 20
<212> TYPE: PRT
<213> ORGANISM: Haemophilus influenzae

<400> SEQUENCE: 462

Asp Asn Ser Pro Tyr Ala Gly Trp Gln Val Gln Asn Asn Lys Pro Phe
1               5                   10                  15

Asp Gly Lys Asp
            20

<210> SEQ ID NO 463
<211> LENGTH: 27
<212> TYPE: PRT
<213> ORGANISM: Haemophilus influenzae

<400> SEQUENCE: 463

Thr Met Leu Asp Asn Ser Pro Tyr Ala Gly Trp Gln Val Lys Asn Asn
1               5                   10                  15

Lys Pro Phe Asp Gly Lys Asp Trp Thr Arg Trp
            20                  25

<210> SEQ ID NO 464
<211> LENGTH: 20
<212> TYPE: PRT
<213> ORGANISM: Haemophilus influenzae

<400> SEQUENCE: 464

Gly Asp Asn Leu Asp Asp Phe Gly Asn Thr Val Tyr Gly Lys Leu Asn
1               5                   10                  15

Ala Asp Arg Arg
            20

<210> SEQ ID NO 465
<211> LENGTH: 20
<212> TYPE: PRT
<213> ORGANISM: Haemophilus influenzae

<400> SEQUENCE: 465

Gly Asp Asn Leu Asp Asp Phe Gly Asn Ser Val Tyr Gly Lys Leu Asn
1               5                   10                  15

Ala Asp Arg Arg
            20

<210> SEQ ID NO 466
<211> LENGTH: 22
<212> TYPE: PRT
```

<213> ORGANISM: Haemophilus influenzae

<400> SEQUENCE: 466

Val Gly Asp Asn Leu Asp Asp Phe Gly Asn Thr Val Tyr Gly Lys Leu
1               5                   10                  15

Asn Ala Asp Arg Arg Ala
            20

<210> SEQ ID NO 467
<211> LENGTH: 22
<212> TYPE: PRT
<213> ORGANISM: Haemophilus influenzae

<400> SEQUENCE: 467

Val Gly Asp Asn Leu Asp Asp Phe Gly Asn Ser Val Tyr Gly Lys Leu
1               5                   10                  15

Asn Ala Asp Arg Arg Ala
            20

<210> SEQ ID NO 468
<211> LENGTH: 19
<212> TYPE: PRT
<213> ORGANISM: Haemophilus influenzae

<400> SEQUENCE: 468

Gly Glu Tyr Arg Ala Leu Ala Tyr Gln Ala Tyr Asn Ala Ala Lys Val
1               5                   10                  15

Ala Phe Asp

<210> SEQ ID NO 469
<211> LENGTH: 19
<212> TYPE: PRT
<213> ORGANISM: Haemophilus influenzae

<400> SEQUENCE: 469

Gly Glu Tyr Lys Ala Leu Ala Tyr Gln Ala Tyr Asn Ala Ala Lys Val
1               5                   10                  15

Ala Phe Asp

<210> SEQ ID NO 470
<211> LENGTH: 16
<212> TYPE: PRT
<213> ORGANISM: Haemophilus influenzae

<400> SEQUENCE: 470

Val Glu Phe Asn Asn Tyr Val Asn Ser His Lys Gly Lys Val Phe Tyr
1               5                   10                  15

<210> SEQ ID NO 471
<211> LENGTH: 16
<212> TYPE: PRT
<213> ORGANISM: Haemophilus influenzae

<400> SEQUENCE: 471

Val Glu Phe Asn Asn Tyr Val Asn Ser His Asn Gly Lys Val Phe Tyr
1               5                   10                  15

<210> SEQ ID NO 472
<211> LENGTH: 13
<212> TYPE: PRT
<213> ORGANISM: Haemophilus influenzae

<400> SEQUENCE: 472

```
Glu Lys Ala Gly Thr Ile Asp Asp Met Lys Arg Leu Gly
1               5                   10
```

<210> SEQ ID NO 473
<211> LENGTH: 17
<212> TYPE: PRT
<213> ORGANISM: Haemophilus influenzae

<400> SEQUENCE: 473

```
Ser Ala Lys Ala Ala Arg Phe Ala Glu Ile Glu Lys Gln Gly Tyr Glu
1               5                   10                  15

Ile
```

<210> SEQ ID NO 474
<211> LENGTH: 17
<212> TYPE: PRT
<213> ORGANISM: Haemophilus influenzae

<400> SEQUENCE: 474

```
Ala Asn Met Gln Leu Gln Gln Gln Ala Val Leu Gly Leu Asn Trp Met
1               5                   10                  15

Gln
```

<210> SEQ ID NO 475
<211> LENGTH: 22
<212> TYPE: PRT
<213> ORGANISM: Haemophilus influenzae

<400> SEQUENCE: 475

```
Met Leu Pro Asn Ala Asn Tyr Gly Gly Trp Glu Gly Gly Leu Ala Glu
1               5                   10                  15

Gly Tyr Phe Lys Lys Asp
                20
```

<210> SEQ ID NO 476
<211> LENGTH: 12
<212> TYPE: PRT
<213> ORGANISM: Haemophilus influenzae

<400> SEQUENCE: 476

```
Thr Gln Gly Gln Ile Lys Ala Arg Leu Asp Ala Val
1               5                   10
```

<210> SEQ ID NO 477
<211> LENGTH: 12
<212> TYPE: PRT
<213> ORGANISM: Haemophilus influenzae

<400> SEQUENCE: 477

```
Thr Gln Gly Gln Ile Lys Ala Arg Leu Asp Ala Ile
1               5                   10
```

<210> SEQ ID NO 478
<211> LENGTH: 26
<212> TYPE: PRT
<213> ORGANISM: Haemophilus influenzae

<400> SEQUENCE: 478

```
Asn Ala Gly Asp Tyr Lys Arg Pro Asp Asn Ser Lys Ile Leu Phe Ser
1               5                   10                  15

Lys Asn Asn Gln Lys Thr Gly Leu Ile Lys
                20                  25
```

-continued

<210> SEQ ID NO 479
<211> LENGTH: 26
<212> TYPE: PRT
<213> ORGANISM: Haemophilus influenzae

<400> SEQUENCE: 479

Asn Ala Gly Asp Tyr Lys Arg Pro Asp Asn Ser Arg Ile Leu Phe Ser
1               5                   10                  15

Lys Asn Asn Gln Lys Thr Gly Leu Ile Lys
            20                  25

<210> SEQ ID NO 480
<211> LENGTH: 26
<212> TYPE: PRT
<213> ORGANISM: Haemophilus influenzae

<400> SEQUENCE: 480

Asn Ala Asp Asp Tyr Lys Arg Pro Asp Asn Ser Arg Ile Leu Phe Ser
1               5                   10                  15

Lys Asn Asn Gln Lys Thr Gly Leu Ile Lys
            20                  25

<210> SEQ ID NO 481
<211> LENGTH: 17
<212> TYPE: PRT
<213> ORGANISM: Haemophilus influenzae

<400> SEQUENCE: 481

Gly Lys Asn Glu Ile Phe Lys Thr Arg Gly Val Asn Cys Val Gly Asn
1               5                   10                  15

Ala

<210> SEQ ID NO 482
<211> LENGTH: 17
<212> TYPE: PRT
<213> ORGANISM: Haemophilus influenzae

<400> SEQUENCE: 482

Gly Lys Asn Glu Ile Phe Lys Thr Arg Gly Val Tyr Cys Val Gly Asn
1               5                   10                  15

Ala

<210> SEQ ID NO 483
<211> LENGTH: 17
<212> TYPE: PRT
<213> ORGANISM: Haemophilus influenzae

<400> SEQUENCE: 483

Gly Lys Asn Glu Ile Phe Lys Thr Arg Gly Val Tyr Cys Ala Gly Asn
1               5                   10                  15

Ala

<210> SEQ ID NO 484
<211> LENGTH: 17
<212> TYPE: PRT
<213> ORGANISM: Haemophilus influenzae

<400> SEQUENCE: 484

Gly Lys Asn Glu Ile Phe Lys Thr Arg Gly Val Tyr Cys Val Gly Asn
1               5                   10                  15

Ser

<210> SEQ ID NO 485
<211> LENGTH: 21
<212> TYPE: PRT
<213> ORGANISM: Haemophilus influenzae

<400> SEQUENCE: 485

Lys Arg Asp Thr Ser Pro Arg Asn Pro Trp Gly Lys Thr Ser Thr Trp
1               5                   10                  15

Ile Ala Glu Ile Pro
            20

<210> SEQ ID NO 486
<211> LENGTH: 21
<212> TYPE: PRT
<213> ORGANISM: Haemophilus influenzae

<400> SEQUENCE: 486

Lys Arg Asp Thr Ser Pro Arg Asn Pro Trp Gly Lys Thr Leu Thr Trp
1               5                   10                  15

Ile Ala Glu Ile Pro
            20

<210> SEQ ID NO 487
<211> LENGTH: 21
<212> TYPE: PRT
<213> ORGANISM: Haemophilus influenzae

<400> SEQUENCE: 487

Lys Arg Asp Thr Ser Pro Arg Asn Pro Trp Ser Lys Thr Ser Thr Trp
1               5                   10                  15

Ile Ala Glu Ile Pro
            20

<210> SEQ ID NO 488
<211> LENGTH: 22
<212> TYPE: PRT
<213> ORGANISM: Haemophilus influenzae

<400> SEQUENCE: 488

Asp Asn Leu Phe Asn Arg Ala Tyr Asn Pro Tyr Leu Gly Glu Leu Ala
1               5                   10                  15

Ser Gly Thr Gly Arg Asn
            20

<210> SEQ ID NO 489
<211> LENGTH: 22
<212> TYPE: PRT
<213> ORGANISM: Haemophilus influenzae

<400> SEQUENCE: 489

Asp Asn Leu Phe Asn Arg Ala Tyr Lys Pro Tyr Leu Gly Glu Leu Ala
1               5                   10                  15

Ser Gly Thr Gly Arg Asn
            20

<210> SEQ ID NO 490
<211> LENGTH: 17
<212> TYPE: PRT
<213> ORGANISM: Haemophilus influenzae

<400> SEQUENCE: 490

Phe Tyr Ser Thr Ala Leu Asp Ser Gly Gln Ser Gly Gly Ser Ser Gln
1               5                   10                  15

Phe

<210> SEQ ID NO 491
<211> LENGTH: 16
<212> TYPE: PRT
<213> ORGANISM: Haemophilus influenzae

<400> SEQUENCE: 491

Tyr Gly Tyr Ser Gln Arg Glu Val Ser Gln Asp Tyr Arg Ile Gly Gly
1               5                   10                  15

<210> SEQ ID NO 492
<211> LENGTH: 13
<212> TYPE: PRT
<213> ORGANISM: Haemophilus influenzae

<400> SEQUENCE: 492

Leu Pro Gln Arg Ser Val Ile Leu Gln Pro Ser Gly Lys
1               5                   10

<210> SEQ ID NO 493
<211> LENGTH: 13
<212> TYPE: PRT
<213> ORGANISM: Haemophilus influenzae

<400> SEQUENCE: 493

Leu Pro Lys Arg Ser Val Ile Leu Gln Pro Ser Gly Lys
1               5                   10

<210> SEQ ID NO 494
<211> LENGTH: 25
<212> TYPE: PRT
<213> ORGANISM: Haemophilus influenzae

<400> SEQUENCE: 494

Met Pro Asn Ile Gln Glu Met Phe Phe Ser Gln Val Ser Val Ser Asn
1               5                   10                  15

Ala Gly Val Asn Thr Ala Leu Lys Pro
            20                  25

<210> SEQ ID NO 495
<211> LENGTH: 25
<212> TYPE: PRT
<213> ORGANISM: Haemophilus influenzae

<400> SEQUENCE: 495

Met Pro Asn Ile Gln Glu Met Phe Phe Ser Gln Val Ser Val Ser Asp
1               5                   10                  15

Ala Gly Val Asn Thr Ala Leu Lys Pro
            20                  25

<210> SEQ ID NO 496
<211> LENGTH: 25
<212> TYPE: PRT
<213> ORGANISM: Haemophilus influenzae

<400> SEQUENCE: 496

Met Pro Asn Ile Gln Glu Met Phe Phe Ser Gln Val Ser Val Ser Asp
1               5                   10                  15

Val Gly Val Asn Thr Ala Leu Lys Pro

```
                        20                  25

<210> SEQ ID NO 497
<211> LENGTH: 11
<212> TYPE: PRT
<213> ORGANISM: Haemophilus influenzae

<400> SEQUENCE: 497

Ile Leu Lys Gln Gly Tyr Gly Leu Ser Arg Ile
1               5                   10

<210> SEQ ID NO 498
<211> LENGTH: 11
<212> TYPE: PRT
<213> ORGANISM: Haemophilus influenzae

<400> SEQUENCE: 498

Ile Leu Lys Gln Gly Tyr Gly Leu Ser Arg Val
1               5                   10

<210> SEQ ID NO 499
<211> LENGTH: 11
<212> TYPE: PRT
<213> ORGANISM: Haemophilus influenzae

<400> SEQUENCE: 499

Thr Leu Lys Gln Gly Tyr Gly Leu Ser Arg Ile
1               5                   10

<210> SEQ ID NO 500
<211> LENGTH: 28
<212> TYPE: PRT
<213> ORGANISM: Haemophilus influenzae

<400> SEQUENCE: 500

Gln Asn Leu Leu Asp Lys Arg Tyr Val Asp Pro Leu Asp Ala Gly Asn
1               5                   10                  15

Asp Ala Ala Ser Gln Arg Tyr Tyr Ser Ser Leu Asn
            20                  25

<210> SEQ ID NO 501
<211> LENGTH: 28
<212> TYPE: PRT
<213> ORGANISM: Haemophilus influenzae

<400> SEQUENCE: 501

Gln Asn Leu Leu Asp Lys Arg Tyr Val Asp Pro Leu Asp Ser Gly Asn
1               5                   10                  15

Asp Ala Ala Ser Gln Arg Tyr Tyr Ser Ser Leu Asn
            20                  25

<210> SEQ ID NO 502
<211> LENGTH: 28
<212> TYPE: PRT
<213> ORGANISM: Haemophilus influenzae

<400> SEQUENCE: 502

Gln Asn Leu Leu Asp Lys Arg Tyr Val Asp Pro Leu Asp Ala Gly Asn
1               5                   10                  15

Asp Ser Ala Ser Gln Arg Tyr Tyr Ser Ser Leu Asn
            20                  25

<210> SEQ ID NO 503
```

```
<211> LENGTH: 15
<212> TYPE: PRT
<213> ORGANISM: Haemophilus influenzae

<400> SEQUENCE: 503

Asp Lys Thr Arg Val Leu Tyr Asn Phe Ala Arg Gly Arg Thr Tyr
1               5                   10                  15

<210> SEQ ID NO 504
<211> LENGTH: 15
<212> TYPE: PRT
<213> ORGANISM: Haemophilus influenzae

<400> SEQUENCE: 504

Asp Lys Thr Arg Val Leu Tyr Asn Phe Ala Arg Gly Arg Thr Tyr
1               5                   10                  15

<210> SEQ ID NO 505
<211> LENGTH: 15
<212> TYPE: PRT
<213> ORGANISM: Haemophilus influenzae

<400> SEQUENCE: 505

Asp Lys Pro Arg Val Leu Tyr Asn Phe Ala Arg Gly Arg Thr Tyr
1               5                   10                  15

<210> SEQ ID NO 506
<211> LENGTH: 31
<212> TYPE: PRT
<213> ORGANISM: Haemophilus influenzae

<400> SEQUENCE: 506

Asn Ser Asp Gln Asn Gly Phe Gln Arg Gly Glu Ile Lys Pro Glu Asn
1               5                   10                  15

Ile Ser Ile Asn Gly Ala Asp Pro Asn Gln Thr Ala Tyr Phe Val
            20                  25                  30

<210> SEQ ID NO 507
<211> LENGTH: 31
<212> TYPE: PRT
<213> ORGANISM: Haemophilus influenzae

<400> SEQUENCE: 507

Asn Ser Asp Gln Asp Gly Phe Gln Arg Gly Glu Ile Lys Pro Glu Asn
1               5                   10                  15

Ile Ser Ile Asn Gly Ala Asp Pro Asn Gln Thr Ala Tyr Phe Val
            20                  25                  30

<210> SEQ ID NO 508
<211> LENGTH: 25
<212> TYPE: PRT
<213> ORGANISM: Haemophilus influenzae

<400> SEQUENCE: 508

Asn Trp Thr Pro Gln Glu Lys Glu Arg Ile Glu Phe Gly Leu Arg Tyr
1               5                   10                  15

Ser Asn Tyr Lys Glu Leu Lys Tyr Phe
            20                  25

<210> SEQ ID NO 509
<211> LENGTH: 25
<212> TYPE: PRT
<213> ORGANISM: Haemophilus influenzae
```

```
<400> SEQUENCE: 509

Asn Trp Thr Pro Gln Glu Lys Glu Arg Ile Glu Leu Gly Leu Arg Tyr
1               5                   10                  15

Ser Asn Tyr Lys Glu Leu Lys Tyr Phe
            20                  25

<210> SEQ ID NO 510
<211> LENGTH: 15
<212> TYPE: PRT
<213> ORGANISM: Haemophilus influenzae

<400> SEQUENCE: 510

Gly Arg Ser Phe Ala Ser Leu Lys Leu Ala Asn Arg Leu Ile Lys
1               5                   10                  15

<210> SEQ ID NO 511
<211> LENGTH: 15
<212> TYPE: PRT
<213> ORGANISM: Haemophilus influenzae

<400> SEQUENCE: 511

Gly Arg Ser Phe Ala Ser Leu Lys Leu Ala Asn Gly Ile Leu Lys
1               5                   10                  15

<210> SEQ ID NO 512
<211> LENGTH: 15
<212> TYPE: PRT
<213> ORGANISM: Haemophilus influenzae

<400> SEQUENCE: 512

Gly Arg Ser Phe Ala Ser Leu Lys Leu Ala Tyr Arg Ile Leu Lys
1               5                   10                  15

<210> SEQ ID NO 513
<211> LENGTH: 15
<212> TYPE: PRT
<213> ORGANISM: Haemophilus influenzae

<400> SEQUENCE: 513

Gly Arg Ser Phe Ala Pro Leu Lys Leu Ala Asn Gly Ile Leu Lys
1               5                   10                  15

<210> SEQ ID NO 514
<211> LENGTH: 43
<212> TYPE: PRT
<213> ORGANISM: Haemophilus influenzae

<400> SEQUENCE: 514

Glu Leu Gln Pro Lys Tyr Asn Lys Gln Thr Phe Asn Ile Leu Ala Glu
1               5                   10                  15

Lys Arg Leu Asn Asp Asn Leu Gly Met Val Leu Gly Tyr Ser Arg Arg
            20                  25                  30

Thr Ser Ser Ile Glu Gln Asn Arg Leu Ile Gly
            35                  40

<210> SEQ ID NO 515
<211> LENGTH: 43
<212> TYPE: PRT
<213> ORGANISM: Haemophilus influenzae

<400> SEQUENCE: 515

Glu Leu Gln Pro Lys Tyr Asp Lys Gln Thr Phe Asn Ile Leu Ala Glu
1               5                   10                  15
```

-continued

```
Lys Arg Leu Asn Asp Asn Leu Gly Met Val Phe Gly Tyr Ser Arg Arg
            20                  25                  30

Thr Ser Ser Ile Glu Gln Asn Arg Leu Ile Gly
        35                  40

<210> SEQ ID NO 516
<211> LENGTH: 43
<212> TYPE: PRT
<213> ORGANISM: Haemophilus influenzae

<400> SEQUENCE: 516

Glu Leu Gln Pro Lys Tyr Asn Lys Gln Thr Phe Asn Ile Leu Ala Glu
1               5                   10                  15

Lys Arg Leu Asn Asp Asn Leu Gly Met Val Phe Gly Tyr Ser Arg Arg
            20                  25                  30

Thr Ser Ser Ile Glu Gln Asn Arg Leu Ile Gly
        35                  40

<210> SEQ ID NO 517
<211> LENGTH: 20
<212> TYPE: PRT
<213> ORGANISM: Haemophilus influenzae

<400> SEQUENCE: 517

His Cys Ser Leu Tyr Pro Asn Pro Ser Lys Asn Cys Arg Pro Thr Leu
1               5                   10                  15

Asp Lys Pro Tyr
            20

<210> SEQ ID NO 518
<211> LENGTH: 20
<212> TYPE: PRT
<213> ORGANISM: Haemophilus influenzae

<400> SEQUENCE: 518

His Cys Ser Leu Tyr Pro Asn Pro Ser Lys Asn Cys Arg Pro Thr Arg
1               5                   10                  15

Asp Lys Pro Tyr
            20

<210> SEQ ID NO 519
<211> LENGTH: 13
<212> TYPE: PRT
<213> ORGANISM: Haemophilus influenzae

<400> SEQUENCE: 519

Ala Asn Glu Ser Thr Ile Ser Val Gly Lys Phe Lys Asn
1               5                   10

<210> SEQ ID NO 520
<211> LENGTH: 14
<212> TYPE: PRT
<213> ORGANISM: Haemophilus influenzae

<400> SEQUENCE: 520

Asn Pro Ser Phe Ala Glu Met Tyr Gly Trp Arg Tyr Gly Gly
1               5                   10

<210> SEQ ID NO 521
<211> LENGTH: 14
<212> TYPE: PRT
<213> ORGANISM: Haemophilus influenzae
```

<400> SEQUENCE: 521

Asn Pro Ser Phe Ser Glu Met Tyr Gly Trp Arg Tyr Gly Gly
1               5                   10

<210> SEQ ID NO 522
<211> LENGTH: 24
<212> TYPE: PRT
<213> ORGANISM: Haemophilus influenzae

<400> SEQUENCE: 522

Val Lys Asp Gln Lys Ile Asn Ala Gly Leu Ala Ser Val Ser Ser Tyr
1               5                   10                  15

Leu Phe Asp Ala Ile Gln Pro Ser
            20

<210> SEQ ID NO 523
<211> LENGTH: 24
<212> TYPE: PRT
<213> ORGANISM: Haemophilus influenzae

<400> SEQUENCE: 523

Val Lys Asp Gln Lys Ile Asn Thr Gly Leu Ala Ser Val Ser Ser Tyr
1               5                   10                  15

Leu Phe Asp Ala Ile Gln Pro Ser
            20

<210> SEQ ID NO 524
<211> LENGTH: 37
<212> TYPE: PRT
<213> ORGANISM: Haemophilus influenzae

<400> SEQUENCE: 524

Asn Leu Leu Asn Tyr Arg Tyr Val Thr Trp Glu Ala Val Arg Gln Thr
1               5                   10                  15

Ala Gln Gly Ala Val Asn Gln His Gln Asn Val Gly Asn Tyr Thr Arg
            20                  25                  30

Tyr Ala Ala Ser Gly
        35

<210> SEQ ID NO 525
<211> LENGTH: 37
<212> TYPE: PRT
<213> ORGANISM: Haemophilus influenzae

<400> SEQUENCE: 525

Asn Leu Phe Asn Tyr Arg Tyr Val Thr Trp Glu Ala Val Arg Gln Thr
1               5                   10                  15

Ala Gln Gly Ala Val Asn Gln His Gln Asn Val Gly Asn Tyr Thr Arg
            20                  25                  30

Tyr Ala Ala Ser Gly
        35

<210> SEQ ID NO 526
<211> LENGTH: 37
<212> TYPE: PRT
<213> ORGANISM: Haemophilus influenzae

<400> SEQUENCE: 526

Asn Leu Leu Asn Tyr Arg Tyr Val Thr Trp Glu Ala Leu Arg Gln Thr
1               5                   10                  15

Ala Gln Gly Ala Val Asn Gln His Gln Asn Val Gly Asn Tyr Thr Arg
            20                  25                  30

Tyr Ala Ala Ser Gly
        35

<210> SEQ ID NO 527
<211> LENGTH: 37
<212> TYPE: PRT
<213> ORGANISM: Haemophilus influenzae

<400> SEQUENCE: 527

Asn Leu Leu Asn Tyr Arg Tyr Val Thr Trp Glu Ala Val Arg Gln Thr
1               5                   10                  15

Ala Gln Gly Ala Val Asn Gln His Gln Asn Ile Gly Asn Tyr Thr Arg
            20                  25                  30

Tyr Ala Ala Ser Gly
        35

<210> SEQ ID NO 528
<211> LENGTH: 37
<212> TYPE: PRT
<213> ORGANISM: Haemophilus influenzae

<400> SEQUENCE: 528

Asn Leu Phe Asn Tyr Arg Tyr Val Thr Trp Glu Ala Val Arg Gln Thr
1               5                   10                  15

Ala Gln Gly Ala Val Asn Gln His Gln Asn Ile Gly Asn Tyr Thr Arg
            20                  25                  30

Tyr Ala Ala Ser Gly
        35

<210> SEQ ID NO 529
<211> LENGTH: 37
<212> TYPE: PRT
<213> ORGANISM: Haemophilus influenzae

<400> SEQUENCE: 529

Asn Leu Leu Asn Tyr Arg Tyr Val Thr Trp Glu Ala Val Arg Gln Thr
1               5                   10                  15

Ala Gln Gly Ala Val Asn Gln His Gln Asn Val Gly Ser Tyr Thr Arg
            20                  25                  30

Tyr Ala Ala Ser Gly
        35

<210> SEQ ID NO 530
<211> LENGTH: 37
<212> TYPE: PRT
<213> ORGANISM: Haemophilus influenzae

<400> SEQUENCE: 530

Asn Leu Phe Asn Tyr Arg Tyr Val Thr Trp Glu Ala Val Arg Gln Thr
1               5                   10                  15

Ala Gln Gly Ala Val Asn Gln His Gln Asn Val Gly Ser Tyr Thr Arg
            20                  25                  30

Tyr Ala Ala Ser Gly
        35

<210> SEQ ID NO 531
<211> LENGTH: 37
<212> TYPE: PRT
<213> ORGANISM: Haemophilus influenzae

<400> SEQUENCE: 531

Asn Leu Phe Asn Tyr Arg Tyr Val Thr Trp Glu Ala Val Arg Gln Thr
1               5                   10                  15

Ala Gln Gly Ala Val Asn Gln His Gln Asn Ile Gly Ser Tyr Thr Arg
            20                  25                  30

Tyr Ala Ala Ser Gly
            35

<210> SEQ ID NO 532
<211> LENGTH: 15
<212> TYPE: PRT
<213> ORGANISM: Haemophilus influenzae

<400> SEQUENCE: 532

Glu Thr Gln Val His Lys Asp Ala Leu Lys Gly Val Gln Ser Tyr
1               5                   10                  15

<210> SEQ ID NO 533
<211> LENGTH: 15
<212> TYPE: PRT
<213> ORGANISM: Haemophilus influenzae

<400> SEQUENCE: 533

Glu Thr Gln Val His Lys Asp Ala Leu Arg Gly Val Gln Ser Tyr
1               5                   10                  15

<210> SEQ ID NO 534
<211> LENGTH: 15
<212> TYPE: PRT
<213> ORGANISM: Haemophilus influenzae

<400> SEQUENCE: 534

Glu Thr Gln Val His Pro Asp Ala Leu Lys Gly Val Gln Ser Tyr
1               5                   10                  15

<210> SEQ ID NO 535
<211> LENGTH: 19
<212> TYPE: PRT
<213> ORGANISM: Haemophilus influenzae

<400> SEQUENCE: 535

Glu Thr Val Ser Val Ser Asp Tyr Thr Gly Ala Asn Arg Ile Lys Pro
1               5                   10                  15

Asn Pro Met

<210> SEQ ID NO 536
<211> LENGTH: 19
<212> TYPE: PRT
<213> ORGANISM: Haemophilus influenzae

<400> SEQUENCE: 536

Glu Ile Val Ser Val Ser Asp Tyr Thr Gly Ala Asn Arg Ile Lys Pro
1               5                   10                  15

Asn Pro Met

<210> SEQ ID NO 537
<211> LENGTH: 32
<212> TYPE: PRT
<213> ORGANISM: Haemophilus influenzae

<400> SEQUENCE: 537

```
Asp Gly Leu Arg Gln Ala Glu Thr Leu Ser Ser Gln Gly Phe Lys Glu
1               5                   10                  15

Leu Phe Glu Gly Tyr Gly Asn Phe Asn Asn Thr Arg Asn Ser Ile Glu
            20                  25                  30

<210> SEQ ID NO 538
<211> LENGTH: 18
<212> TYPE: PRT
<213> ORGANISM: Haemophilus influenzae

<400> SEQUENCE: 538

His Glu Ile Glu Asn Tyr Asp Tyr Lys Ile Tyr Pro Asn Lys Gln Ala
1               5                   10                  15

Asp Leu

<210> SEQ ID NO 539
<211> LENGTH: 18
<212> TYPE: PRT
<213> ORGANISM: Haemophilus influenzae

<400> SEQUENCE: 539

His Glu Ile Glu Asn Tyr Asp Tyr Lys Ile Tyr Pro Asn Lys Gln Thr
1               5                   10                  15

Asp Phe

<210> SEQ ID NO 540
<211> LENGTH: 18
<212> TYPE: PRT
<213> ORGANISM: Haemophilus influenzae

<400> SEQUENCE: 540

His Glu Ile Glu Asn Tyr Asp Tyr Lys Ile Tyr Pro Asn Lys Gln Thr
1               5                   10                  15

Asp Leu

<210> SEQ ID NO 541
<211> LENGTH: 12
<212> TYPE: PRT
<213> ORGANISM: Haemophilus influenzae

<400> SEQUENCE: 541

Phe Gly Glu Arg Ile Ile Asn Asp Gln Ser Lys Arg
1               5                   10

<210> SEQ ID NO 542
<211> LENGTH: 12
<212> TYPE: PRT
<213> ORGANISM: Haemophilus influenzae

<400> SEQUENCE: 542

His Gly Glu Arg Val Ile Asn Asp Gln Ser Lys Arg
1               5                   10

<210> SEQ ID NO 543
<211> LENGTH: 12
<212> TYPE: PRT
<213> ORGANISM: Haemophilus influenzae

<400> SEQUENCE: 543

His Gly Glu Arg Ile Ile Asn Asp Gln Ser Lys Arg
1               5                   10
```

-continued

```
<210> SEQ ID NO 544
<211> LENGTH: 12
<212> TYPE: PRT
<213> ORGANISM: Haemophilus influenzae

<400> SEQUENCE: 544

Tyr Gly Glu Arg Val Ile Asn Asp Gln Ser Lys Arg
1               5                   10

<210> SEQ ID NO 545
<211> LENGTH: 12
<212> TYPE: PRT
<213> ORGANISM: Haemaphysalis longicornis symbiote B

<400> SEQUENCE: 545

Tyr Gly Glu Arg Ile Ile Asn Asp Gln Ser Lys Arg
1               5                   10

<210> SEQ ID NO 546
<211> LENGTH: 15
<212> TYPE: PRT
<213> ORGANISM: Haemophilus influenzae

<400> SEQUENCE: 546

Thr Asn Lys Ala Arg Ser Asp Glu Tyr Cys His Gln Ser Thr Cys
1               5                   10                  15

<210> SEQ ID NO 547
<211> LENGTH: 15
<212> TYPE: PRT
<213> ORGANISM: Haemophilus influenzae

<400> SEQUENCE: 547

Thr Asn Lys Ala Arg Ser Asp Glu Tyr Cys His Gln Pro Thr Cys
1               5                   10                  15

<210> SEQ ID NO 548
<211> LENGTH: 15
<212> TYPE: PRT
<213> ORGANISM: Haemophilus influenzae

<400> SEQUENCE: 548

Thr Asn Lys Ala His Ser Asp Glu Tyr Cys His Gln Ser Thr Cys
1               5                   10                  15

<210> SEQ ID NO 549
<211> LENGTH: 12
<212> TYPE: PRT
<213> ORGANISM: Haemophilus influenzae

<400> SEQUENCE: 549

Asn Leu Ala Leu Leu Leu Arg Lys Thr Thr Tyr Lys
1               5                   10

<210> SEQ ID NO 550
<211> LENGTH: 12
<212> TYPE: PRT
<213> ORGANISM: Haemophilus influenzae

<400> SEQUENCE: 550

Asn Leu Ala Leu Leu Leu Arg Lys Thr Asp Tyr Lys
1               5                   10

<210> SEQ ID NO 551
<211> LENGTH: 29
```

```
<212> TYPE: PRT
<213> ORGANISM: Haemophilus influenzae

<400> SEQUENCE: 551

Phe Arg Ala Pro Thr Ser Asp Glu Ile Tyr Met Thr Phe Lys His Pro
1               5                   10                  15

Gln Phe Ser Ile Gln Pro Asn Thr Asp Leu Lys Ala Glu
            20                  25

<210> SEQ ID NO 552
<211> LENGTH: 29
<212> TYPE: PRT
<213> ORGANISM: Haemophilus influenzae

<400> SEQUENCE: 552

Phe Arg Ala Pro Thr Ser Asp Glu Ile Tyr Met Thr Phe Lys His Pro
1               5                   10                  15

Asp Phe Ser Ile Gly Pro Asn Thr Asp Leu Lys Ala Glu
            20                  25

<210> SEQ ID NO 553
<211> LENGTH: 29
<212> TYPE: PRT
<213> ORGANISM: Haemophilus influenzae

<400> SEQUENCE: 553

Phe Arg Ala Pro Thr Ser Asp Glu Ile Tyr Met Thr Phe Lys His Pro
1               5                   10                  15

Gln Phe Ser Ile Leu Pro Asn Thr Asp Leu Lys Ala Glu
            20                  25

<210> SEQ ID NO 554
<211> LENGTH: 17
<212> TYPE: PRT
<213> ORGANISM: Haemophilus influenzae

<400> SEQUENCE: 554

Ala Ala Lys Lys Ala Lys Asp Ser Phe Asn Ser Gln Trp Thr Ser Met
1               5                   10                  15

Val

<210> SEQ ID NO 555
<211> LENGTH: 17
<212> TYPE: PRT
<213> ORGANISM: Haemophilus influenzae

<400> SEQUENCE: 555

Ala Ala Lys Lys Ala Lys Asp Thr Phe Asn Ser Gln Trp Thr Ser Met
1               5                   10                  15

Val

<210> SEQ ID NO 556
<211> LENGTH: 17
<212> TYPE: PRT
<213> ORGANISM: Haemophilus influenzae

<400> SEQUENCE: 556

Ala Asn Gly Lys Glu Val Lys Asp Ser Arg Gly Leu Trp Arg Asn Asn
1               5                   10                  15

Arg
```

```
<210> SEQ ID NO 557
<211> LENGTH: 17
<212> TYPE: PRT
<213> ORGANISM: Haemophilus influenzae

<400> SEQUENCE: 557

Ala Asn Gly Lys Asp Val Lys Asp Ser Arg Gly Leu Trp Arg Asn Asn
1               5                   10                  15

Arg

<210> SEQ ID NO 558
<211> LENGTH: 17
<212> TYPE: PRT
<213> ORGANISM: Haemophilus influenzae

<400> SEQUENCE: 558

Val Asn Gly Lys Asp Val Lys Asp Ser Arg Gly Leu Trp Arg Asn Asn
1               5                   10                  15

Arg

<210> SEQ ID NO 559
<211> LENGTH: 25
<212> TYPE: PRT
<213> ORGANISM: Haemophilus influenzae

<400> SEQUENCE: 559

Asn Leu Thr Asn Lys Lys Tyr Leu Thr Trp Asp Ser Ala Arg Ser Val
1               5                   10                  15

Arg His Leu Gly Thr Ile Asn Arg Val
            20                  25

<210> SEQ ID NO 560
<211> LENGTH: 25
<212> TYPE: PRT
<213> ORGANISM: Haemophilus influenzae

<400> SEQUENCE: 560

Asn Leu Thr Asn Lys Lys Tyr Leu Thr Trp Asp Ser Ala Arg Ser Ile
1               5                   10                  15

Arg His Leu Gly Thr Ile Asn Arg Val
            20                  25

<210> SEQ ID NO 561
<211> LENGTH: 25
<212> TYPE: PRT
<213> ORGANISM: Haemophilus influenzae

<400> SEQUENCE: 561

Asn Leu Thr Asn Lys Lys Tyr Leu Thr Trp Asp Ser Ala Arg Ser Ile
1               5                   10                  15

Arg His Ile Gly Thr Ile Asn Arg Val
            20                  25

<210> SEQ ID NO 562
<211> LENGTH: 18
<212> TYPE: PRT
<213> ORGANISM: Haemophilus influenzae

<400> SEQUENCE: 562

Gln Arg Ile Lys Thr Arg Ala Arg Thr Asp Asp Tyr Cys Asp Ala Gly
1               5                   10                  15

Val Arg
```

```
<210> SEQ ID NO 563
<211> LENGTH: 18
<212> TYPE: PRT
<213> ORGANISM: Haemophilus influenzae

<400> SEQUENCE: 563

Gln Lys Ile Lys Thr Arg Ala Arg Thr Asp Asp Tyr Cys Asp Ala Gly
1               5                   10                  15

Val Arg

<210> SEQ ID NO 564
<211> LENGTH: 18
<212> TYPE: PRT
<213> ORGANISM: Haemophilus influenzae

<400> SEQUENCE: 564

Gln Arg Ile Lys Thr Arg Ala Arg Thr Asp Glu Tyr Cys Asp Ala Gly
1               5                   10                  15

Val Arg

<210> SEQ ID NO 565
<211> LENGTH: 17
<212> TYPE: PRT
<213> ORGANISM: Haemophilus influenzae

<400> SEQUENCE: 565

Gln Lys Gly Arg Met Asp Gly Asn Ile Pro Met Asn Ala Ile Gln Pro
1               5                   10                  15

Lys

<210> SEQ ID NO 566
<211> LENGTH: 17
<212> TYPE: PRT
<213> ORGANISM: Haemophilus influenzae

<400> SEQUENCE: 566

Gln Lys Gly Arg Ile Asn Gly Asn Ile Pro Met Asn Ala Ile Gln Pro
1               5                   10                  15

Lys

<210> SEQ ID NO 567
<211> LENGTH: 17
<212> TYPE: PRT
<213> ORGANISM: Haemophilus influenzae

<400> SEQUENCE: 567

Gln Lys Gly Arg Met Asn Gly Asn Ile Pro Met Asn Ala Ile Gln Pro
1               5                   10                  15

Lys

<210> SEQ ID NO 568
<211> LENGTH: 17
<212> TYPE: PRT
<213> ORGANISM: Haemophilus influenzae

<400> SEQUENCE: 568

Gln Lys Gly Arg Met Asn Gly Asn Ile Pro Met Asn Ala Ile Gln Pro
1               5                   10                  15

Arg
```

<210> SEQ ID NO 569
<211> LENGTH: 54
<212> TYPE: PRT
<213> ORGANISM: Haemophilus influenzae

<400> SEQUENCE: 569

Gly Tyr Val Gln Pro Ile Lys Asn Leu Thr Ile Arg Ala Gly Val Tyr
1               5                   10                  15

Asn Leu Thr Asn Arg Lys Tyr Ile Thr Trp Asp Ser Ala Arg Ser Ile
            20                  25                  30

Arg Ser Phe Gly Thr Ser Asn Val Ile Glu Gln Thr Thr Gly Leu Gly
        35                  40                  45

Ile Asn Arg Phe Tyr Ala
    50

<210> SEQ ID NO 570
<211> LENGTH: 54
<212> TYPE: PRT
<213> ORGANISM: Haemophilus influenzae

<400> SEQUENCE: 570

Gly Tyr Val Gln Pro Ile Lys Asn Leu Thr Ile Arg Ala Gly Val Tyr
1               5                   10                  15

Asn Leu Thr Asn Arg Lys Tyr Ile Thr Trp Asp Ser Val Arg Ser Ile
            20                  25                  30

Arg Ser Phe Gly Thr Ser Asn Val Ile Glu Gln Thr Thr Gly Gln Gly
        35                  40                  45

Ile Asn Arg Phe Tyr Ala
    50

<210> SEQ ID NO 571
<211> LENGTH: 54
<212> TYPE: PRT
<213> ORGANISM: Haemophilus influenzae

<400> SEQUENCE: 571

Gly Tyr Val Gln Pro Ile Lys Asn Leu Thr Ile Arg Ala Gly Val Tyr
1               5                   10                  15

Asn Leu Thr Asn Arg Lys Tyr Ile Thr Trp Asp Ser Ala Arg Ser Ile
            20                  25                  30

Arg Ser Phe Gly Thr Ser Asn Val Ile Glu Gln Thr Thr Gly Gln Gly
        35                  40                  45

Ile Asn Arg Phe Tyr Ala
    50

<210> SEQ ID NO 572
<211> LENGTH: 54
<212> TYPE: PRT
<213> ORGANISM: Haemophilus influenzae

<400> SEQUENCE: 572

Gly Tyr Val Gln Pro Ile Lys Asn Leu Thr Ile Arg Ala Gly Val Tyr
1               5                   10                  15

Asn Leu Thr Asn Arg Lys Tyr Ile Thr Trp Asp Ser Ala Arg Ser Ile
            20                  25                  30

Arg Ser Phe Gly Thr Ser Asn Val Ile Glu Gln Lys Thr Gly Gln Gly
        35                  40                  45

Ile Asn Arg Phe Tyr Ala
    50

-continued

```
<210> SEQ ID NO 573
<211> LENGTH: 54
<212> TYPE: PRT
<213> ORGANISM: Haemophilus influenzae

<400> SEQUENCE: 573

Gly Tyr Val Gln Pro Ile Lys Asn Leu Thr Ile Arg Ala Gly Val Tyr
1               5                   10                  15

Asn Leu Thr Asn Arg Lys Tyr Ile Thr Trp Asp Ser Ala Arg Ser Ile
            20                  25                  30

Arg Ser Phe Gly Thr Ser Asn Val Ile Glu Gln Ser Thr Gly Leu Gly
        35                  40                  45

Ile Asn Arg Phe Tyr Ala
    50

<210> SEQ ID NO 574
<211> LENGTH: 54
<212> TYPE: PRT
<213> ORGANISM: Haemophilus influenzae

<400> SEQUENCE: 574

Gly Tyr Val Gln Pro Ile Lys Asn Leu Thr Ile Arg Ala Gly Val Tyr
1               5                   10                  15

Asn Leu Thr Asn Arg Lys Tyr Ile Thr Trp Asp Ser Ala Arg Ser Ile
            20                  25                  30

Arg Ser Phe Gly Thr Ser Asn Val Ile Glu Gln Ser Thr Gly Gln Gly
        35                  40                  45

Ile Asn Arg Phe Tyr Ala
    50

<210> SEQ ID NO 575
<211> LENGTH: 26
<212> TYPE: PRT
<213> ORGANISM: Haemophilus influenzae

<400> SEQUENCE: 575

His Glu Leu Glu Asn Tyr Asp Tyr Lys Asn Ala Asp Ser Leu Thr Gln
1               5                   10                  15

Gly Lys Arg Arg Glu Lys Ala Asp Pro Tyr
            20                  25

<210> SEQ ID NO 576
<211> LENGTH: 26
<212> TYPE: PRT
<213> ORGANISM: Haemophilus influenzae

<400> SEQUENCE: 576

His Glu Leu Glu Asn Tyr Gly Tyr Lys Asn Tyr Asp Asp Lys Ile Gln
1               5                   10                  15

Gly Lys Arg Arg Glu Lys Ala Asp Pro Tyr
            20                  25

<210> SEQ ID NO 577
<211> LENGTH: 35
<212> TYPE: PRT
<213> ORGANISM: Haemophilus influenzae

<400> SEQUENCE: 577

Asp Ser Arg His Thr Asn Asp Lys Thr Lys Arg Arg Asn Ile Ser Phe
1               5                   10                  15
```

```
Ser Tyr Glu Asn Phe Ser Gln Thr Pro Phe Trp Asp Thr Leu Lys Ile
            20                  25                  30

Thr Tyr Ser
        35

<210> SEQ ID NO 578
<211> LENGTH: 35
<212> TYPE: PRT
<213> ORGANISM: Haemophilus influenzae

<400> SEQUENCE: 578

Asp Ser Arg His Thr Asn Asp Lys Thr Lys Arg Arg Asn Ile Ser Phe
1               5                   10                  15

Ser Tyr Glu Asn Tyr Ser Gln Thr Pro Phe Trp Asp Thr Leu Lys Ile
            20                  25                  30

Thr Tyr Ser
        35

<210> SEQ ID NO 579
<211> LENGTH: 35
<212> TYPE: PRT
<213> ORGANISM: Haemophilus influenzae

<400> SEQUENCE: 579

Asp Ser Arg His Thr Asn Asp Lys Thr Lys Arg Arg Asn Ile Ser Phe
1               5                   10                  15

Ser Tyr Glu Asn Phe Ser Gln Thr Pro Phe Trp Asp Thr Leu Lys Leu
            20                  25                  30

Thr Tyr Ser
        35

<210> SEQ ID NO 580
<211> LENGTH: 35
<212> TYPE: PRT
<213> ORGANISM: Haemophilus influenzae

<400> SEQUENCE: 580

Asp Ser Arg His Thr Asn Asp Lys Thr Lys Arg Arg Asn Ile Ser Phe
1               5                   10                  15

Ser Tyr Glu Asn Phe Ser Gln Thr Pro Phe Trp Asp Thr Leu Lys Ile
            20                  25                  30

Thr Phe Ser
        35

<210> SEQ ID NO 581
<211> LENGTH: 19
<212> TYPE: PRT
<213> ORGANISM: Haemophilus influenzae

<400> SEQUENCE: 581

Trp Gln Glu Arg Asp Leu Asp Thr Asn Thr Gln Gln Leu Asn Leu Asp
1               5                   10                  15

Leu Thr Lys

<210> SEQ ID NO 582
<211> LENGTH: 14
<212> TYPE: PRT
<213> ORGANISM: Haemophilus influenzae

<400> SEQUENCE: 582
```

```
Leu Cys Pro Arg Val Asp Pro Glu Phe Ser Phe Leu Leu Pro
1               5                   10
```

<210> SEQ ID NO 583
<211> LENGTH: 14
<212> TYPE: PRT
<213> ORGANISM: Haemophilus influenzae

<400> SEQUENCE: 583

```
Leu Cys His Arg Val Asp Pro Glu Phe Ser Phe Leu Leu Pro
1               5                   10
```

<210> SEQ ID NO 584
<211> LENGTH: 14
<212> TYPE: PRT
<213> ORGANISM: Haemophilus influenzae

<400> SEQUENCE: 584

```
Leu Cys Thr Arg Val Asp Pro Glu Phe Ser Phe Leu Leu Pro
1               5                   10
```

<210> SEQ ID NO 585
<211> LENGTH: 24
<212> TYPE: PRT
<213> ORGANISM: Haemophilus influenzae

<400> SEQUENCE: 585

```
Gln Pro Lys Tyr Lys His Gly Val Thr Pro Lys Leu Pro Asp Asp Ile
1               5                   10                  15

Val Lys Gly Leu Phe Ile Pro Leu
            20
```

<210> SEQ ID NO 586
<211> LENGTH: 27
<212> TYPE: PRT
<213> ORGANISM: Haemophilus influenzae

<400> SEQUENCE: 586

```
Ala Pro Thr Ser Asp Glu Met Tyr Phe Thr Phe Lys His Pro Asp Phe
1               5                   10                  15

Thr Ile Leu Pro Asn Thr Asn Leu Lys Pro Glu
            20                  25
```

<210> SEQ ID NO 587
<211> LENGTH: 27
<212> TYPE: PRT
<213> ORGANISM: Haemophilus influenzae

<400> SEQUENCE: 587

```
Thr Pro Thr Ser Asp Glu Met Tyr Phe Thr Phe Lys His Pro Asp Phe
1               5                   10                  15

Thr Ile Leu Pro Asn Thr Asp Leu Lys Pro Glu
            20                  25
```

<210> SEQ ID NO 588
<211> LENGTH: 27
<212> TYPE: PRT
<213> ORGANISM: Haemophilus influenzae

<400> SEQUENCE: 588

```
Ala Pro Thr Ser Asp Glu Met Tyr Phe Thr Phe Lys His Pro Asp Phe
1               5                   10                  15

Thr Ile Phe Pro Asn Thr Asn Leu Lys Pro Glu
```

```
<210> SEQ ID NO 589
<211> LENGTH: 20
<212> TYPE: PRT
<213> ORGANISM: Haemophilus influenzae
<220> FEATURE:
<221> NAME/KEY: MISC_FEATURE
<222> LOCATION: (8)..(8)
<223> OTHER INFORMATION: Val or Ile

<400> SEQUENCE: 589

Thr Leu Asn Lys Asp Asp Gly Xaa Tyr Tyr Leu Asn Gly Ser Gln Ser
1               5                   10                  15

Gly Lys Gly Gln
            20

<210> SEQ ID NO 590
<211> LENGTH: 20
<212> TYPE: PRT
<213> ORGANISM: Haemophilus influenzae
<220> FEATURE:
<221> NAME/KEY: MISC_FEATURE
<222> LOCATION: (10)..(10)
<223> OTHER INFORMATION: Thr or Ser

<400> SEQUENCE: 590

Gly Asp Asn Leu Asp Asp Phe Gly Asn Xaa Val Tyr Gly Lys Leu Asn
1               5                   10                  15

Ala Asp Arg Arg
            20

<210> SEQ ID NO 591
<211> LENGTH: 15
<212> TYPE: PRT
<213> ORGANISM: Haemophilus influenzae
<220> FEATURE:
<221> NAME/KEY: MISC_FEATURE
<222> LOCATION: (12)..(12)
<223> OTHER INFORMATION: Ile or Thr

<400> SEQUENCE: 591

Gln Arg Arg Val Asp Ile Ser Thr Asn Ser Ala Xaa Ser His Lys
1               5                   10                  15
```